US008309531B2

(12) United States Patent
Turner et al.

(10) Patent No.: US 8,309,531 B2
(45) Date of Patent: Nov. 13, 2012

(54) ADMINISTRATION OF INTERFERON FOR PROPHYLAXIS AGAINST OR TREATMENT OF PATHOGENIC INFECTION

(75) Inventors: Jeffrey D. Turner, Toronto (CA); Jane E. Ennis, Toronto (CA)

(73) Assignee: Defyrus, Inc., Toronto (CA)

( * ) Notice: Subject to any disclaimer, the term of this patent is extended or adjusted under 35 U.S.C. 154(b) by 7 days.

(21) Appl. No.: 12/797,575

(22) Filed: Jun. 9, 2010

(65) Prior Publication Data

US 2011/0000480 A1 Jan. 6, 2011

Related U.S. Application Data

(60) Provisional application No. 61/185,261, filed on Jun. 9, 2009.

(51) Int. Cl.
*C12N 15/00* (2006.01)
*C07H 21/02* (2006.01)
*A61K 48/00* (2006.01)

(52) U.S. Cl. ...................................... 514/44 R; 514/1.1

(58) Field of Classification Search .................. None
See application file for complete search history.

(56) References Cited

U.S. PATENT DOCUMENTS

| 4,450,103 | A | 5/1984 | Konrad et al. |
|---|---|---|---|
| 4,588,585 | A | 5/1986 | Mark et al. |
| 4,695,623 | A | 9/1987 | Stabinsky |
| 4,737,462 | A | 4/1988 | Mark et al. |
| 4,897,471 | A | 1/1990 | Stabinsky |
| 4,959,314 | A | 9/1990 | Mark et al. |
| 5,372,808 | A | 12/1994 | Blatt et al. |
| 5,541,293 | A | 7/1996 | Stabinsky |
| 5,738,845 | A | 4/1998 | Imakawa |
| 5,980,884 | A | 11/1999 | Blatt et al. |
| 6,376,236 | B1 | 4/2002 | Dubensky et al. |
| 6,432,699 | B1 | 8/2002 | Meruelo et al. |
| 6,565,853 | B1 | 5/2003 | Jacobs |
| 6,730,822 | B1 | 5/2004 | Ivarie et al. |
| 6,800,289 | B2 | 10/2004 | Nagata et al. |
| 6,835,557 | B1 | 12/2004 | Weissmann |
| 6,936,257 | B1 | 8/2005 | Bennett |
| 6,962,978 | B2 | 11/2005 | Pepinsky et al. |
| 7,223,409 | B2 | 5/2007 | Nagata et al. |
| 7,238,344 | B2 | 7/2007 | Pedersen et al. |
| 7,442,527 | B2 | 10/2008 | Palese et al. |
| 2004/0247565 | A1 | 12/2004 | Liu et al. |
| 2006/0147466 | A1* | 7/2006 | O'Hagan .................. 424/203.1 |
| 2007/0243163 | A1 | 10/2007 | Liu |
| 2010/0047274 | A1 | 2/2010 | Wu et al. |

FOREIGN PATENT DOCUMENTS

| EP | 0422697 | 4/1991 |
|---|---|---|
| EP | 1078639 | 2/2001 |
| WO | WO 97/42323 | 11/1997 |
| WO | WO 98/17801 | 4/1998 |
| WO | WO 00/09086 | 2/2000 |
| WO | WO 2007/044083 | 4/2007 |
| WO | WO 2008/101349 | 8/2008 |
| WO | WO 00/09675 | 2/2010 |

OTHER PUBLICATIONS

Moraes, 2003, Vaccine, 22:268-279.*
Gutierro, Vaccine, 2002. 20:2181-2190.*
Moraes, 2001, Biotechniques, 31:1050-1056.*
Blatt, J Interferon Cytokine Res 1996; 16: 489-499.*
Sullivan, Nature, 2000,408:605-609.*
Huang, Vaccine, 2006, 23:794-801.*
Adolf et al., "Natural Human Interferon-α 2 is O-Glycosylated," *Biochem. J.* 276:511-518, 1991.
Aguilar et al., "Variation in Interferon Sensitivity and Induction Among Strains of Eastern Equine Encephalitis Virus," *J. Virol.* 79:11300-11310, 2005.
Ahmed et al., "Selective Expression of Nonsecreted Interferon by an Adenoviral Vector Confers Antiproliferative and Antiviral Properties and Causes Reduction of Tumor Growth in Nude Mice," *J. Interferon Cytokine Res.* 21:399-408, 2001.
Ahmed et al., "In Vivo Tumor Suppression by Adenovirus-Mediated Interferon Alpha2b Gene Delivery," *Hum. Gene Ther.* 10:77-84, 1999.
Akai et al., "Effect of Low-Dose Human Interferon-alpha on Shipping Fever of Thoroughbred Racehorses," *J. Equine Sci.* 19:91-95, 2008.
Ausar et al., "Analysis of the Thermal and pH Stability of Human Respiratory Syncytial Virus," *Mol. Pharm.* 2:491-499, 2005.
Barabe et al., "Single-Dose, Fast-Acting Vaccine Candidate Against Western Equine Encephalitis Virus Completely Protects Mice from Intranasal Challenge with Different Strains of the Virus," *Vaccine* 25:6271-6276, 2007.
Bocci, "What is the Role of Carbohydrates in Interferons," *Trends Biochem. Sci.* 8:432-434, 1983.
Brassard et al., "Interferon-α as an Immunotherapeutic Protein," *J. Leukoc. Bio.* 71:565-581, 2002.
Chinsangaram et al., "Novel Viral Disease Control Strategy: Adenovirus Expressing Alpha Interferon Rapidly Protects Swine from Foot-and Mouth Disease," *J. Virol.* 77:1621-1625, 2003.
Cummins et al., "Natural Human Interferon-α Administered Orally as a Treatment of Bovine Respiratory Disease Complex," *J. Interferon Cytokine Res.* 19:907-910, 1999.
Fan et al., "Solution Behavior of IFN-β-1a: An Empirical Phase Diagram Based Approach," *J. Pharm. Sci.* 94:1893-1911, 2005.
INFERGEN® Packet Insert, Revised Dec. 2007, Distributed by Valeant Pharmaceuticals, Inc.
Kinney et al., "Recombinant Vaccinia Virus/ Venezuelan Equine Encephalitis (VEE) Virus Protects Mice from Peripheral VEE Virus Challenge," *J. Virol.* 62:4697-4702, 1988.

(Continued)

Primary Examiner — Valarie Bertoglio
(74) Attorney, Agent, or Firm — Clark & Elbing LLP; Todd Armstrong

(57) ABSTRACT

The invention provides compositions and methods for the prophylaxis or treatment of diseases or disorders in a subject (e.g., a mammal, such as a human) including, e.g., diseases or disorders caused by biological agents, autoimmune diseases, and cancer. The compositions include a delivery vector (e.g., a viral vector, such as an Ad5 vector) encoding an interferon (e.g., IFN-α), and are provided to the subject by, e.g., intranasal or pulmonary administration.

37 Claims, 12 Drawing Sheets

OTHER PUBLICATIONS

Kueltzo et al., "Derivative Absorbance Spectroscopy and Protein Phase Diagrams as Tools for Comprehensive Protein Characterization: A bGCSF Case Study," *J. Pharm. Sci.* 92:1805-1820, 2003.

Lukaszewski and Brooks, "Pegylated Alpha Interferon is an Effective Treatment for Virulent Venezuelan Equine Encephalitis Virus and has Profound Effects on the Host Immune Response to Infection," *J. Virol.* 74:5006-5015, 2000.

Mecchia et al., "Type I Concensus Interferon (CIFN) Gene Transfer Into Human Melanoma Cells Up-Regulates p53 and Enhances Cisplatin-Induced Apoptosis: Implications for New Therapeutic Strategies With IFN-alpha," *Gene Ther*. 7:167-179, 2000.
Moore et al., "Treatment of Inflammatory Airway Disease in Young Standardbreds With Interferon Alpha," *Can. Vet. J*. 45:594-601, 2004.
O'Brien et al., "Alpha Interferon as an Adenovirus-Vectored Vaccine Adjuvant and Antiviral in Venezuelan Equine Encephalitis Virus Infection," *J. Gen. Virol*. 90: 1-9, 2009.
Rexroad et al., "Effect of pH and Ionic Strength on the Physical Stability of Adenovirus Type 5," *J. Pharm. Sci*. 95:237-247, 2006.
Richardson et al., "Enhanced Protection Against Ebola Virus Mediated by an Improved Adenovirus-Based *Vaccine," PLoS ONE* 4: e5308, 2009.
Robb, "Failure of the Merck HIV Vaccine: An Uncertain Step Forward," *Lancet* 372:1857-1858, 2008.
Santodonato et al. "Antitumor Activity of Recombinant Adenoviral Vectors Expressing Murine IFN-α in Mice Injected with Metastatic IFN-Resistant Tumor Cells," *Cancer Gene Ther*. 8:63-72, 2001.
Sviatchenko et al., "The Immunogenic Properties of a Recombinant Vaccinia Virus with an Incorporated DNA the 26S RNA of the Venezuelan Equine Encephalomyelitis Virus," *Voprosy Virusologii* 38:222-226, 1993 (English Abstract Only).
Tüting et al., "Interferon-α Gene Therapy for Cancer: Retroviral Transduction of Fibroblasts and Particle-Mediated Transfection of Tumor Cells are Both Effective Strategies for Gene Delivery in Murine Tumor Models," *Gene Ther*. 4:1053-1060, 1997.
Wu et al., "Complete Protection of Mice Against a Lethal Dose Challenge of Western Equine Encephalitis Virus After Immunization with an Adenovirus-Vectored Vaccine," *Vaccine* 25:4368-4375, 2007.
Wu et al., "Pre- and Post-Exposure Protection Against Western Equine Encephalitis Virus After Single Inoculation with Adenovirus Vector Expressing Interferon Alpha," *Virology* 369:206-213, 2007.
Yeow et al., "Antiviral Activities of Individual Murine IFN-α Subtypes in Vivo: Intramuscular Injection of IFN Expression Constructs Reduces Cytomegalovirus Replication," *J. Immunol*. 160: 2932-2939, 1998.
Zhang et al., "Treatment of a Human Breast Cancer Xenograft with an Adenovirus Vector Containing an Interferon Gene Results in Rapid Regression Due to Viral Oncolysis and Gene Therapy," *Proc. Natl. Acad. Sci. USA* 93:4513-4518, 1996.
Croyle et al., "Development of Novel Formulations that Enhance Adenoviral-Mediated Gene Expression in the Lung in Vitro and in Vivo," *Mol. Ther*. 4:22-28, 2001.
International Search Report for International Application No. PCT/CA2010/000844 mailed on Aug. 13, 2010.
Written Opinion of the International Searching Authority for International Application No. PCT/CA2010/000844 mailed on Aug. 13, 2010.
Alberti et al., "Interferon Alfacon-1 : A novel Interferon for the Treatment of Chronic Hepatitis C," *Biodrugs* 12: 343-357, 1999.
Appaiahgari et al., "Seroprevalence of Neutralizing Antibodies to Adenovirus Type 5 among Children in India: Implications for Recombinant Adenovirus-Based Vaccines," *Clin. Vacc. Immunol*. 14: 1053-1055, 2007.
Borden et al., "Interferons at age 50: past, current and future impact on biomedicine," *Nat. Rev. Drug. Disc*. 6: 975-990, 2007.
Buchbinder et al., "Efficacy assessment of a cell-mediated immunity HIV-1 vaccine (the Step Study): a double-blind, randomised, placebo-controlled, test-of-concept trial," *Lancet* 372: 1881-1893, 2008.
Croyle et al., "Nasal Delivery of an Adenovirus-Based Vaccine Bypasses Pre-Existing Immunity to the Vaccine Carrier and Improves the Immune Response in Mice," *PloS ONE* 3: e3548, 2008.
Dart, Medical Toxicology, 3rd Edition. Lippincott, Williams & Williams, p. 512, 2004.
Demers et al., "Interferon-α2b Secretion by Adenovirus-Mediated Gene Delivery in Rat, Rabbit, and Chimpanzee Results in Similar Pharmacokinetic Profiles," *Tox. Appl. Pharm*. 180: 36-42, 2002.
Gowen et al., "Extended Protection Against Phlebovirus Infection Conferred by Recombinant Adenovirus Expressing Consensus Interferon (DEF201)," *Antimicrob. Ag. Chem*., 2012 (in press).
Gowen et al., "Use of Recombinant Adenovirus Vectored Consensus IFN-α to Avert Severe Arenavirus Infection," *PloS ONE 6: e26072*, 2011.
Grubb et al., "Inefficient gene transfer by adenovirus vector to cystic fibrosis airway epithelia of mice and humans," *Nature* 371: 802-806, 1994.
Hahn et al., "Western equine encephalitis virus is a recombinant virus," *Proc. Matl. Acad. Sci. USA*. 85: 5997-6001, 1988.
Hangalapura et al., "Delivery route, MyD88 signaling and cross-priming events determine the anti-tumor efficacy of an Adenovirus based melanoma vaccine," *Vaccine* 29: 2313-2321, 2011.
Hunt et al., "The First Human Epitope Map of the Alphaviral E1 and E2 Proteins Reveals a New E2 Epitope with Significant Virus Neutralizing Activity," *PloS Negl. Trop. Dis*. 4: 1-12, 2010.
Isaacs and Lindenmann, "Virus Interference. I. The Interferon," *Proc. R. Soc. Lond*. 147: 258, 1957.
Jolly, "Adenoviral Vectors: History and Perspective," Chapter 4, Concepts in Medicine, p. 39-54, Wiley-Liss, 2008.
Julander et al., "Treatment of Yellow Fever Virus with an Adenovirus-Vectored Interferon, DEF201, in a Hamster Model," *Antimicrob. Agents Chemother*. 55: 2067-2073, 2011.
Keedy et al., "Phase I study of adenovirus p53 administered by bronchoalveolar lavage in patients with bronchioloalveolar cell lung carcinoma: ECOG 6597," *J. Clin. Oncol*. 26: 4166-4171, 2008.
Knowles, "A controlled study of adenoviral-vector-mediated gene transfer in the nasal epithelium of patients with cystic fibrosis," *New England J. Med*. 333: 823-831, 1995.
Kumaki et al., "Single-dose intranasal administration with mDEF201 (adenovirus vectored mouse interferon-alpha) confers protection from mortality in a lethal SARS-CoV BALB/c mouse model," *Antiviral Res*. 89: 75-82, 2011.
Nagata et al., "Infectivity variation and genetic diversity among strains of Western equine encephalitis virus," *Journal of General Virology* 87: 2353-2361, 2006.
Neumann et al., "Hepatitis C Viral Dynamics in Vivo and the Antiviral Efficacy of Interferon-α Therapy," *Science* 282: 103-107, 1998.
NIH Report, "Assessment of Adenoviral Vector Safety and Toxicity: Report of the National Institutes of Health Recombinant DNA Advisory Committee," *Hum. Gene Therap*. 13: 3-13, 2002.
Pickles et al., "Retargeting the Coxsackievirus and Adenovirus Receptor to the Apical Surface of Polarized Epithelial Cells Reveals the Glycocalyx as a Barrier to Adenovirus-Mediated Gene Transfer," *J. Virol*. 74: 6050-6057, 2000.
Pickles et al., "Utility of Adenoviral Vectors in Animal Models of Human Disease II: Genetic Disease," Adenoviral Vectors for Gene Therapy, Elsevier Science 565-594, 2002.
Priddy et al, "Safety and Immunogenicity of a Replication-Incompetent Adenovirus Type 5 HIV-1 Clade B gag/pol/nef Vaccine in Healthy Adults," *Clin. Infect. Dis*. 46: 1769-1781, 2008.
Reid et al, "Intra-arterial administration of a replication-selective adenovirus (dl1520) in patients with colorectal carcinoma metastatic to the liver: a phase I trial," *Gene Therapy* 8(21): 1618-1626, 2001.
Sadler et al., "Interferon-inducible antiviral effectors," *Nat. Rev. Immunol*. 8: 559-568, 2008.
Smee et al., "Therapy and Long-Term Prophylaxis of Vaccinia Virus Respiratory Infections in Mice with an Adenovirus-Vectored Interferon Alpha (mDEF201)," *PloS One* 6: e26330, 2011.
Sumida et al. "Neutralizing Antibodies to Adenovirus Serotype 5 Vaccine Vectors Are Directed Primarily against the Adenovirus Hexon Protein," *J. Immunol*. 174: 7179-7185, 2005.
Thomas et al., "Progress and problems with the use of viral vectors for gene therapy," *Nat. Rev. Gen*. 4: 346-358, 2003.
Tsai et al., "Alphaviruses," *Clinical Virology* 2: 1177-1210, 2002.

Tsugawa et al., "Sequential delivery of interferon-α gene and DCs to intracranial gliomas promotes an effective antitumor response," *Gene Therapy* 11: 1551-1558, (2004).

Walters et al., "Basolateral localization of fiber receptors limits adenovirus infection from the apical surface of airway epithelia," *J. Biol. Chem.* 274: 10219-10226, 1999.

Wesley and Lager, "Overcoming maternal antibody interference by vaccination with human adenovirus 5 recombinant viruses expressing the hemagglutinin and the nucleoprotein of swine influenza virus," *Vet. Microbiol.* 118: 67-75, 2006 (Abstract Only).

Wu et al., "Adenovirus-mediated type I interferon expression delays and reduces disease signs in cattle challenged with foot-and-mouth disease virus." *J. Interferon Cytokine Res.* 23: 359-368, 2003 (Abstract Only).

Zuckerman et al., "A Phase I Study of Adenovirus-Mediated Transfer of the Human Cystic Fibrosis Transmembrane Conductance Regulator Gene to a Lung Segment of Individuals with Cystic Fibrosis," *Human Gene Therapy* 10: 2973-2985, 2004.

Office Action, U.S. Appl. No. 12/545,933, dated Feb. 8, 2012 (12 pages).

Reply to Office Action, U.S. Appl. No. 12/545,933, dated Jul. 9, 2012 (16 pages).

Supplemental Reply to Office Action, U.S. Appl. No. 12/545,933, dated Aug. 15, 2012 (7 pages).

Declaration of Jeffrey D. Turner, U.S. Appl. No. 12/545,933, dated Jul. 9, 2012 (6 pages).

\* cited by examiner

Figure 1

Figure 2 conINF-α

Figure 5

| Viral Family | Virus | No. Groups; Number/Group | Formulation(s); Dilution level(s) | Treatment Route; Volume; Schedule | Challenge Route; Level; Schedule | Significant Findings |
|---|---|---|---|---|---|---|
| Arenavirus | Pichinde | 10; Syrian Hamsters | Liquid DEF201; $10^8, 10^7, 10^6$ | IN; 100uL; Single dose; -4hr | IP; LD95; Single dose (d0) | 100% Survival Prophylaxis |
| Bunyavirus | Punta Toro | 10; Syrian hamsters | Liquid DEF201; $10^8, 10^7,$ or $10^6$ PFU/animal | IN; 100uL; Single dose; -4hr | IN; LD95; Single dose (d0) | 100% Survival Prophylaxis |
| Bunyavirus | Punta Toro | 10; 10 Balb/c/group | Liquid mDEF201; $5 \times 10^5$ PFU/animal | IN; 50uL; Single dose; -21, -14, -7, or -1d | IN; LD95; Single dose (d0) | Significant reduction in viral titers & serum ALT |
| Coronavirus | SARS | 4; 10 Balb/c/group | Liquid mDEF201; $10^6$ or $10^5$ PFU/animal | IN; 50uL; Single dose; -24hr | IN; LD95; Single dose (d0) | 100% Survival Prophylaxis |
| Coronavirus | SARS | 5; 10 Balb/c/group | Liquid mDEF201; $10^6$ or $10^5$ PFU/animal | IN; 50uL; Single dose; +6, 12, or 24hr | IN; LD95; Single dose (d0) | 90% Treatment Survival |
| Flavivirus | Yellow Fever | 15-20 Syrian Hamsters | Liquid DEF201; $108, 5\times10^7, 5\times10^6, 5\times10^5$ PFU/animal | IN; 100uL; Single dose; -4hr | IP; 10 $CCID_{50}$; Single dose (d0) | 100% Survival Prophylaxis |
| Flavivirus | Yellow Fever | 15-20 Syrian Hamsters | Liquid DEF201; $5\times10^7$ PFU/animal | IN; 100uL; Single dose; +1d, +2d or +3d | IP; 10 $CCID_{50}$; Single dose (d0) | 100% Treatment Survival |
| Filovirus | Ebola – Zaire | 3; 10 B10.BR/group | Liquid mDEF201; $10^7$ PFU/animal | IN or IM; 50uL; Single dose; +30min | IP; 1000LD50; Single dose (d0) | 100% Treatment Survival |
| Filovirus | Ebola – Zaire | 5; 3 Hartley Guinea pigs/group | Liquid mDEF201; $2\times10^8$ PFU/animal | IN or IM; 250uL; Single dose; +30min | IP; 100LD50; Single dose (d0) | 100% Treatment Survival |
| Togavirus | WEE | 5; 10 Balb/c/group | Liquid mDEF201; $10^7$ PFU/animal | IN; 50uL; Single dose; d -21, -14, -7, or -1 | IN; 43LD50 Single dose (d0) | 100% Survival Prophylaxis |
| Togavirus | WEE | 3; 10 Balb/c/group | Liquid mDEF201; $10^7$ PFU/animal | IN; 50uL; Single dose; +6h | IN; 43LD50 Single dose (d0) | 100% Treatment Survival |
| Togavirus | VEE | 3; 8 Balb/c/group | Liquid mDEF201; $10^7$ PFU/animal | IM; 50uL; Single dose; -24hr | Sub Q; 10 LD50; Single dose (d0) | 100% Survival Prophylaxis |

DEF201 against WEEV Calif.

- Group 1
- Group 2
- Group 3
- Group 4
- Group 5
- Group 6
- Group 7

B

DEF201 against WEEV CBA87

- Group 1
- Group 2
- Group 3
- Group 4
- Group 5
- Group 6
- Group 7

Figure 8
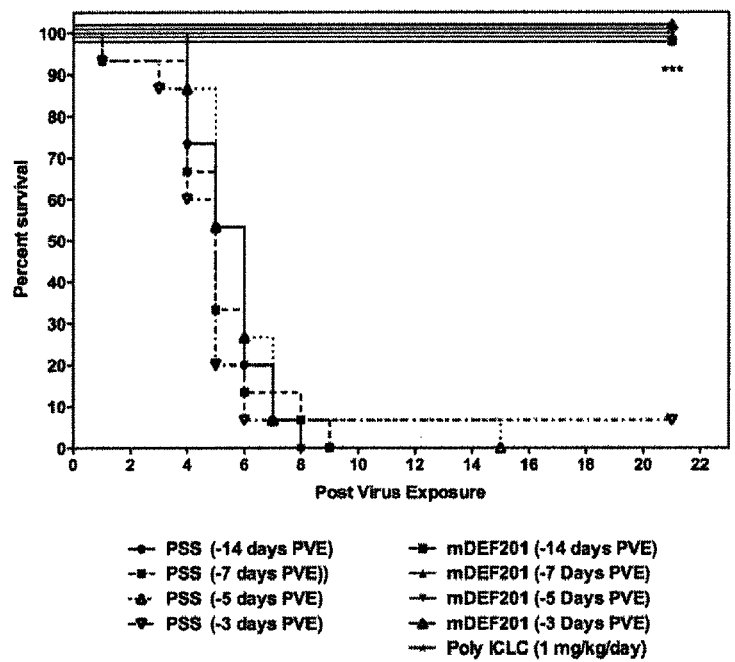
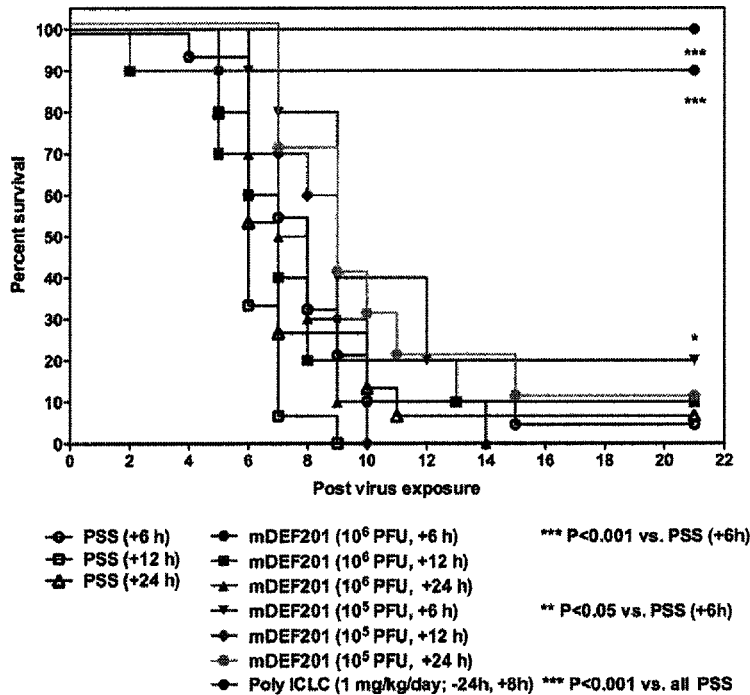

Figure 10
A 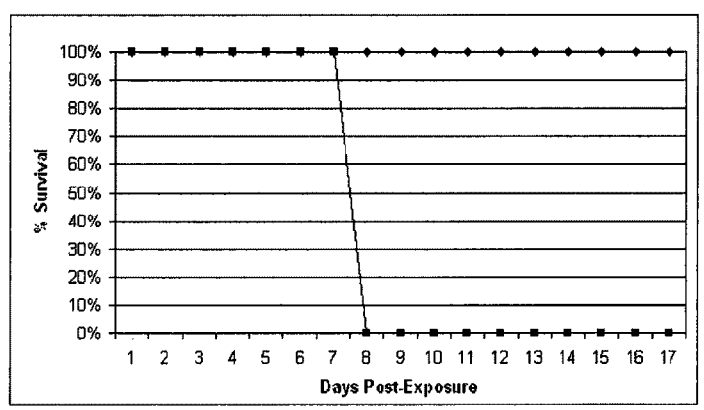
B 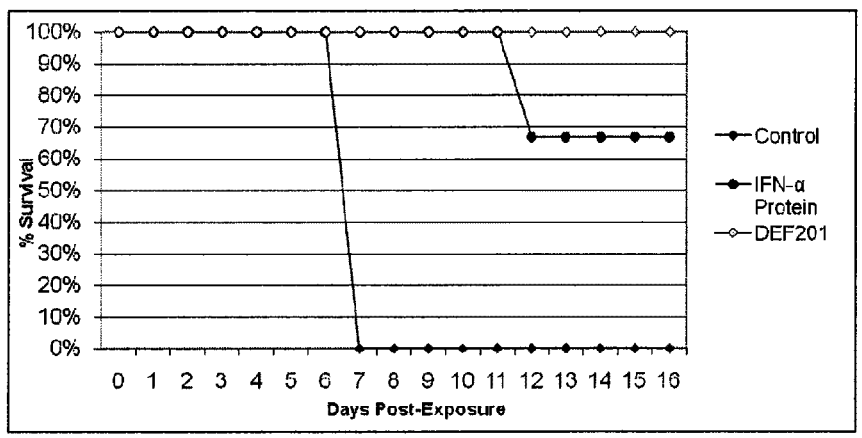

ADMINISTRATION OF INTERFERON FOR PROPHYLAXIS AGAINST OR TREATMENT OF PATHOGENIC INFECTION

CROSS REFERENCE TO RELATED APPLICATIONS

This application claims priority to U.S. Provisional Application No. 61/185,261, filed on Jun. 9, 2009, which is incorporated by reference herein in its entirety.

FIELD OF THE INVENTION

The invention is directed to the treatment of or prophylaxis against diseases or disorders caused by biological or chemical agents in a subject (e.g., a mammal, such as a human).

BACKGROUND OF THE INVENTION

There is a suite of emerging viruses that are endemic, pandemic, engineered, or weaponized. To date, there is no broad-spectrum antiviral therapy that can effectively prevent infection or treat illness resulting from these viruses. According to the U.S. Centers for Disease Control and Prevention (CDC; Rotz et al, CDC Emerging Infectious Diseases Vol. 8, No. 2, 2002) there are six Category A threats, which includes smallpox, which is caused by, e.g., variola virus (Smallpox), and viral hemorrhagic fever, which is caused by, e.g., filoviruses, such as Ebola virus, bunyaviruses, such as hantavirus, and arenaviruses, such as Lassa virus. Category A agents have the greatest potential for adverse public health impact with mass casualties. Biological agents that have potential for large-scale dissemination with resultant illness but generally fewer fatalities are classified as Category B threats. Several viral threats are identified as Category B threats; these include viral encephalitis, such as, e.g., Venezuelan equine encephalitis virus (VEEV), eastern equine encephalitis virus (EEEV), and western equine encephalitis virus (WEEV), which are all alphaviruses. There are also many emerging Category C threats, which include diseases caused by Nipah virus and hantavirus.

In addition to the CDC list, the U.S. Department of Health and Human Services (HHS) has released a list of viruses under their Public Health Emergency Medical Countermeasures Enterprise (PHEMCE) program that lists Arenaviridae (e.g., Junin and Lassa viruses), Filoviridae (e.g., Ebola and Marburg viruses), Poxyiridae (Smallpox and monkey pox viruses), and Orthomyxoviridae (e.g., Influenzavirus A, such as H5N1 and H1N1 viruses). Clearly it is not feasible to vaccinate an entire population against all viral strains of all of these viral agents. Indeed, the large-scale vaccination of the public against bioterrorist threats, e.g., anthrax, was a failure.

Interferon-alpha (IFN-α) has been used clinically and commercially (e.g., RoferonA®, IntronA®, Pegasys®, PegIntron® etc) to successfully treat various cancers, including, e.g., malignant melanoma, hairy cell leukemia, non-Hodgkin's lymphoma, AIDS-related Kaposi's sarcoma, as well as infectious diseases, such as severe acute respiratory syndrome (SARS), chronic Hepatitis B, and chronic Hepatitis C. IFN-α is a type I interferon, which binds to the IFN-α receptor.

IFN-α is one of the earliest cytokines released by antigen presenting cells as part of the innate immune response. It is directly responsible for NK and T cell responsiveness, which drives the subsequent immune response. Because of the early response of IFN-α in the immune cascade, its primary role is suggested to be to induce a priming state during the initial response to infection, and it has been shown that low dose IFN-α results in increased protection from a viral challenge.

IFN-α, as a recombinant human therapeutic agent, is expensive to manufacture by cGMP, is hindered by its short half-life in vivo, and is produced in a non-glycosylated form. IFN-α has an initial distributive half-life of 7 minutes and a beta half-life of 2 to 5 hours. This rapid decay requires multiple injections, usually three times weekly, to maintain therapeutic levels. Thus, at $2,500 per dose retail, the cost of using recombinant human IFN-α as a broad-spectrum antiviral in counter bioterrorism or military operations is prohibitive.

In order to mitigate this rapid in vivo degradation, PEGylated forms of IFN-α have been developed that have half-lives that are on the order of days instead of hours, thus reducing the number of injections to once per week. Nonetheless, the PEGylation process has been shown to reduce the activity of the IFN-α, and PEG-IFN-α is even more expensive to manufacture than IFN-α.

Currently, there is a need for a broad-spectrum antiviral that could be administered for pre- or post-exposure prophylaxis to guard against or in response to, respectively, infectious diseases, such as viral threats (e.g., a viral bioweapon used during a terrorist event or in the event of pandemic disease).

SUMMARY OF THE INVENTION

In a first aspect, the invention features a composition that includes a vector having a nucleic acid molecule encoding an interferon (IFN) and a pharmaceutically acceptable excipient, in which the composition is formulated as a dry, lyophilized powder, gel, or liquid, and in which the composition is stable at room temperature for at least one week. In an embodiment, the interferon is IFN-alpha (IFN-α; e.g., consensus IFN-α (conIFN-α; set forth in, e.g., SEQ ID NO: 11) or that is substantially identical (e.g., at least about 75%, 80%, 85%, 90%, 95%, 97%, or 99% or more identical) to the sequence set forth in SEQ ID NO: 11). In another embodiment, the vector is a viral vector (e.g., an adenoviral vector (e.g., an adenoviral strain 5 (Ad5) vector)). In another embodiment, the adenoviral vector (e.g., the Ad5 vector) includes a deletion of all or part of the E1 and E3 genes, which makes it replication deficient. In yet another embodiment, the vector is a non-viral vector.

In another embodiment of the first aspect of the invention, in vivo expression of the IFN upon administration of the composition of the first aspect of the invention produces a protective immune response against a pathogen (e.g., a bacterium, virus, fungus, or parasite) in a mammal (e.g., a human) to which the composition is administered or treats infection by the pathogen in the mammal. In another embodiment, in vivo expression of the IFN upon administration of the composition of the first aspect of the invention produces a protective response against an autoimmune disease in a mammal (e.g., a human) to which the composition is administered.

In other embodiments of the first aspect of the invention, the nucleic acid molecule of the vector is operably linked to a promoter selected from an SV40 promoter, CMV promoter, adenovirus early and late promoter, metallothioneine gene (MT-1) promoter, Rous sarcoma virus (RSV) promoter, and human Ubiquitine C (UbC) promoter, or the vector further includes one or more of a signal sequence, a polyadenylation sequence, and enhancer, an upstream activation sequence, and a transcription termination factor that facilitates expression of the nucleic acid molecule encoding the interferon. In yet other embodiments, the excipient, which is present in the composition in an amount in the range of from 1% to 90% by weight (e.g., in an amount in the range of from 5% to 30% by weight), is selected from one or more of fructose, maltose, galactose, glucose, D-mannose, sorbose, lactose, sucrose, trehalose, cellobiose, raffinose, melezitose, maltodextrins, dextrans, starches, mannitol, xylitol, xylose, maltitol, lactitol, xylitol sorbitol, sorbitose, pyranosyl sorbitol, myoinositol, glycine, $CaCl_2$, hydroxyectoine, ectoine, gelatin, di-myo-inositol phosphate (DIP), cyclic 2,3 diphosphoglycerate (cDPG), 1,1-di-glycerol phosphate (DGP), β-mannosylglycerate (firoin), β-mannosylglyceramide (firoin A), and proline betaine.

In a preferred embodiment, the excipient is one that is capable of stabilizing the IFN-encoding delivery vehicle (e.g., the Ad5-IFN delivery vehicle) for an extended period of time (e.g., greater than 1 week, and preferably greater than 1 year or more) at room temperature with a loss of less than 20% of the viral titer or biological activity (e.g., if the delivery vehicle is non-viral). Non-limiting examples of such excipients include, e.g., trehalose, sorbitol, sucrose, mannitol, glycine, $CaCl_2$, hydroxiectoin, ectoin, firoin and gelatine.

In still other embodiments, the composition can be formulated for aerosolized delivery; is stable at room temperature for at least one month (e.g., 1 year or more); and can be admixed with a pharmaceutically acceptable liquid to form the liquid or gel.

In a second aspect, the invention features a method for prophylaxis or treatment of infection by a biological agent (e.g., an infectious pathogen, such as a bacteria, virus, fungus, or parasite), autoimmune disease, or cancer in a subject in need thereof (e.g., a mammal, such as a primate, dog, cat, cow, horse, pig, goat, rat, mouse, or human, or a bird) by administering an amount of the composition of the first aspect of the invention to the pulmonary or nasal mucosa of a subject (e.g., a mammal, such as a primate, dog, cat, cow, horse, pig, goat, rat, mouse, or human, or a bird) one or more times (e.g., 2, 3, 4, 5, 6, 7, 8, 9, or 10 times, e.g., within the course of one or more months or one or more years, or as needed). In an embodiment, the vector targets pulmonary or nasal epithelial cells upon said administration. In yet another embodiments, transfection of the vector into the targeted cells results in expression of the interferon (IFN; e.g., IFN-α, such as consensus IFN-α (conIFN-α; set forth in, e.g., SEQ ID NO: 11)) in the cells of the subject and the IFN acts locally and/or is secreted by the cells into the subject's bloodstream. In other embodiments, the composition includes an adenovirus strain 5 (Ad5) vector encoding the IFN and the composition includes the Ad5 vector in an amount in the range of at least about $1 \times 10^3$ to about $1 \times 10^{14}$ viral particles per dose.

In still other embodiments of the second aspect of the invention, the subject receives the composition prior to exposure to the pathogen (e.g., at least about 15 to 30 minutes prior to exposure to the pathogen, preferably at least about 1, 2, 4, 6, 8, 10, 15, 20, or 24 hours prior to exposure to the pathogen, and more preferably at least about 1-2 weeks prior to exposure to the pathogen) or the subject receives the composition following exposure to the pathogen (e.g., immediately after exposure to the pathogen or at least about 15-30 minutes following exposure to the pathogen or at least about 1, 2, 4, 6, 8, 10, 15, 20, 24, 48, or 72 hours, or more, after exposure to the pathogen. In other embodiments, the pathogen is a bacterium, virus, fungus, or parasite.

In other embodiments, the subject receives the composition of the first aspect of the invention prior to or after development of autoimmune disease or cancer, or symptoms thereof.

In still other embodiments of the second aspect of the invention, the composition can be inhaled as a lyophilized powder (e.g., as an unreconstituted powder) or admixed with a pharmaceutically acceptable liquid (e.g., water or saline) and inhaled as an aerosolized mist. In other embodiments, the aerosolized mist includes droplets having a diameter of greater than 2 μm. In yet another embodiment, prior to administration of the composition of the first aspect of the invention, the subject is tested to determine whether the subject has been exposed to the pathogen, exhibits symptoms of autoimmune disease, or has cancer. In another embodiment, following administration of the composition of the first aspect of the invention, the method further includes determining the level of IFN in the subject's serum and administering a subsequent dose of the composition if the level of IFN in the serum is less than about 1000 IU/ml, preferably less than about 500 IU/ml, more preferably less than 100 IU/ml, e.g., in the range of about 0.0001 to about 250 IU/ml. In other embodiments, the level of IFN in the serum, following administration of a composition of the invention is in the range of about 100 IU/ml to about $5.0 \times 10^5$ IU/ml, preferably in the range of about 200 to 10,000 IU/ml, more preferably in the range of about 250 to 5,000 IU/ml. In other embodiments, the subject is administered at least 2 doses (e.g., 3, 4, 5, 6, 7, 8, 9, and 10 doses) of the composition. Preferably, the composition protects the subject from infection by the pathogen for at least about 24 hours, 36 hours, 48 hours, or 72 hours, preferably for at least about 1, 2, 3, 4, or 5 weeks, and more preferably for at least about 2, 6, 12, 18 or 24 months or more. In other embodiments, administration of the composition of the first aspect of the invention reduces or diminishes symptoms associated with autoimmune disease or results in a decrease of 20, 40, 60, 80, or 100% in the size of a tumor or in the number of cancerous cells, as determined using standard methods (for example, at least 20, 40, 60, 80, 90, or 95% of the treated subjects have a complete remission in which all evidence of the tumor or cancer disappears). Desirably, the tumor or cancer does not reappear or reappears after at least 5, 10, 15, or 20 years.

In other embodiments, the composition is administered as a liquid or a gel. The composition may be administered by the subject or by another person, such as an attending physician.

In other embodiments of the second aspect of the invention, following administration of the composition of the first aspect of the invention, the method further includes determining the level of an IFN-induced response as a correlate for the activity of IFN in the subject. For example, the method can include determining or measuring the upregulation or activity of the double-stranded RNA (dsRNA)-dependent protein kinase R (PKR), the 2'-5'-oligoadenylate synthetase (2'-5'-OAS), IFN-inducible Mx proteins, a tryptophan-degrading enzyme (see, e.g., Pfefferkorn, Proc. Natl. Acad. Sci. USA 81:908-912, 1984), adenosine deaminase (ADAR1), IFN-stimulated gene 20 (ISG20), p56, ISG15, mGBP2, GBP-1, the APOBEC proteins, viperin, or other factors (see, e.g., Zhang et al., J. Virol., 81:11246-11255, 2007, and U.S. Pat. No. 7,442,527, which is incorporated by reference herein in its entirety).

A third aspect of the invention features a device that contains the composition of any embodiments of the first aspect of the invention. Preferably, the device includes a) a container that includes the composition; b) a nozzle for directing the composition to the pulmonary or nasal mucosa of a subject; c) a mechanical delivery pump for delivering the composition to the nozzle, such that activation of the pump results in a fluid connection between the nozzle and the container; and d) an actuation mechanism for activating the mechanical delivery pump (e.g., a trigger capable of actuating the delivery pump at a predeterminable pressure or flow rate). The delivery pump can also include a liquid delivery pump for delivering a metered volume of the composition in liquid form or a powder delivery pump for delivering a metered amount of the composition in powder form. In an embodiment, the nozzle can be configured to deliver an aerosol (e.g., a mist) or a jet. Devices for use in the third aspect of the invention are described herein.

A fourth aspect of the invention features a kit that includes a first container having the composition of any embodiments of the first aspect of the invention, a second container having a pharmaceutically acceptable liquid, and the device of any embodiments of the third aspect of the invention, and, optionally, instructions for using the device to deliver the contents of the first container, or for combining the contents of the first and second containers to form a combined composition and then using the device to deliver the combined composition, e.g., to a subject for treating or inhibiting infection by a pathogen, autoimmune disease or symptoms thereof, or cancer. In an embodiment of all aspects of the invention, the vector is a recombinant viral vector (e.g., an adenoviral vector, such as Ad5) that includes a nucleic acid molecule encoding a cytokine (e.g., interferon-alpha (IFN-α), such as consensus IFN-α); the composition can be administered to a subject (e.g., a mammal, such as a primate, dog, cat, cow, horse, pig, goat, rat, mouse, or human, or a bird) to protect against challenge from, or to treat infection by, a biological agent. The biological agent can be an infectious pathogen, such as a bacterium, virus, fungus, or parasite.

In an embodiment of all aspects of the invention, the bacterium is selected from *Pseudomonas aeruginosa, Salmonella typhimurium, Escherichia coli, Klebsiella pneumoniae, Bruscella, Burkholderia mallei, Yersinia pestis*, and *Bacillus anthracis*.

In an embodiment of all aspects of the invention, the virus is selected from a member of the Flaviviridae family (e.g., a member of the *Flavivirus, Pestivirus*, and *Hepacivirus* genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus.

In another embodiment of all aspects of the invention, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Paraná virus, Pichinde virus, Pirital virus, Sabiá virus, Tacaribe virus, Tamiami virus, Whitewater Arroyo virus, Chapare virus, and Lujo virus.

In yet other embodiments of all aspects of the invention, the virus is selected from a member of the Bunyaviridae family (e.g., a member of the *Hantavirus, Nairovirus, Orthobunyavirus*, and *Phlebovirus* genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus.

In still other embodiments of all aspects of the invention, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O' nyong'nyong virus, and the chikungunya virus; a member of the Poxyiridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively).

In still other embodiments of all aspects of the invention, the fungus can be *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*.

In another embodiment of all aspects of the invention, the parasite is selected from *Toxoplasma gondii, Plasmodium falciparum, P. vivax, P. ovale, P. malariae, Trypanosoma* spp., and *Legionella* spp.

In another embodiment of all aspects of the invention, the autoimmune disease includes systemic autoimmune diseases and organ-specific autoimmune diseases. Typical examples of autoimmune diseases include insulin-dependent diabetes (also known as type 1 diabetes), systemic lupus erythematosus, chronic rheumatoid arthritis, Hashimoto's disease, alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, ulcerative colitis, psoriatic arthritis, essential mixed cryoglobulinemia, fibromyalgia-fibromyositis, Graves' disease, Guillain-Barré, hypothyroidism, idiopathic pulmonary fibrosis, idiopathic thrombocytopenia purpura (ITP), IgA nephropathy, juvenile arthritis, lichen planus, lupus, Ménière's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjögren's syndrome, Stiff-Man syndrome, Devic's disease, Takayasu arteritis, temporal arteritis/giant cell arteritis, ulcerative colitis, uveitis, vasculitis, vitiligo, and Wegener's granulomatosis.

In another embodiment of all aspects of the invention, the cancer include such cancers as melanoma, clear cell sarcoma, head and neck cancer, bladder cancer, breast cancer, colon cancer, ovarian cancer, endometrial cancer, gastric cancer, pancreatic cancer, renal cancer, prostate cancer, salivary gland cancer, lung cancer, liver cancer, skin cancer, and brain cancer.

In yet another embodiment of all aspects of the invention, the compositions and methods of the first, second, third, and fourth aspects of the invention further include administering with, or expressing in, the vector (e.g., viral vector), a supplemental therapeutic agent or regimen, e.g., a polypeptide, such as an antibody or antibody fragment (e.g., recombinant, humanized, chimeric, or monoclonal antibody or fragment), a microbial antigen, a cytokine or growth factor, a hormone, a clotting factor, a drug resistance or anti-viral resistance polypeptide, an anti-venom agent, an antioxidant, a receptor or ligand, an immunomodulatory factor, a detectable label, a cellular factor, or a vaccine. In other embodiments, the antibody or antibody fragment can be a single chain antibody (scFv), Fab, Fab'2, scFv, SMIP, diabody, nanobody, aptamer, or domain antibody. In yet other embodiments, the cytokine or growth factor can be tumor necrosis factor alpha (TNF-α), TNF-β, IFN-β, interleukin 1 (IL-1), IL-1β, interleukin 2-14, granulocyte macrophage colony-stimulating factor (GM-CSF), granulocyte colony-stimulating factor (G-CSF), RANTES, MIP-1α), transforming growth factor-beta (TGF-β), platelet derived growth factor (PGDF), insulin-like growth factor (IGF), epidermal growth factor (EGF), vascular endothelial growth factor (VEGF), keratinocyte growth factor (KGF), erythropoietin (EPO), or thrombopoietin (TPO). The hormone can be angiotensinogen, angiotensin, parathyroid hormone (PTH), basic fibroblast growth factor-2, luteinizing hormone, follicle-stimulating hormone, adrenocorticotrophic hormone (ACTH), vasopressin, oxytocin, somatostatin, gastrin, cholecystokinin, leptin, atrial-natriuretic peptide, epinephrine, norephinephrine, dopamine, calcitonin, or insulin. The clotting factor can be factor VII, factor VIII, factor IX, or fibrinogen. The enzyme can be can be butyrylcholinesterase (BChE), adenosine deaminase, glucocerebrosidase, alpha-1 antitrypsin, a viral thymidine kinase, hypoxanthine phosphoribosyl transferase, manganese superoxide dismutase (Mn-SOD), catalase, copper-zinc-superoxide dismutase (CuZn-SOD), extracellular superoxide dismutase (EC-SOD), glutathione reductase, phenylalanine hydroxylase, nitric oxide synthetase, or paraoxinase. The receptor or ligand can be a T-cell receptor (TCR), LDL receptor, surface-bound immunoglobulin, soluble CD4, cystic fibrosis transmembrane conductance receptor (CFTR), or a $F_C$ receptor. The immunomodulatory factor can be CTLA-4, VCP, PLIF, LSF-1, Nip, CD200, uromodulin, CD40L (CD154), FasL, CD27L, CD30L, 4-1BBL, CD28, CD25, B7.1, B7.2, or OX40L. The detectable label can be green fluorescent protein (GFP). The cellular factor can be cytochrome b, ApoE, ApoC, ApoAI, MDR, tissue plasminogen activator (tPA), urokinase, hirudin, β-globin, α-globin, HbA, ras, src, or bcl. The polypeptide can be a cellular protein that acts as an antigen, thereby generating an immune response in the subject against a biological or chemical agent. The vaccine can be, e.g., a bacterial, viral, fungal, or parasite vaccine known in the art for treating one or more of the bacterial, viral, fungal, or parasitic agents described herein. For example, the vaccine may be directed against a bacterium selected from *Pseudomonas aeruginosa, Salmonella typhimurium, Escherichia coli, Klebsiella pneumoniae, Bruscella, Burkholderia mallei, Yersinia pestis*, and *Bacillus anthracis*; a virus selected from a member of the Flaviviridae family (e.g., a member of the *Flavivirus, Pestivirus*, and *Hepacivirus* genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus; a virus selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabiá virus, Tacaribe virus, Tamiami virus, Whitewater Arroyo virus, Chapare virus, and Lujo virus; a virus selected from a member of the Bunyaviridae family (e.g., a member of the *Hantavirus, Nairovirus, Orthobunyavirus*, and *Phlebovirus* genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus; a virus selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxyiridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively); or a fungus selected from *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus,* and *Rhizopus arrhizus*; or parasite selected from *Toxoplasma gondii, Plasmodium falciparum, P. vivax, P. ovale, P. malariae, Trypanosoma* spp., and *Legionella* spp.

In yet other embodiments of all aspects of the invention, the vector (e.g., viral vector) can be modified to express one or more oligonucleotides, e.g., an RNA interference (RNAi) molecule capable of inhibiting viral replication or infection. The RNAi molecule can be a small inhibitory RNA (siRNA) or short hairpin RNA (shRNA) molecule.

In another embodiment of all aspects of the invention, the subject has been or is suspected to have been exposed to a biological or chemical agent prior to receiving a pharmaceutical composition of the invention. In another embodiment of all aspects of the invention, the subject has been diagnosed with or exhibits symptoms of autoimmune disease or cancer prior to receiving a pharmaceutical composition of the invention. The subject can be administered single or multiple doses of the pharmaceutical composition of the invention. In another embodiment of all aspects of the invention, the pharmaceutical composition of the invention can be administered to a subject (e.g., a mammal, such as a human) as a prophylactic, e.g., as a vaccine-type preventative, prior to exposure to a biological or chemical agent to protect the subject (e.g., immediately prior to exposure, e.g., at least about 5, 10, or 30 minutes prior to exposure, or, preferably, at least about 1, 2, 3, 4, or 5 hours prior to exposure, more preferably at least about 6, 24, 36, 48, or 72 hours prior to exposure, and more preferably at least about 1, 2, 3, or 4 weeks or more prior to exposure) or prior to the diagnosis of, or development of symptoms of, autoimmune disease or cancer. The pharmaceutical composition of the invention can be administered to a subject intravenously, intramuscularly, orally, by inhalation, parenterally, intraperitoneally, intraarterially, transdermally, sublingually, nasally, transbuccally, liposomally, adiposally, opthalmically, intraocularly, subcutaneously, intrathecally, topically, or locally. In a preferred embodiment, the pharmaceutical composition is administered to the pulmonary or intranasal mucosa of a subject. If the IFN-encoding delivery vehicle composition is a viral vector, the subject can be administered at least about $1 \times 10^3$ viral particles (vp)/dose or between $1 \times 10^1$ and $1 \times 10^{14}$ vp/dose, preferably between $1 \times 10^3$ and $1 \times 10^{12}$ vp/dose, and more preferably between $1 \times 10^5$ and $1 \times 10^{10}$ vp/dose. If the IFN-encoding delivery vehicle composition is a non-viral vector, the subject can be administered at least about $1 \times 10^1$ molecules/dose, e.g., between $1 \times 10^1$ and $1 \times 10^{15}$ molecules/dose, preferably between $1 \times 10^3$ and $1 \times 10^{10}$ molecules/dose, and more preferably between $1 \times 10^4$ and $1 \times 10^8$ molecules/dose, of the non-viral delivery vector.

In other embodiments of all aspects of the invention, expression of the heterologous protein (e.g., IFN, such as a consensus IFN-α) in a subject (as determined by measuring serum levels) occurs for greater than one week, one month, two months, or six months. In yet other embodiments, the effects of expression of interferon (e.g., IFN-α, such as a consensus IFN-α) occurs for greater than one week, one month, two months, six months or 1-2 years (as determined by using surrogate markers for interferon expression, as is discussed herein).

In another embodiment of all aspects of the invention, the pharmaceutical composition of the invention can be administered to a subject in combination with one or more supplemental agents that enhance or prolong the prophylactic or therapeutic effect of the interferon (e.g., consensus IFN-α) treatment. The supplemental agent can be, e.g., a cytokine, antiviral agent, anti-bacterial agent, anti-fungal agent, anti-parasitic agent, immunostimulant, or immunization vaccine. In another embodiment, the pharmaceutical composition of the invention includes an IFN expression vector (e.g., an Ad5 vector that encodes IFN-α), a vaccine, and a pharmaceutically acceptable carrier, in which the composition is fast-acting (e.g., exhibiting >80% (e.g., 85%, 90%, 95%, or 99% or more (e.g., 100%)) treatment efficacy (e.g., as measured by survival) when administered within at least 24 hours (e.g., 1, 2, 4, 6, 8, 10, 12, 15, or 18 hours) post-exposure or even within as little as 15-30 minutes post-exposure. In another embodiment, the vaccine is a viral vaccine (e.g., an Ebola vaccine (e.g., the Ebola Zaire vaccine Ad-CAGoptZGP; see Richardson et al. (PloS 4:e5308, 2009)). In another embodiment, the pharmaceutical composition of the invention includes an IFN expression vector (e.g., an Ad5 vector that encodes IFN-α) and a pharmaceutically acceptable carrier, which is administered separately or in combination with a vaccine (e.g., a viral vaccine, such as an Ebola vaccine (e.g., the Ebola Zaire vaccine Ad-CAGoptZGP; see Richardson et al. (PLoS 4:e5308, 2009)). For example, the pharmaceutical composition of the invention is administered within 15-30 minutes of the vaccine or within 1, 2, 4, 8, 10, 12, 24, 48, or 72 hours of the vaccine or within 1-2 weeks after the vaccine.

In yet another embodiment of all aspects of the invention, the vector (e.g., viral vector, such as Ad5 vector) is administered with a pharmaceutically acceptable carrier or excipient.

DEFINITIONS

The term "about" is used herein to mean a value that is ±10% of the recited value.

As used herein, by "administering" is meant a method of giving a dosage of a pharmaceutical composition to a subject. The compositions utilized in the methods described herein can be administered by a route selected from, e.g., parenteral, dermal, transdermal, ocular, inhalation, buccal, sublingual, perilingual, nasal, rectal, topical, and oral. Parenteral administration includes intra-arterial, intravenous, intraperitoneal, subcutaneous, and intramuscular administration. The preferred method of administration can vary depending on various factors (e.g., the components of the composition being administered and the severity of the condition being treated).

By "an amount sufficient to treat" is meant the amount of a composition administered to improve, inhibit, or ameliorate a condition of a subject, or a symptom of a disorder, in a clinically relevant manner (e.g., improve, inhibit, or ameliorate infection, e.g., by one or more viruses or viral strains, or one or more symptoms that occur following infection, or to improve, treat, or ameliorate autoimmune disease or cancer, or one or more symptoms thereof). Any improvement in the subject is considered sufficient to achieve treatment. Preferably, an amount sufficient to treat is an amount that reduces, inhibits, or prevents the occurrence or one or more symptoms of a viral infection (e.g., symptoms that result from infection by at least one and preferably two or more viruses or viral strains) or is an amount that reduces the severity of, or the length of time during which a subject suffers from, one or more symptoms of the infection (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the treatment of viral infection(s)) varies depending upon the manner of administration and the age, body weight, and general health of the subject being treated. A physician or researcher can decide the appropriate amount and dosage regimen.

By "host, "subject" or "patient" is meant any organism, such as a mammal (e.g., a primate, dog, cat, cow, horse, pig, goat, rat, and mouse) or a bird; preferably the organism is a human. A host may also be a domestic animal (e.g., a farm animal) or a companion animal (e.g., a pet).

By "inducing an immune response" is meant eliciting a humoral response (e.g., the production of antibodies) or a cellular response (e.g., the activation of T cells, macrophages, neutrophils, and natural killer cells) directed against one or more viruses or viral strains (e.g., two, three, four, or more viruses or viral strains) in a subject to which the pharmaceutical composition (e.g., a vaccine) has been administered.

As used here, "interferon" or "IFN" refers to a peptide or protein having an amino acid sequence substantially identical (e.g., at least 70%, 75%, 80%, 85%, 90%, 95%, 96%, 97%, 98%, 99%, or even 100% identical) to all or a portion of the sequence of an interferon (e.g., a human interferon), such as IFN-α (e.g., IFN-α-1a; see U.S. Patent Application No. 20070274950, incorporated herein by reference in its entirety), IFN-α-1b (SEQ ID NOs: 1 and 2), IFN-α-2a (see PCT Application No. WO 07/044,083, herein incorporated by reference in its entirety) and IFN-α-2b (SEQ ID NOs: 3 and 4)), consensus IFN-α (SEQ ID NO: 11), IFN-β (e.g., described in U.S. Pat. No. 7,238,344, incorporated by reference in its entirety; IFN-β-1a, as described in U.S. Pat. No. 6,962,978; incorporated by reference in its entirety) and IFN-β-1b (as described in U.S. Pat. Nos. 4,588,585; 4,959,314; 4,737,462; and 4,450,103; incorporated by reference in their entirety; see also SEQ ID NOs: 5 and 6), IFN-γ (see, e.g., SEQ ID NOs: 7 and 8), and IFN-τ (as described in U.S. Pat. No. 5,738,845 and U.S. Patent Application Publication Nos. 20040247565 and 20070243163; incorporated by reference in their entirety; see also SEQ ID NOs: 9 and 10).

The term "interferon alpha" or "IFN-α" as used herein means the family of highly homologous species-specific proteins that inhibit viral replication and cellular proliferation and modulate immune response. Typical suitable interferon-alphas include, but are not limited to, recombinant interferon alpha-2a, recombinant interferon alpha-2b, recombinant interferon alpha-2c, alpha 2 interferon, and a consensus alpha interferon, such as those described in U.S. Pat. Nos. 4,897, 471 and 4,695,623 (especially Examples 7, 8 or 9 thereof), which are incorporated herein by reference.

By "pharmaceutical composition" is meant any composition that contains a therapeutically or biologically active agent (e.g., at least one nucleic acid molecule that encodes all or part of a cytokine (e.g., an interferon, such as IFN-α (e.g., consensus IFN-α) either incorporated into a viral vector or independent of a viral vector (e.g., incorporated into a liposome, microparticle, or nanoparticle)) that is suitable for administration to a subject and that is capable of inducing an immune response against at least one virus (e.g., at least two, three, four, or more different viruses or viral strains) or that treats autoimmune disease or cancer or reduces or ameliorates one or more symptoms of autoimmune disease or cancer. For the purposes of this invention, pharmaceutical compositions suitable for delivering a therapeutic or biologically active agent can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, *Remington: The Science and Practice of Pharmacy* (21$^{st}$ ed.), ed. A. R. Gennaro, Lippincott Williams & Wilkins, 2005, and *Encyclopedia of Pharmaceutical Technology*, ed. J. Swarbrick, Informa Healthcare, 2006, each of which is hereby incorporated by reference.

By "pharmaceutically acceptable diluent, excipient, carrier, or adjuvant" is meant a diluent, excipient, carrier, or adjuvant which is physiologically acceptable to the subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art.

By "recombinant," with respect to a vector, such as a viral vector, is meant a vector (e.g., a viral genome that has been incorporated into one or more delivery vehicles (e.g., a plasmid, cosmid, etc.)) that has been manipulated in vitro, e.g., using recombinant nucleic acid techniques, to introduce changes to the vector (e.g., to include heterologous nucleic acid sequences (such as IFN (e.g., conIFN-α) in a viral genome (e.g., a replication deficient Ad5 genome)). An example of a recombinant viral vector of the invention is a vector that includes all or part of the adenovirus (e.g., adenovirus strain 5 (Ad5)) genome and that includes the nucleic acid sequence for all or part of, e.g., a cytokine gene sequence, such as an interferon-$\alpha$ gene (e.g., the consensus IFN-$\alpha$ sequence).

By "room temperature" is meant a temperature of about 5° C. to about 30° C., in particular from about 10° C. to about 27° C. (e.g., about 23-27° C.).

The term "substantial identity" or "substantially identical," when used in the context of comparing a polynucleotide or polypeptide sequence to a reference sequence, means that the polynucleotide or polypeptide sequence has the same sequence as the reference sequence or has a specified percentage of nucleotides or amino acid residues that are the same at the corresponding locations within the reference sequence when the two sequences are optimally aligned. For instance, an amino acid sequence that is "substantially identical" to a reference sequence has at least about 60% identity, preferably 65%, 70%, 75%, 80%, 85%, 90%, 91%, 92%, 93%, 94%, 95%, 96%, 97%, 98%, 99%, or higher percentage identity (up to 100%) to the reference sequence when compared and aligned for maximum correspondence over the full length of the reference sequence as measured using a BLAST or BLAST 2.0 sequence comparison algorithms with default parameters, or by manual alignment and visual inspection (see, e.g., NCBI web site).

By "treating" is meant administering a pharmaceutical composition of the invention for prophylactic and/or therapeutic purposes. Prophylactic treatment may be administered, for example, to a subject who is not yet ill, but who is susceptible to, or otherwise at risk of, a particular biological condition, e.g., infection by a bacteria, virus, fungus, or parasite (e.g., the subject may already have been exposed to the infectious agent but is asymptomatic or the level of exposure to the infectious agent is unknown), or the development of autoimmune disease or cancer. Therapeutic treatment may be administered, for example, to a subject already suffering from contact with a biological agent in order to improve or stabilize the subject's condition (e.g., a patient already infected with a pathogenic virus) or a subject already suffering from an autoimmune disease or cancer. Thus, in the claims and embodiments described herein, treating is the administration to a subject either for therapeutic or prophylactic purposes. In some instances, as compared with an equivalent untreated control, treatment may ameliorate a disorder (e.g., infection by a pathogen, such as a virus, autoimmune disease, and cancer) or a symptom of the disorder, or reduce the progression, severity, or frequency of one or more symptoms of the disorder by, e.g., 5%, 10%, 20%, 30%, 40%, 50%, 60%, 70%, 80%, 90%, 95%, or 100% as measured by any standard technique. For example, for measuring symptoms of infection, one may use, e.g., blood tests to check for antibodies directed against the pathogen or for the antigens themselves; cultures for samples of blood, bodily fluid, or other material taken from the infected area; spinal tap to examine cerebrospinal fluid; polymerase chain reaction (PCR) techniques to amplify nucleic acid material from the pathogen; magnetic and resonance imaging (MRI) to detect increased swelling in the temporal lobes). Symptoms of pathogenic infection, which may vary from mild to severe and may depend on what part of the body is affected, the type of pathogen, and the age and overall health of the affected person, include, e.g., fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death. In some instances, treating can result in the inhibition of the pathogenic infection, the treatment of the infection, and/or the amelioration of symptoms of the infection (e.g., hemorrhagic fever). Detecting an improvement in, or the absence of, one or more symptoms of the infection, indicates successful treatment. Treatment can also be confirmed by the absence of or the inability to detect the presence of, the pathogen (e.g., a virus) in the treated subject.

For the treatment or prophylaxis of autoimmune disease, one can measure, e.g., decreased levels of autoantibodies, decreased levels of autoreactive T cells, increase of targeted cells (e.g., pancreatic $\beta$-islet cells), and improvements in fatigue, depression, sensitivity to cold, weight gain, muscle weakness, constipation, insomnia, irritability, weight loss, bulging eyes, muscle tremors, skin rashes, painful or swollen joints, sensitivity to the sun, loss of coordination, and paralysis.

For the treatment or reduction of cancer, one can measure reductions in the size of a tumor or in the number of cancer cells, the slowing or prevention of an increase in the size of a tumor or cancer cell proliferation, an increase in the disease-free survival time between the disappearance of a tumor or other cancer and its reappearance, the prevention of an initial or subsequent occurrence of a tumor or other cancer, or the reduction of an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of an agent of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

A subject to be treated according to the methods described herein (e.g., a subject infected with, or at risk of being infected with, a bacterium, virus, fungus, or parasite) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been subjected to standard tests or may have been identified, without examination, as one at high risk due to the presence of one or more risk factors (e.g., exposure to a biological agent, such as a virus).

By "viral vector" is meant a composition that includes one or more genes from a viral species, such as an adenoviral species (e.g., Ad5), that is able to transmit one or more heterologous genes from a viral or non-viral source to a host or subject. The nucleic acid material of the viral vector may be encapsulated, e.g., in a lipid membrane or by structural proteins (e.g., capsid proteins), that may include one or more viral polypeptides (e.g., a glycoprotein). The viral vector can be used to infect cells of a subject (e.g., nasal epithelium), which, in turn, promotes the translation of the heterologous gene(s) of the viral vector into a protein product (e.g., IFN-α).

Alternatively, the viral vector can be administered to a subject so that it infects one or more cells of the subject, which then promotes expression of the one or more heterologous genes of the viral vector and stimulates an immune response (directly or indirectly) that is protective against infection by a pathogen (e.g., bacteria, virus, fungus, or parasite) or that treats infection by the pathogen.

The term "vaccine," as used herein, is defined as material used to provoke an immune response and confer immunity after administration of the vaccine to a subject.

The term "virus," as used herein, is defined as an infectious agent that is unable to grow or reproduce outside a host cell and that infects mammals (e.g., humans) or birds.

Other features and advantages of the invention will be apparent from the detailed description and from the claims.

BRIEF DESCRIPTION OF THE FIGURES

FIG. 1 is a table providing comparative amino acid sequences (SEQ ID NOs: 11-24) of human leukocyte interferon subtypes and a consensus human leukocyte interferon.

FIG. 2 is a schematic showing insertion of the nucleic acid molecule encoding consensus interferon-alpha (conINF-α) into an adenoviral vector.

FIG. 5 is a table summarizing the results of experiments (in the indicated animal model) using compositions of the invention to treat or prevent infection by the indicated virus.

FIGS. 7A and 7B are graphs showing the effect of IN Ad5-IFNα treatment on survival outcome in mice challenged with WEE virus. Animals in each group were treated with $10^7$ PFU Ad5-IFNα, as per the groups outlined in Example 9 below, and challenged with WEE virus via IN instillation. IFNα B/D was given daily as a positive control group.

FIGS. 8A and 8B are graphs showing the effect of IN Ad5-IFNα treatment on survival outcome in mice challenged with SARS virus. FIG. 8A shows the results of prophylaxis: Animals in each group were treated with $10^6$ PFU Ad5-IFNα, as per the groups outlined in Example 10 below, and challenged with SARS virus via IN instillation. FIG. 8B shows the results of treatment: Animals in each group were treated with $10^6$ or $10^5$ PFU Ad5-IFNα as per the groups outlined in Example 10 below, and challenged with SARS virus via IN instillation Poly IC/LC was used as a positive control group, with saline as negative control.

FIG. 9A shows the results of dose range prophylaxis: Animals were treated with Ad5-IFNα as per the groups outlined in Example 11 below, and challenged with YF virus via IN instillation. Complete protection was observed at the two highest doses, with a dose response curve for the lower doses. FIG. 9B shows the results of treatment: Animals in each group were treated with $5×10^7$ PFU Ad5-IFNα, as per the groups outlined in Example 11 below, and challenged with SARS virus via IN instillation Complete survival was observed for the −4 hr and +1 dpi groups with a drop in survival correlated with delayed treatment in other groups.

FIGS. 10A and 10B are graphs showing the effect of IN Ad5-IFNα treatment on survival outcome in mice challenged with ZEBOV. FIG. 10A shows the results of mouse treatment: Animals were challenged with 100 LD50 EBOV and 30 minutes later treated with Ad5-IFNα by either the IM or IN route. Complete protection was observed with $10^7$ PFU with both routes of administration. FIG. 10B shows the results of guinea pig treatment: Animals were challenged with 100 LD50 EBOV and 30 minutes later treated with Ad5-IFNα IN. Complete protection was observed with $2×10^8$ PFU.

DETAILED DESCRIPTION OF THE INVENTION

Figure 3:
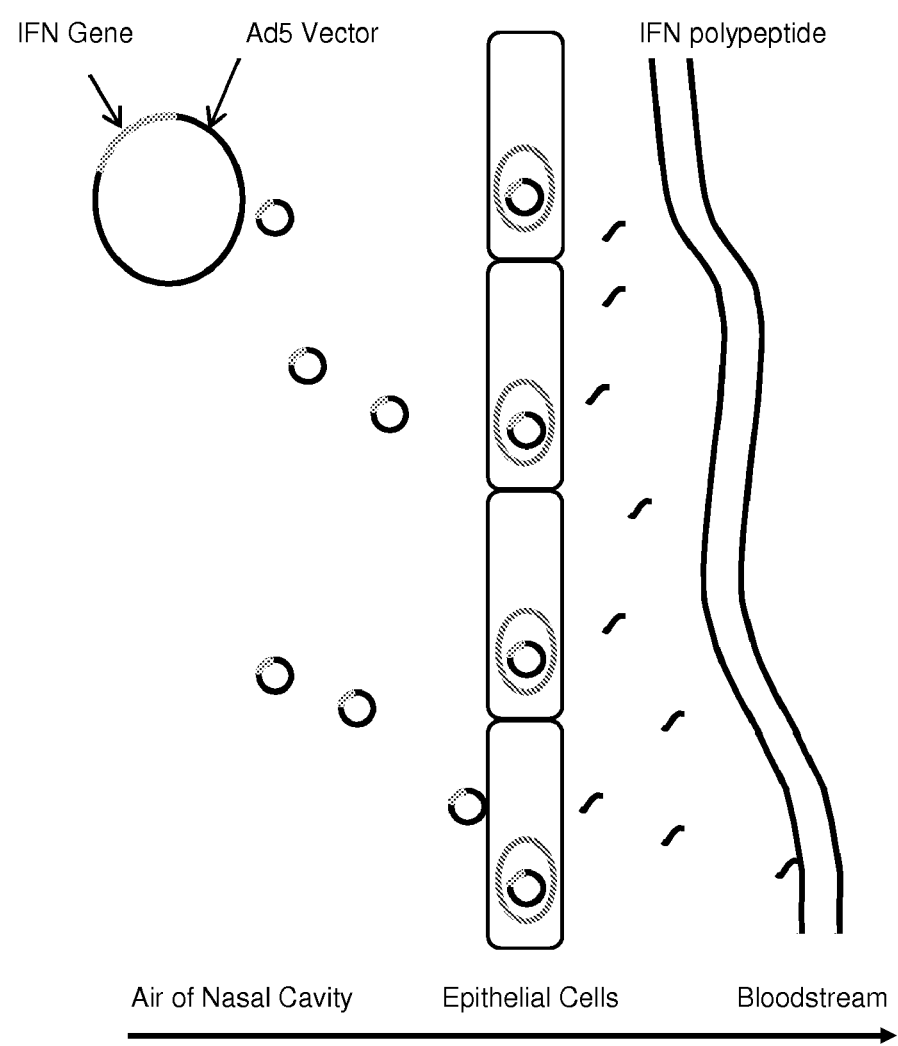
FIG. 3 is a schematic showing delivery of an Ad5-con-IFN-α construct of the invention to the nasal epithelial cells of a patient, expression of the conIFN-α nucleic acid molecule in the cells, and release of IFN polypeptide into the bloodstream of the patient.

The invention features compositions and methods for the prophylaxis (pre- or post-exposure) and treatment of diseases or disorders caused by an infectious pathogen (e.g., infectious agents, such as viruses, bacteria, fungi, and parasites) in a subject (e.g., a mammal, such as a human). The infectious pathogen may be naturally occurring or it may be formulated for, or adapted to, use as a biological agent. The invention also features the use of the compositions of the invention to treat or reduce one or more symptoms of autoimmune disease and cancer in a subject (e.g., a mammal, such as a human).

The compositions of the invention can be used as, e.g., a broad-spectrum prophylaxis or treatment to guard against or treat infection by several different infectious pathogens, in particular, viral agents. Of particular note, the compositions of the invention can be administered for pre-exposure prophylaxis (e.g., 1-30 minutes (e.g., 15-30 minutes) before exposure, preferably 1, 2, 3, 4, 5, 6-12, 24-72 hours before exposure, or 1-6 weeks or more (e.g., at least 2 weeks) before exposure to an infectious agent), as well as for post-exposure prophylaxis or treatment (e.g., immediately after exposure, e.g., 1-30 minutes (e.g., 15-30 minutes) after exposure, or within 1, 2, 3, 4, 5, 6-12, 24, 48, or 72 hours or 1-2 weeks after exposure to an infectious agent). Thus, the compositions of the invention provide benefits in the prophylaxis or treatment, respectively, of a subject in anticipation of, or following, e.g., exposure to an infectious pathogen (e.g., a virus, such as during a bioterrorist attack). The benefits include both long-lasting protection as well as rapid protection, as needed.

In order to circumvent the fast decay of traditional IFN-α protein-based drugs in vivo, the compositions of the invention utilize a delivery vector (e.g., a viral vector, such as an adenoviral vector (e.g., an adenovirus 5 (Ad5) delivery platform)) that is capable of delivering a nucleic acid molecule encoding IFN, which drives the continuous in situ production of IFN (e.g., human IFN-α, such as consensus IFN-α (con IFN-α)) by cells transduced or transfected with the delivery vector. The production of IFN continues in the transduced or transfected cell (e.g., for the life of the cell).

For example, a nucleic acid molecule encoding IFN-α is inserted into the replication defective Ad5 virus, and the Ad5-IFN-α vector is then delivered to a subject (e.g., a mammal, such as a human). In an embodiment, delivery of the viral vector is intranasal. Intranasal administration of the compositions of the invention prevents the host immune system from recognizing the Ad5 vector, thereby bypassing any pre-existing immunity the subject might typically present against the delivery vector itself. In addition, intranasal administration avoids the use of needles, which allows for easier, less invasive administration in the event mass administration to the public is needed in response to, e.g., a bioterrorist attack, or in the absence of ready access to a medical facility. Compositions of the invention can also be delivered to the pulmonary system (e.g., the upper and/or lower respiratory tract) by delivery to the lungs through the mouth.

The compositions of the invention also provide benefit due to their long-term storage potential and extended shelf life. The compositions of the invention can be stored at room temperature for significant periods of time (e.g., for at least 1 week and up to 1 year or more). Alternatively, the compositions of the invention can be stored at temperatures in the range of 30°-55° C. (e.g., at 45° C.) for significant periods of time (e.g., for at least 2-3 days, 1-3 week, 1-6 months, and up to 1 year or more). In an embodiment, the compositions of the invention are in powder form when stored at temperatures in the range of 30°-55° C. In yet other embodiments, the compositions of the invention can be stored frozen (e.g., at temperatures below at least 4° C. (e.g., in the range of 0° to −20° C.)), either in a powder or liquid form. For example, the compositions can be stored frozen as a non-stabilized, liquid formulation (e.g., without any or with only one or a few stabilizing agents, such as, e.g., trehalose, sorbitol, sucrose, mannitol, glycine, $CaCl_2$, hydroxiectoin, ectoin, firoin and gelatin).

In an embodiment, the compositions of the invention are stored as a stable lyophilized powder. The powder can be used directly (e.g., in powder form without reconstitution of any kind) or reconstituted just before use (e.g., using a hydration medium, such as saline or water, preferably sterilized, or any other pharmaceutically acceptable hydration medium) and administered as, e.g., an aqueous mist. Reconstitution of powder forms of the compositions of the invention is possible where clean water is available, such as a medical facility or rear echelons in the military. Alternatively, the powder compositions of the invention can be reconstituted in a gel form. Nasal gels are high-viscosity thickened solutions or suspensions. The advantages of a nasal gel includes the reduction of post-nasal drip due to high viscosity, reduction of taste impact due to reduced swallowing, reduction of anterior leakage of the formulation, reduction of irritation by using soothing/emollient excipients, and target to mucosa for better absorption.

The powder form of compositions of the invention can be provided in a kit with a vial of sterile hydrating medium (e.g., water or saline) that can be used to reconstitute the powder (e.g., to form a liquid or gel). If water is to be used as the hydrating medium, the composition of the invention can but need not be formulated to include reagents (e.g., buffers) that adjust the conditions of the composition in its final form (e.g., the pH, osmolarity, or ionic concentration) so that it is suitable for, or tolerable to, a subject administered the composition.

Administration of the compositions of the invention in powder form is more likely in, e.g., emerging economies, expeditionary military operations, and in rapid response situations. For those compositions of the invention that are not formulated to exhibit an extended shelf life at room temperature or at higher temperatures (e.g., those compositions of the invention that exhibit a shelf life of less than 1 week when stored at room temperature), it is preferable that the compositions be stored at a temperature in the range of about −20° C. to about 20° C. to extend shelf life. These compositions may be formulated with an excipient that does not stabilize the Ad5-IFN delivery vehicle such that it can only remain at room temperature for periods of less than, e.g., 1 week to 1 month, unless refrigerated.

Compositions of the invention (e.g., an Ad5-IFNα construct) have been tested successfully to date in animal models of human disease, such as mouse, Guinea pig, and hamster models, against challenges from representative viruses from important viral families, e.g., Filoviridae (Ebola virus, Zaire strain), Flaviviridae (Yellow Fever), Arenaviridae (Pichinde), Bunyaviridae (Punta Toro), Coronaviridae (SARS), Togaviridae (VEEV and WEEV); see FIG. 5. The compositions of the invention have an excellent treatment profile and a good prophylactic window with data indicating full protection to 21 days with partial protection at further time points. Compositions of the invention are fast acting, and impart both therapeutic and prophylactic benefits to the recipient within minutes to hours; the benefits of the compositions of the invention remain effective for days and even months after administration.

Compositions of the Invention

The compositions of the invention include a delivery vector containing a nucleic acid molecule encoding a cytokine (e.g., an IFN, such as conIFN-α). The compositions of the invention may be formulated for any route of administration (e.g., the administration routes described herein, such as by nasal inhalation and/or inhalation through the mouth for delivery to the upper and/or lower respiratory tract). The compositions may be administered in a single dose or in multiple doses to a subject in need thereof, either pre- or post-exposure to an infectious pathogen or prior to the diagnosis of, or after development of symptoms of, autoimmune disease or cancer. The compositions of the invention may also further include secondary agents (either as a nucleic acid molecule to be expressed by a cell of the subject or as a polypeptide or drug) or they may be administered in combination with one or more additional therapeutic regimens (e.g., vaccines), as is discussed below.

Interferons

Figure 1:
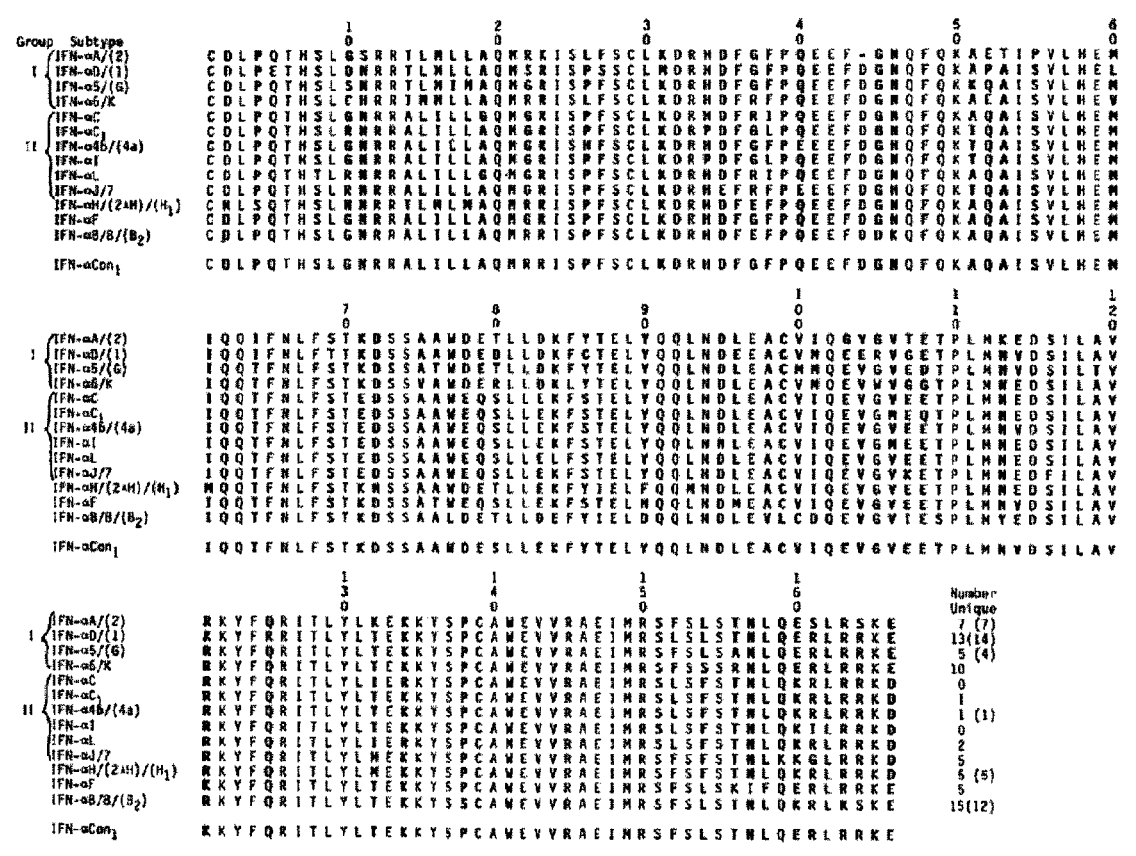

The compositions of the invention for use in the pre- or post-exposure prophylaxis or treatment, respectively, of a pathogenic infection (e.g., a viral, bacterial, fungal, or parasitic infection) or for use in the treatment of autoimmune disease or cancer (or one or more symptoms thereof) include a delivery vector containing a nucleic acid molecule encoding an IFN. The nucleic acid molecule encodes an interferon having an amino acid sequence substantially identical (e.g., at least 70%, 75%, 80%, 85%, 90%, 95%, 96%, 97%, 98%, 99%, or even 100% identical) to the sequence of a human IFN-α (e.g., IFN-α-1a, IFN-α-1b, IFN-α-2a, IFN-α-2b, and consensus IFN-α (conIFN-α); FIG. 1), a human IFN-β (e.g., IFN-β-1a and IFN-β-1b), a human IFN-γ), or an IFN-τ or a polypeptide that demonstrates the same or similar biological activity to an interferon (e.g., at least 50%, 60%, 70%, 75%, 80%, 85%, 90%, 95%, or 100% of the activity of a human IFN-α, a human IFN-β, a human IFN-γ, an IFN-τ, or a conIFN-α (SEQ ID NOs: 2, 4, 6, 8, 10, and 11, respectively). The nucleic acid molecule may have the sequence set forth in any one of SEQ ID NOs: 1, 3, 5, 7, or 9 corresponding to a human IFN-α, a human IFN-β, a human IFN-γ, or an IFN-τ, respectively, or the nucleic acid molecule may have a sequence having at least 70%, 75%, 80%, 85%, 90%, 95%, 96%, 97%, 98%, 99%, or even 100% identity to one of SEQ ID NOs: 1, 3, 5, 7, or 9.

The biological activity of an interferon of the invention can be confirmed using, e.g., a virus-plaque-reduction assay, assays that measure the inhibition of cell proliferation, the regulation of functional cellular activities, the regulation of cellular differentiation, and immunomodulation mediated by IFN, as well as a reporter gene assay, in which the promoter region of IFN responsive genes is linked with a heterologous reporter gene, for example, firefly luciferase or alkaline phosphatase, and transfected into an IFN-sensitive cell line such that stably transfected cell lines exposed to IFN increase expression of the reporter gene product in direct relation to the dose of IFN (see, e.g., Balducci et al., Appl. Microbiol. 11:310-314, 1963; McNeil, J. Immunol. Methods 46:121-127, 1981; and Meager et al., J. Immunol. Methods 261:21-36, 2002). Other assays for measuring the activity of IFN include measuring the upregulation or activity of the double-stranded RNA (dsRNA)-dependent protein kinase R (PKR), the 2'-5'-oligoadenylate synthetase (2'-5'-OAS), IFN-inducible Mx proteins, a tryptophan-degrading enzyme (see, e.g., Pfefferkorn, Proc. Natl. Acad. Sci. USA 81:908-912, 1984), adenosine deaminase (ADAR1), IFN-stimulated gene 20 (ISG20), p56, ISG15, mGBP2, GBP-1, the APOBEC proteins, viperin, or other factors (see, e.g., Zhang et al., J. Virol., 81:11246-11255, 2007, and U.S. Pat. No. 7,442,527, which is incorporated by reference herein in its entirety).

Interferon alpha (IFN-α), as used herein, refers to a cytokine with multiple biological activities that include antiviral activity, regulation of cell proliferation and differentiation and immunomodulation, as exemplified in, e.g., Pfeffer et al. (Cancer Res. 58:2489-2499, 1998). In an embodiment of the invention, the IFN-α may be selected from, e.g., IFN-α2a, IFN-α2b, IFN-α2c, and consensus IFN-α (conIFN-α) (see FIG. 4 and, e.g., U.S. Pat. No. 4,695,623, incorporated herein by reference). In an embodiment, the IFN-α is conIFN-α.

Unlike the compositions of the invention, recombinant human IFN, in particular rhconIFN-α, which is fully approved and marketed as Infergen® for the treatment of chronic Hepatitis C, is made via prokaryotic fermentation, and thus lacks glycosylation. Moreover, Infergen® is formulated for administration via injection into patients.

Viral Vectors

Figure 2:
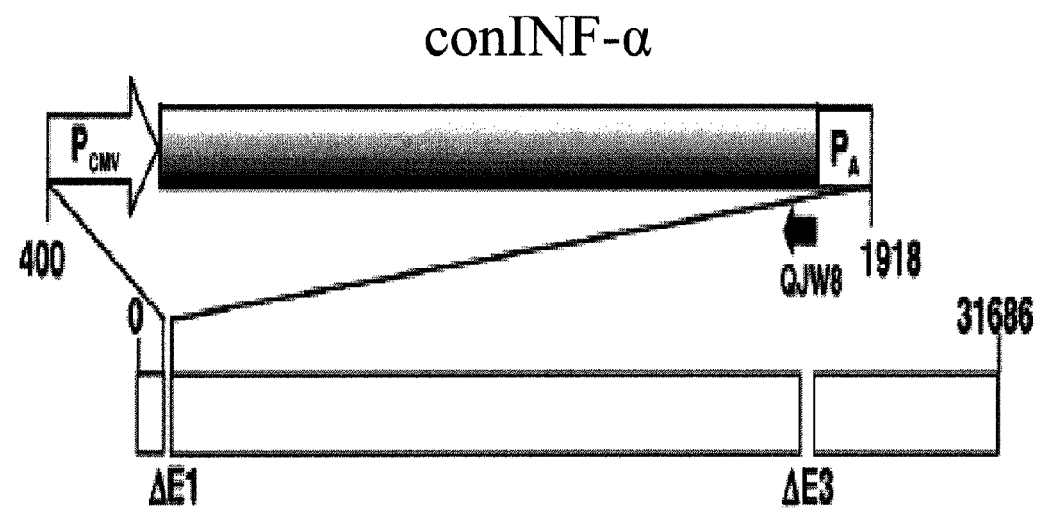

In the invention described herein, the interferon (e.g., IFN-α, such as conIFN-α) can be formulated for delivery using a viral vector that includes a nucleic acid molecule encoding the interferon. Any suitable viral vector system can be used including, e.g., adenoviruses (e.g., Ad2, Ad5, Ad9, Ad15, Ad17, Ad19, Ad20, Ad22, Ad26, Ad27, Ad28, Ad30, or Ad39; see, e.g., FIG. 2), rhabdoviruses (e.g., vesicular stomatitis virus), retroviruses (see, e.g., Miller, Curr. Top. Microbiol. Immunol. 158:1-24, 1992; Salmons and Gunzburg, Human Gene Therapy 4:129-141, 1993; and Miller et al., Methods in Enzymology 217:581-599, 1994), adeno-associated vectors (reviewed in Carter, Curr. Opinion Biotech. 3:533-539, 1992; and Muzcyzka, Curr. Top. Microbiol. Immunol. 158:97-129, 1992), poxviruses, herpes viral vectors, and Sindbis viral vectors (see viral vectors discussed generally in, e.g., Jolly, Cancer Gene Therapy 1:51-64, 1994; Latchman, Molec. Biotechnol. 2:179-195, 1994; Johanning et al., Nucl. Acids Res. 23:1495-1501, 1995; Berencsi et al., J. Infect. Dis. 183:1171-1179, 2001; Rosenwirth et al., Vaccine 19:1661-1670, 2001; Kittlesen et al., J. Immunol. 164:4204-4211, 2000; Brown et al., Gene Ther. 7:1680-1689, 2000; Kanesa-thasan et al., Vaccine 19:483-491, 2000; and Sten Drug 60:249-271, 2000. Compositions comprising such vectors and an acceptable excipient are also a feature of the invention.

Ad5 is a virus of the family Adenoviridae, species C, subtype 5. This virus is naturally occurring and causes mild upper respiratory infections, usually in children. Ad5 can be used as a delivery platform to deliver the genetic information to make human interferon in situ. Typically, the Ad5 is rendered replication defective (by specific gene deletion; e.g., all or a portion of the E1 or E3 genes). Ad5 vectored vaccines have been approved for clinical studies widely in the past. Ad5 is widely used in clinical trials as a vector delivery system. As of June 2010, there are currently 29 clinical trials that are currently active using Ad5 vectored delivery of biologics/drugs. Adenovirus 5 based vectors exhibit an excellent safety profile. The Ad5 vector has additional benefits over conventional vaccines such as live-attenuated vaccines, a type of vaccine where pathogenic viruses are partially crippled via chemical or heat treatment prior to injection, in that there is no risk the Ad5 system could revert and cause illness. Further, Ad5 is a live vaccine which has been shown to provide prompt immunologic protection. Ad5-based vectors for delivery of cytokine genes for providing protection against biological weapons is described in, e.g., U.S. Pat. Nos. 6,565,853 and 6,936,257, both of which are incorporated herein by reference.

Intravenous or intramuscular administration of agents for biodefense medical counter measure indications using the Ad5 system have previously failed because the body's immune system recognizes this viral vector and destroys the vector before the gene has been delivered to a host cell. This occurred most recently with Merck's HIV-1 vaccine clinical trial, which resulted in the study being halted early on the grounds of futility (see Robb, Lancet 372, 2008). Intranasal administration of compositions of the invention (e.g., an Ad5-vector encoding IFN) circumvents this problem by avoiding the body's immune targeting of the Ad5 vector, as is discussed herein.

The viral vector may be constructed using conventional techniques known to one of skill in the art. For example, the viral vector may contain at least one sequence encoding a heterologous gene (e.g., consensus IFN-α), which is under the control of regulatory sequences that direct its expression in a cell (e.g., an epithelial cells, such as a nasal or pulmonary epithelial cell). Appropriate amounts for vector-mediated delivery of the heterologous gene can be readily determined by one of skill in the art based on the information provided herein.

The delivery of IFN-α using an adenoviral vector is described in, e.g., Ahmed et al. (J. Interferon Cytokine Res. 21: 399408, 2001), Zhang et al. (Proc. Natl. Acad. Sci. USA 93:4513-4518, 1996), Ahmed (Hum. Gene Ther. 10:77-84, 1999), and Santodonato et al. (Cancer Gene Ther. 8:63-72, 2001). The delivery of IFN-α using a retroviral vector is described in, e.g., Tuting et al. (Gene Ther. 4:1053-1060, 1997) and Mecchia et al. (Gene Ther. 7:167-179, 2000).

In an embodiment, the Ad5 vector contains a nucleic acid molecule encoding human interferon alpha consensus sequence under the transcriptional regulation of the intermediate-early promoter of CMV and Simian virus 40 (SV40) polyadenylation sequence. In another embodiment, the human Ad5 vector includes E1 and E3 deletions to render it replication deficient. The Ad5-IFN-α vector can be further stabilized with an excipient of polysaccharides and electrolytes during lyophilization and storage, as is described herein. As adenoviruses are fragile to thermal stress and maintenance of the cold chain in the field is onerous, the temperature stability of the compositions of the invention impart a significant advantage. We have developed a systematic process for the stabilization of viral-based vaccines, including adenoviruses, based on a novel eigenvector approach (see, e.g., Kueltzo et al., J. Pharm. Sci. 92:1805-1820, 2003; Fan et al., J. Pharm. Sci. 94:1893-1911, 2005; Ausar et al., Mol. Pharm. 2:491-499, 2005; and Rexroad et al., J. Pharm. Sci. 95:237-247, 2005). Multiple assays are then used to identify a number of potential excipients that are tested for their ability to stabilize the virus against physical and chemical degradation pathways that result in loss of activity (e.g. physicochemical integrity, biological activity, etc.).

An increase in the expression level of a transfected nucleic acid molecule (e.g., the con IFN-α sequence) in a host cell (e.g., an epithelial cell, such as a nasal or pulmonary epithelial cell) can be promoted by operably linking the nucleic acid molecule to an open frame expression control sequence, which can work in the selected expression host. Expression control sequences useful for eukaryotic host cells can be a native or foreign to the nucleic acid molecule to be expressed, as well as to the delivery vector. Examples of expression control sequences include, but are not limited to, leader sequences, polyadenylation sequences, propeptide sequences, promoters, enhancers, upstream activation sequences, signal peptide sequences, and transcription termination factors. Expression control sequences include those derived from, e.g., SV40 (e.g., early and late promoters of SV40), bovine papilloma virus, adenovirus (e.g., early and late promoters of adenovirus), cytomegalovirus (CMV; e.g., the human cytomegalovirus early gene promoter), MT-1 (metallothioneine gene) promoter, Rous sarcoma virus (RSV) promoter, and human Ubiquitine C (UbC) promoter. In order to further improve expression in mammalian cells, synthetic intron sequences can be inserted into a non-transcription region of a nucleotide sequence encoding the IFN-α polypeptide.

Other vector components that can be used in practicing the present invention include a signal peptide. This sequence is typically located at the 5' of a gene encoding a protein and is thus added to the amino terminus of the protein during expression. The presence or absence of a signal peptide varies depending on the expression host cell to be used in production of the IFN-α polypeptide and the preference of producing a secreted product (i.e., according to whether the IFN-α polypeptide is to be expressed intra-cellularly or extra-cellularly). In an embodiment, the IFN-α (e.g., the conIFN-α) is secreted from the host cell during expression. The signal peptide can be homologous or heterologous to either the IFN-α polypeptide or the host cell.

A nucleic acid molecule is "operably linked" to another nucleic acid molecule when they are arranged in a functional relationship. This means that an appropriate molecule (for example, a transcription activator) binds to a regulatory sequence(s), a gene, or a regulatory sequence (s) linked in such a way that the expression of the nucleic acid molecule is modulated. For example, when a pre-sequence or secretory leader participates in secretion of a mature protein, they are operably linked to the promoter. When a promoter affects transcription of a coding sequence, the promoter is operably linked to the coding sequence. When a ribosomal binding site is located at a place capable of being read as a coding sequence, the ribosomal binding site is operably linked to the coding sequence. Generally "operably linked" means in contact with a linked nucleic acid molecule and a secretory leader and to be in a reading frame.

Non-Viral Vectors

Non-viral approaches can also be employed to introduce a therapeutic nucleic acid molecule (e.g., an IFN-α-encoding nucleic acid molecule) into cells to treat or prevent pathogenic infection (e.g., viral infection) or to treat or reduce the symptoms of autoimmune disease or cancer. For example, a heterologous gene (e.g., an interferon, such as IFN-α (e.g., consensus IFN-α) can be introduced into a cell (e.g., an epithelial cell, such as a nasal or pulmonary epithelial cell) by lipofection (see, e.g., Feigner et al., *Proc. Natl. Acad. Sci. USA* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (see, e.g., Wu et al., *Journal of Biological Chemistry* 263:14621, 1988; Wu et al., *Journal of Biological Chemistry* 264:16985, 1989), or, less preferably, micro-injection under surgical conditions (see, e.g., Wolff et al., *Science* 247:1465, 1990). Gene transfer can also be achieved by the use of calcium phosphate, DEAE dextran, electroporation, and protoplast fusion. Liposomes, microparticles, or nanoparticles can also be potentially beneficial for delivery of a nucleic acid molecule (e.g., an IFN-α-encoding nucleic acid molecule) or a protein into a cell or into a patient in order to stimulate an immune response against a pathogen (e.g., a virus). Other non-viral methods of delivering IFN-α are described in, e.g., Coleman et al., Hum. Gene Ther. 9:2223-2230, 1998, and Horton et al., Proc. Natl. Acad. Sci. USA 96:1553-1558, 1999).

Methods of Prophylaxis or Treatment of Pathogenic Infection Using Compositions of the Invention The pharmaceutical compositions of the invention can be used as gene therapy and/or genetic vaccines for treating or inhibiting infection by pathogens, such as bacteria, viruses, fungus, and parasites. In particular, the compositions of the invention can be used to treat (pre- or post-exposure) infection by viruses (e.g., a member of the Flaviviridae family (e.g., a member of the *Flavivirus, Pestivirus*, and *Hepacivirus* genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus; a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabiá virus, Tacaribe virus, Tamiami virus, Whitewater Arroyo virus, Chapare virus, and Lujo virus; a member of the Bunyaviridae family (e.g., a member of the *Hantavirus, Nairovirus, Orthobunyavirus*, and *Phlebovirus* genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus; a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O' nyong'nyong virus, and the chikungunya virus; a member of the Poxyiridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively)).

The pharmaceutical compositions include vectors encoding IFN (e.g., IFN-α, such as conIFN-α) that can be administered in vivo or ex vivo.

IFN-α is one of the earliest cytokines released by the antigen-presenting cell as part of the innate immune response and is directly responsible for NK and T cell responsiveness, which drives the subsequent immune response. NK cells are one of the first professional killing cells to arrive in the early antiviral immune response. In addition, IFN-α appears to be the principle cytokine mediating expansion of CD8+ T cells. Because of the early response of IFN-α in the immune cascade, its primary role is suggested to be to induce a priming state during the initial response to infection, and it has been shown that low dose IFN-α results in increased protection from a viral challenge (see, e.g., Brassard et al., J. Leuk. Biol. 71:565-581, 2002).

In addition, interferon induces the expression of MX proteins, which are 7-80 kDa proteins with GTPase activity that affect viral replication by interfering with transcription (i.e., they inhibit viral RNA polymerases) of influenza and other negative strand RNA viruses (Acheson, In "Fundamentals of Molecular Virology," J. Wiley and Sons, Hoboken N.J., 2007).

Interferon also induces the expression of ribonuclease L, which degrades viral (and host) mRNA, and thus leads to an inhibition of viral replication by suppression of viral protein synthesis. (Acheson, 2007). Thus, the expression of IFN-α in the transduced/transfected cells (e.g., epithelial cells) of a subject provides prophylaxis and/or treatment of pathogenic infection by, in part, activating these and other pathways that stimulate the subject's immune response and protect the subject, pre- and post-exposure, against pathogenic (e.g., viral) infection.

The pharmaceutical compositions of the invention act via a two-step process: administration and expression. For example, after intranasal administration, the Ad5 virus enters the epithelial cells of the upper and/or lower respiratory tract and transports the IFN-α nucleic acid molecule to the nucleus. Next, the IFN-α nucleic acid molecule is transcribed and the resulting mRNA is translated, post-translationally modified with glycosylation, expressed as a mature IFN-α cytokine on the cell surface. The adenovirus itself does not replicate as it has been rendered replication deficient. Once the IFN-α is expressed on the cell surface, it functions in the same manner as naturally in situ-produced IFN-α.

Accordingly, the vectors can be used to transduce or transfect a subject's cells in vivo (e.g., epithelial cells, such as nasal or pulmonary epithelial cells) by administering the vector in a dosage and form discussed herein (e.g., as an aerosolized powder, liquid mist, or gel) to the subject (e.g., via intranasal or pulmonary administration) to provide prophylaxis and/or treatment of pathogenic infection. Alternatively, cells can be removed from the subject and transduced or transfected ex vivo with the vector encoding IFN and those cells can be returned to the subject to provide prophylaxis and/or treatment of pathogenic infection. In an embodiment, cells of the subject are removed and treated ex vivo with the Ad5-IFN-α vector of the invention. The cells are then administered to the patient, pre- or post-exposure, to treat or inhibit pathogenic infection. Preferably at least about $1 \times 10^4$ to about $10 \times 10^6$ cells are treated and reintroduced to the subject.

In an embodiment, a sufficient amount of the pharmaceutical composition is administered to a subject to achieve a peak blood level of IFN-α due to expression from the transfected/transduced cells of at least between about 0.0001 to $5.0 \times 10^5$ IU/ml, preferably between about 0.0002 to $2.0 \times 10^5$ IU/mL, and most preferably between about 0.0005 to $1.0 \times 10^5$ IU/mL (see, e.g., NIBSC code: 94/784 and 94/786; WHO International Standard for INTERFERON ALPHA, (Human leukocyte-derived); dated 14, Feb. 2008; Meager et al., J. Immunol. Methods 257:17-33, 2001; and Mire-Sluis et al., J. Interferon Cytokine Res. 16:637-643, 1996). In another embodiment, the amount of circulating IFN-α is between about 100 IU/ml and 1,000 IU/ml (e.g., about 250 IU/ml). Preferably, the circulating levels of IFN-α remain within this range for at least 1 to 15 days, or at least 1, 2, 3, or 4 weeks, or at least 2-6 months. The expression levels of IFN-α can be determined by measuring the amount of IFN-α in, e.g., the subject's serum (see, e.g., Forti et al., J. Clin. Microbiol. 21:689-693, 1985). In other embodiments, the anti-viral effects of IFN-α remain evident in the subject for at least 1, 2, 3, or 4 weeks, more preferably for at least 2, 4, or 6 months, and most preferably for 1 year or more. The anti-viral effects of IFN-α can be determined by measuring the upregulation or activity of the double-stranded RNA (dsRNA)-dependent protein kinase R (PKR), the 2'-5'-oligoadenylate synthetase (2'-5'-OAS), IFN-inducible Mx proteins, a tryptophan-degrading enzyme (see, e.g., Pfefferkorn, Proc. Natl. Acad. Sci. USA 81:908-912, 1984), adenosine deaminase (ADAR1), IFN-stimulated gene 20 (ISG20), p56, ISG15, mGBP2, GBP-1, the APOBEC proteins, viperin, or other factors (see, e.g., Zhang et al., J. Virol., 81:11246-11255, 2007). Assays for measuring the anti-viral effects of IFN-α can be found in, e.g., U.S. Pat. No. 7,442,527, which is incorporated by reference herein in its entirety.

Upon administration of the pharmaceutical composition including the IFN-α delivery vector (e.g., an Ad5 delivery vector), e.g., to nasal or pulmonary epithelial cells, the nucleic acid molecule encoding IFN-α incorporates into the cells. These cells then produce IFN-α during the course of their lifespan until death or apoptosis, thereby allowing for expression of human IFN-α lasting for several hours, days, or weeks or more (e.g., about 1-15 days, 1-4 weeks, or 2-6 months) compared to hours for exogenously administered rhIFN-α. Furthermore, the IFN produced from, e.g., an Ad5-hIFN vector will be fully glycosylated unlike the rhIFN-α currently being commercially prepared by eukaryotic fermentation (i.e., Infergen® (Alfacon; DIN 2239832)). In addition, the therapeutic effects (e.g., anti-viral effects) of IFN-α can extend for at least 1, 2, 3, or 4 weeks, more preferably for at least 2, 4, or 6 months, and most preferably for 1 year or more.

Naturally occurring IFN-α is glycosylated. Most rhIFN products are not glycosylated as they are made via prokaryotic fermentation. Due to the location of the glycosylation sites, there is no risk of impeding receptor binding with the addition of glycosylation. However, the pharmacokinetics of glycosylated and unglycosylated IFN-α may well be different, and the stability of the protein may be influenced by glycosylation, as is the case for human granulocyte-macrophage colony-stimulating factor (GM-CSF; see Adolf et al. (Biochem. J. 276:511-518, 1991). Further, the immunogenicity of rhIFN-α might be affected by the lack of glycosylation. Gribben et al. have reported that four out of 16 patients receiving rhGM-CSF produced in yeast developed antibodies to this protein; these antibodies reacted with epitopes that were exposed in the recombinant factor, but would have been protected by glycosylation (see Gribben et al., Lancet 335: 434-437, 1990). Induction of antibodies to non-glycosylated rhIFN-α after prolonged treatment of patients has been described, and it has been speculated that natural IFN-α may be less immunogenic than the recombinant proteins (see Figlin and Itri, Semin. Hematol. 25:9-15, 1988, and Galton et al., Lancet 2:572-573, 1989).

Although there is evidence using all forms of IFN (e.g., α, β, ω, γ) that glycosylation does not appear to affect the specific antiviral/biological activity of the protein (see Bocci, Trends Biochem Sci 8:432-434, 1983, and Adolf et al., Biochem J. 276:511-518, 1991), it is believed that glycosylation of IFN may be important for other reasons. There are studies specifically working on different translational methods to manufacture fully glycosylated hIFNA ex vivo (see, e.g., Rossmann et al., Prot. Exp. Purif. 7:335-342, 1996), and patents filed protecting these methods (see, e.g., U.S. Pat. Nos. 7,445,774; 7,338,654; 7,311,903; and 7,129,390). Thus, glycosylation is clearly a desirable factor in IFN. The pharmaceutical compositions of the invention, which deliver a vector that promotes expression of a fully glycosylated hIFN in situ, will likely result in a protein with more stability and less immunogenic effects than currently administered rhIFN polypeptides lacking glycosylation, while maintaining the same level of therapeutic (e.g., antiviral) activity.

Expression of IFN-α (e.g., conIFN-α) in the cells of a subject transfected/transduced with the delivery vector of the invention provides fast acting protection to the subject against pathogenic infection (e.g., viral infection). The IFN-α delivery vector of the invention is fast acting because the Ad5 vector incorporates into epithelial cells (e.g., nasal or pulmonary epithelial cells), journeying from the cell surface to the nucleus within 30 minutes. The IFN-α delivery vector of the invention is particularly effective when administered, e.g., intranasally, because the nasal cavity has a large surface area (100-200 cm square), which allows the Ad5 delivery vector to penetrate into millions of upper and/or lower respiratory epithelial cells. Once incorporated, the epithelial cells begin to generate the IFN-α (e.g., conIFN-α) as if it was endogenous to the cell; the IFN-α is expressed on the cell surface and it is secreted into the host circulation.

Expression of IFN-α typically occurs within 24 hours or less (e.g., as early as 3 hours) after administration of the delivery vector. This result is beneficial, especially in cases where rapid treatment response is preferable (e.g., viral outbreaks in the public arena or in situations where a pathogen has been intentionally released (e.g., against military personnel deployed on the frontline)). The IFN-α delivery vector of the invention provides medical personnel in the public sector, as well as military planners and others with the ability to act quickly when responding to various operational threat situations where there may be uncertainty as to the presence of an infectious pathogen. For example, today, military planners will not deploy into areas with endemic pathogenic risks without the proper vaccinations. This delays greatly the ability of the military, law enforcement agents, or local emergency coordinator (LEC) to respond promptly to global threats. The pharmaceutical compositions of the invention can be used to mitigate those risks and speed the response time against pathogenic exposure or outbreaks.

The compositions of the invention may be administered in a single dose or in multiple doses separately from or coextensively with other therapies for pathogenic infection (e.g., vaccines), or as a stand-alone therapy. The compositions of the invention may, but need not, also include additional therapeutic agents. These additional therapeutic agents can also be encoded as nucleic acid molecules in the same or a different delivery vector (e.g., a viral vector) and expressed as a polypeptide with the IFN or they can be administered as polypeptides or drugs with the compositions of the invention, e.g., as a single pharmaceutical composition or in separate pharmaceutical compositions.

The compositions of the invention can be administered to a subject (e.g., a human), pre- or post-exposure to a pathogenic infection (e.g., a viral infection), to treat, prevent, ameliorate, inhibit the progression of, or reduce the severity of one or more symptoms of the pathogenic infection in the subject. Examples of the symptoms of pathogenic infection, in particular, viral infection, that can be treated using the compositions of the invention include, e.g., fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death. These symptoms, and their resolution during treatment, may be measured by, e.g., a physician during a physical examination or by other tests and methods known in the art.

The dose of the compositions of the invention (e.g., the number of IFN-encoding delivery vectors, viral or otherwise) or the number of treatments using the compositions of the invention may be increased or decreased based on the severity of, occurrence of, or progression of, the pathogenic infection in the patient (e.g., based on the severity of one or more symptoms of, e.g., viral infection).

Uses

IFN is known to be effective against a broad range of pathogens, in particular, viruses. Hence the pharmaceutical compositions of this invention are referred to as a "Broad Spectrum Antiviral." Viruses against which the compositions of the invention can be used include the following: a member of the Flaviviridae family (e.g., a member of the *Flavivirus, Pestivirus*, and *Hepacivirus* genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephaio-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus; a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabiá virus, Tacaribe virus, Tamiami virus, Whitewater Arroyo virus, Chapare virus, and Lujo virus; a member of the Bunyaviridae family (e.g., a member of the *Hantavirus, Nairovirus, Orthobunyavirus*, and *Phlebovirus* genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus; a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O' nyong'nyong virus, and the chikungunya virus; a member of the Poxyiridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively).

Particular indications that are contemplated for the pharmaceutical compositions of the invention, and which are currently being or have been evaluated in conjunction with the Division of Microbiology and Infectious Disease (DMID), part of the National Institute of Allergy and Infectious Disease (NIAID), include: Dengue, Punta Toro (a BSL-2 surrogate for Rift Valley Fever), monkeypox, Flu A (H5N1 and H1N1), SARS, Yellow Fever, Pichinde (a BSL-2 surrogate for Lassa Fever), Western Equine Encephalitis, Venezuelan Equine Encephalitis, and West Nile Virus. In broader terms, the IFN-α delivery vector and pharmaceutical compositions containing it will be effective against, at least, the following viral families: Alphaviridae, Filoviridae, Flaviviridae, Orthomyxoviridae, Bunyaviridae, Arenaviridae, Herpesviridae, Hepadnaviridae, Coronaviridae, and Poxyiridae (see Examples).

A significant proportion of the human population has been exposed to many adenoviral strains, including Ad5. Thus, there is a good probability the immune system of any potential recipient of the pharmaceutical compositions of the invention has "seen" Ad5 before and would be able to quickly mount an immune response to it. This was the case with the MRKAd5 HIV-1 gag/pol/nef HIV vaccine, which was tested on HIV negative patients in a phase II clinical trial in 2008. This trial, which utilized injections, resulted in "futility," meaning there was no protection seen: the levels of infection in inoculated subjects was the same as non-inoculated ones (Buchbinder et al., Lancet 372:1881-1893, 2008). Positive serostatus for Ad5 was significantly associated with acquisition (Robb, Lancet 372:1857-1858, 2008), and the design of the vaccine is "at the centre of the study's failure" (White, Lancet 373:805, 2009). Thus, Ad5 vectored vaccines were thought to be useless due to the high probability of pre-existing immunity. Indeed, all military personnel are actively vaccinated with Ad4 and Ad7 vaccines during basic training medical preparation following enlistment.

To circumvent pre-existing immunity to the delivery vector, the IFN-α delivery vector of the invention, and pharmaceutical compositions containing it, can be administered via, e.g., a pulmonary or intranasal route, which avoids problems with pre-existing immunity to the delivery vector. This is believed to be due to the lack of contact between the vector (e.g., the adenoviral vector (e.g., Ad5)) and the immune system (e.g., the immune components in blood), as the vector incorporates into, e.g., epithelial cells directly upon administration. These epithelial cells act as a functional barrier to the cells and antibodies of the immune system. Thus, the delivery vector is not exposed to the circulation; only the IFN is released into the bloodstream with no traces of the vector remaining (see FIG. 3).

Methods of Prophylaxis or Treatment of Autoimmune Disease or Cancer Using the Compositions of the Invention The pharmaceutical compositions of the invention can also be used as gene therapy and/or genetic vaccines for treating or reducing one or more symptoms of autoimmune disease and cancer. The mechanism of action of the compositions of the invention described above applies equally to their use in this context.

Interferons exhibit both antiviral and antiproliferative activity. IFN-α is currently approved in the United States and other countries for the treatment of hairy cell leukemia, venereal warts, Kaposi's Sarcoma, and chronic non-A, non-B hepatitis. Two variants of IFN-α have received approval for therapeutic use: Interferon alfa-2a, marketed under the trade name ROFERON™-A, and Interferon alfa-2b, marketed under the trade name INTRON™ A. The amino acid sequences of ROFERON™-A and INTRON™ A differ at a single position but otherwise are identical to the amino acid sequence of alpha-interferon subtype 2 (subtype A).

In addition to the labeled indications, IFN-α is being used or evaluated alone or in conjunction with chemotherapeutic agents in a variety of other cellular proliferation disorders, including chronic myelogenous leukemia, multiple myeloma, superficial bladder cancer, skin cancers (basal cell carcinoma and malignant melanoma), renal cell carcinoma, ovarian cancer, low grade lymphocytic and cutaneous T cell lymphoma, and glioma. IFN-α may be effective in combination with other chemotherapy agents for the treatment of solid tumors that arise from lung, colorectal and breast cancer (see Rosenberg et al. "Principles and Applications of Biologic Therapy" in Cancer: Principles and Practices of Oncology, 3rd ed., Devita et al., eds. pp. 301-547 (1989), Balmer DICP, Ann Pharmacother 24, 761-768 (1990)).

BETASERON™ (Schering Corp's recombinant interferon beta-1b) was the first drug indicated specifically for the treatment of MS. In a major clinical trial, BETASERON™ was found to be effective in reducing the number and severity of exacerbations, or relapses, suffered by MS patients, as well as decreasing magnetic resonance imaging (MRI) evidence of MS activity in the brain. Importantly, the results of the trial pertained only to the relapsing-remitting patient group, since other forms of MS were not represented in the trial. Moreover, the trial demonstrated no beneficial effect of the drug on ultimate disability of MS over the 2 to 3 years of the study, and the effectiveness of the drug is significantly impaired by its side effects. U.S. Pat. Nos. 7,105,154; 5,372,808; 5,846,526; 6,204,022; 6,060,450; and 6,361,769 also describe the use of IFN therapy for treating autoimmune diseases and cancer; each of these publications is incorporated herein by reference). U.S. Pat. No. 7,442,380 describes the treatment of autoimmune diseases caused by viral infection using interferons.

Thus, the compositions of the invention (e.g., an Ad5-IFNα) can be administered to a subject (e.g., a human) to treat or reduce one or more symptoms of autoimmune disease (e.g., multiple sclerosis, type I diabetes, lupus, Addison's disease, myasthenia gravis, and amyotrophic lateral sclerosis) or cancer in the subject. Examples of the symptoms of autoimmune disease that can be treated or reduced using the compositions of the invention include, e.g., increased levels of autoantibodies, increased levels of autoreactive T cells, loss of targeted cells (e.g., pancreatic β-islet cells), fatigue, depression, sensitivity to cold, weight gain, muscle weakness, constipation, insomnia, irritability, weight loss, bulging eyes, muscle tremors, skin rashes, painful or swollen joints, sensitivity to the sun, loss of coordination, and paralysis. These symptoms, and their resolution during treatment, may be measured by, e.g., a physician during a physical examination or by other tests and methods known in the art.

The dose of the compositions of the invention (e.g., the number of IFN-encoding delivery vectors, viral or otherwise) or the number of treatments using the compositions of the invention may be increased or decreased based on the severity of, occurrence of, or progression of, the disease or symptoms in the patient.

Additional Therapeutic Regimens

If desired, the subject may also receive additional therapeutic regimens. For example, an additional therapeutic agent may be admixed into a single formulation together with the pharmaceutical compositions described herein at concentrations known to be effective for such therapeutic agents. Additional therapeutic agents may also be delivered separately. When agents are present in different pharmaceutical compositions, different routes of administration may be employed. Particularly useful therapeutic agents include, e.g., antiviral agents, immunostimulatory agents, and other immunization vaccines. When treating cancer with the compositions of the invention, particularly useful additional therapeutic agents include chemotherapeutic agents, such as, e.g., camptothecin, homocamptothecin, colchicine, thiocolchicine, combretastatin, dolastatin, doxorubicin, methotrexate, podophyllotoxin, rhizoxin, rhizoxin D, a taxol, paclitaxel, CC1065, and a maytansinoid.

In some instances, the pharmaceutical composition and additional therapeutic agents are administered at least one hour, two hours, four hours, six hours, 10 hours, 12 hours, 18 hours, 24 hours, three days, seven days, fourteen days, or one month apart. The dosage and frequency of administration of each component can be controlled independently. The additional therapeutic agents described herein may be admixed with additional active or inert ingredients, e.g., in conventional pharmaceutically acceptable carriers. A pharmaceutical carrier can be any compatible, non-toxic substance suitable for the administration of the compositions of the invention to a subject. Pharmaceutically acceptable carriers include, for example, water, saline, buffers and other compounds, described, for example, in the Merck Index, Merck & Co., Rahway, N.J. A slow release formulation or a slow release apparatus may be also be used for continuous administration. The additional therapeutic regimen may involve other therapies, including modification to the lifestyle of the subject being treated.

Antiviral Agents

Antiviral agents may be used as an additional therapeutic agent, either in combination with the vaccine or in a separate administration. Exemplary antiviral agents are abacavir, aciclovir, acyclovir, adefovir, amantadine, amprenavir, arbidol, atazanavir, atripla, brivudine, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, gardasil, ibacitabine, immunovir, idoxuridine, imiquimod, indinavir, inosine, integrase inhibitors, interferon type III, interferon type II, interferon type I, interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine. Exemplary antiviral agents are listed in, e.g., U.S. Pat. Nos. 6,093,550 and 6,894,033, hereby incorporated by reference.

Anti-Bacterial Agents

The compositions of the invention (e.g., Ad5-IFNα) can be administered with an anti-bacterial agent, such as an antibiotic, e.g., one or more penicillins, cephalosporins, aminoglycosides, macrolides, sulfa compounds, fluoroquinolones, or tetracyclines. Other examples of anti-bacterial agents include penicillin G, penicillin V, methicillin, nafcillin, oxacillin, cloxacillin, dicloxacillion, ampicillin, amoxicillin, bacampicillin, cyclacillin, carbenicillin indanyl, ticarcillin, mezlocillin, piperacillin, cephalothin, cefazolin, cephapirin, cephradine, cephalexin, cefadroxil, cefamandole nafate, cefuroxime, cefonicid, ceforanide, cefaclor, cefoxitin, cefotetan, cefmetazole, cefataxime, ceftizoxime, ceftriaxone, ceftazidime, cefoperazone, moxalactam, cefixime, erythromycin, stearate, ethylsuccinate, estolate, lactobionate, gluceptate, azithromycin, clarithromycin oxytetracycline, demeclocycline, doxycycline, minocycline, amikacin sulfate, gentamicin sulfate, intrathecal, kanamycin sulfate, netilmicin sulfate, streptomycin sulfate, tobramycin sulfate, neomycin sulfate, sulfadiazine, sulfamethizole, sulfisoxazole, sulfisoxazole acetyl, sulfamethoxazole, trisulfapyrimidines, phenazopyridine, erythromycin ethylsuccinate, Trimethoprim, Ciprofloxacin, Ciprofloxacin hydrochloride, enoxacin, Lomefloxacin hydrochloride, Norfloxacin, Ofloxacin, vancomycin hydrochloride, teicoplanin, rifampin, metronidazole, metronidazole hydrochloride, polmyxins, bacitracin, methenamine, methenamine hippurate, methenamine mandelate, nitrofurantoin, phenazopyridine hydrochloride, silver nitrate, acetic acid, Domeboro solution, m-cresyl acetate, Colymycin S otic, cortisporin, tridesilon, ciclopiroxolamine, clioquinol, griseofulvin, fulvicin, grisactin, grisactin ultra, grifulvin V, halaprogin, pyrithione zinc, selenium sulfide, tolnaftate, undecylenic acid, naftfine, terbinafind, imidazole, econazole, ketoconazole, miconaxole nitrate, Monistat-Derm, oxiconazole nitrate, sulconazole nitrate, bis-triazoles, intraconazole, amphotericin B, nystatin, mycolstatin, nilstat, butoconazole, clotrimazole, tioconazold, fluconazole, intraconazole, terconazole, nystatin, mycostatin, O-V Statin, cantharidin, intralesional, podophyllin resin, podofilox, salicylic acid, benzylbenzoate, crotamiton, lindane, malathion, permethrin, phrethrins, piperonyl butoxide, sulfur, isoniazid, pyrazinamide, ethambutol, capreomycin sulfate, cycloserine, ethambutol hydrochloride, ethionamide, clofazimine, dapsone, ethionamide, itraconazole, potassium iodide flucytosine, chloroquine phosphate, hydroxychloroquine phosphate, chloroquine hydrochloride, quinine sulfate, pyrimethamine/sulfadoxine, mefloquine, quinidine gluconate, dilozanide furoate, eflornithine hydrochloride, furazolidone, iodoquinol, melarsoprol, metronidazole, nifurtimox, paramomycin sulfate, pentamidine isethionate, primaquine phosphate, quinine sulfate, sodium stibogluconate, meglumine antimoniate, trimetrexate glucuronate, pyrimethamine, albendazole, diethycicarbamazine citrate, ivermectin, mebendazole, metrifonate, niclosamide, oxamniquine, pyrantel pamoate, suramin sodium, thiabendazole, cytarabine, idoxuridine, trifluridine, vidarabine, acyclovir, Zidovudine, ribavirin, bromovinyldeoxyuridine, fluoroiodoaracytosine, amantadine, acemannan, amphotericin B methyl, Ampligen, castanospermine, soluble $CD_4$, dextran sulfate, dideoxycytidine, dideoxyinosine, didihydrodideoxythymidine, foscarnet sodium, fusidic acid, HPA-23, isoprinosine, penicillamine, peptide T, ribavirin, rifabutin, didanosine, zalcitabine, and the like.

Immunostimulatory Agents

Immunogenicity of the pharmaceutical compositions of the invention may be significantly improved if the compositions of the present invention (e.g., Ad5-IFNα) are co-administered with an immunostimulatory agent or adjuvant. Exemplary immunostimulatory agents include aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

Immunization Vaccines

In some instances, it may be desirable to combine the compositions of the present invention with compositions that induce protective responses against other viruses. For example, the compositions of the present invention (e.g., Ad5-IFNα) can be administered simultaneously, separately, or sequentially with an immunization vaccine, such as a vaccine for, e.g., influenza, malaria, tuberculosis, smallpox, measles, rubella, mumps, or any other vaccines known in the art.

For example, the vaccine can be, e.g., a bacterial, viral, fungal, or parasite vaccine known in the art for treating a bacterial, viral, fungal, or parasitic agent, respectively. The vaccine may be directed against a bacterium selected from *Pseudomonas aeruginosa, Salmonella typhimurium, Escherichia coli, Klebsiella pneumoniae, Bruscella, Burkholderia mallei, Yersinia pestis*, and *Bacillus anthracis*; a virus selected from a member of the Flaviviridae family (e.g., a member of the *Flavivirus, Pestivirus*, and *Hepacivirus* genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus; a virus selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabiá virus, Tacaribe virus, Tamiami virus, Whitewater Arroyo virus, Chapare virus, and Lujo virus; a virus selected from a member of the Bunyaviridae family (e.g., a member of the *Hantavirus, Nairovirus, Orthobunyavirus,* and *Phlebovirus* genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus; a virus selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxyiridae family (e.g., a member of the *Orthopoxvirus* genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively); or a fungus selected from *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus,* and *Rhizopus arrhizus*; or parasite selected from *Toxoplasma gondii, Plasmodium falciparum, P. vivax, P. ovale, P. malariae, Trypanosoma* spp., and *Legionella* spp.

Examples of vaccines known in the art that can be administered in combination with the compositions of the present invention (e.g., the Ad5-IFNα constructs described herein) include AVA (BioThrax) for anthrax; VAR (Varivax) and MMRV (ProQuad) for chickenpox; DTaP (Daptacel, Infanrix, Tripedia), Td (Decavaca, generic), DT (-generic-), Tdap (Boostrix, Adacel), DTaP-IPV (Kinrix), DTaP-HepB-IPV (Pediarix), DTaP-IPV/Hib (Pentacel), and DTaP/Hib (TriHIBit) for Diphtheria; HepA (Havrix, Vaqta) and HepA-HepB (Twinrix) for Hepatitis A; HepB (Engerix-B, Recombivax HB), Hib-HepB (Comvax), DTaP-HepB-IPV (Pediarix), and HepA-HepB (Twinrix) for Hepatitis B; Hib (ActHIB, PedvaxHIB, Hiberix), Hib-HepB (Comvax), DTaP/Hib (TriHIBit), and DTaP-IPV/Hib (Pentacel) for *Haemophilus influenzae* type b; HPV4 (Gardasil) and HPV2 (Cervarix) for Human Papillomavirus (HPV); TIV (Afluria, Agriflu, Flu-Laval, Fluarix, Fluvirin, Fluzone) and LAIV (FluMist) for Influenza; JE (Ixiaro and JE-Vax) for Japanese encephalitis (JE); MMR (M-M-R II) and MMRV (ProQuad) for Measles; MCV4 (Menactra), MPSV4 (Menomune), and MODC (Menveo) for Meningitis; MMR (M-M-R II) and MMRV (ProQuad) for Mumps; DTaP (Daptacel, Infanrix, Tripedia), Tdap (Adacel, Boostrix), DTaP-IPV (Kinrix), DTaP-HepB-IPV (Pediarix), DTaP-IPV/Hib (Pentacel), and DTaP/Hib (TriHIBit) for Pertussis; PCV7 (Prevnar), PCV13 (Prevnar13), and PPSV23 (Pneumovax 23) for Bacterial Pneumonia; Polio (Ipol), DTaP-IPV (Kinrix), DTaP-HepB-IPV (Pediarix), and DTaP-IPV/Hib (Pentacel) for Polio; Rabies (Imovax Rabies and RabAvert); RV1 (Rotarix) and RV5 (RotaTeq) for Rotavirus; MMR (M-M-R II) and MMRV (ProQuad) for Rubella; ZOS (Zostavax) for Shingles; Vaccinia (ACAM2000, Dryvax) for Smallpox and Monkeypox; DTaP (Daptacel, Infanrix, Tripedia), Td (Decavac, generic), DT (-generic-), TT (-generic-), Tdap (Boostrix, Adacel), DTaP-IPV (Kinrix), DTaP-HepB-IPV (Pediarix), DTaP-IPV/Hib (Pentacel), and DTaP/Hib (TriHIBit) for Tetanus; BCG (TICE BCG, Mycobax) for Tuberculosis (TB); Typhoid Oral (Vivotif) and Typhoid Polysaccharide (Typhim Vi) for Typhoid; and YF (YF-Vax) for Yellow Fever.

Ebola Vaccine

Ad-CAGoptZGP is a vaccine that uses an Adenovirus 5 backbone and encodes the surface proteins of the Ebola virus (see Richardson et al. (PLoS 4:e5308, 2009)). Earlier versions of this vaccine have been previously shown to protect mice, guinea pigs and nonhuman primates from an otherwise lethal challenge of Zaire Ebola virus. Ad-CAGoptZGP incorporates three improvements: codon optimization of the gene insert, inclusion of a consensus Kozak sequence, and reconfiguration of a CAG promoter. Transfection or transduction of cells with Ad-CAGoptZGP results in high expression of the Ebola glycoprotein from those cells, and allows for a functional dose ~100 times lower than with other adenovirus-based Ebola vaccine constructs and with a faster time to immunity. Finally, Ad-CAGoptZGP is capable of inducing full protection to mice (partial protection to guinea pigs) when given 30 minutes post-challenge, whereas previous vaccines were not functional post-exposure. The strength of this vaccine is its lasting immunity.

In an embodiment, a pharmaceutical composition of the invention (e.g., the Ad5-IFNα constructs described herein) can be administered simultaneously, separately, or sequentially with the Ad-CAGoptZGP Ebola vaccine. Preferably, one or both of the agents are formulated for intranasal or pulmonary administration. Our experimental data shows significant synergy when, e.g., Ad5-IFNα and Ad-CAGoptZGP are combined (whether administered in a single composition or in separate compositions; see, e.g., Example 14 herein). Specifically, complete treatment efficacy is seen 30 min post-exposure with ZEBOV with no reduction in body weight in both mouse and Guinea pig models. We expect to gain the benefits of both rapid onset (3 hours) of Ad5-IFNα and long lasting protection of Ad-CAGoptZGP in order to maximize the protective benefit of both components, as is seen in Table 1. The combination of an immune stimulator and Ebola vaccine contributes to a highly effective, focused therapy, and a broad spectrum antiviral makes this combination a superior treatment option.

TABLE 1

Summary of capabilities of Ad5-IFNα, Ad-CAGoptZGP Ebola vaccine, and their combination as a prophylactic for Ebola viruses

| | |
|---|---|
| Combination Prophylactic | Fast acting AND long lasting immunity<br>Excellent efficacy pre-and post-exposure<br>Needle-free<br>Cost effective manufacturing |
| Ad-CAGoptZGP | Long lasting immunity<br>Some efficacy post-exposure<br>Needle-free<br>Simple cost-effective manufacturing |
| Ad5-IFNα | Rapid onset (3 hours)<br>Broad spectrum protection<br>Needle-free<br>Simple cost-effective manufacturing<br>Efficacy pre-and post-exposure<br>Known and acceptable safety profiles of all components |

The combination of Ad5-IFNα and Ad-CAGoptZGP also provides for rapid onset of therapeutic and prophylactic effects and sustained protection against reinfection. The combination of Ad5-IFNα and Ad-CAGoptZGP (either separately or in combination) promotes direct stimulation of the innate immune system within 1-10 hours (e.g., within 3 hours), which acts to counter, e.g., viral hemorrhagic fever viruses present within the recipient. Rapid onset to protection is one of the many benefits of the combination therapy. The combination of Ad5-IFNα and Ad-CAGoptZGP is also quickly fully functional with a single dose, although multiple doses (e.g., 2, 3, 4, or 5 doses) of one or both of the agents can be administered, as needed.

Expeditionary & Shelf Stable

To minimize logistical constraints, the combination of Ad5-IFNα and Ad-CAGoptZGP can be formulated to be shelf stable and expeditionarily rugged. Formulations described herein allow for deployment of the agent(s) at >35° C., if necessary, for greater than, e.g., 30-90 days (e.g., at least 60 days) and for short periods of between 30 minutes and 5 hours (e.g., at least 1 hour) at temperatures as high as 90° C.

Filovirus Efficacy Data

Ad5-IFNα and Ad-CAGoptZGP each have been tested separately and in combination in well characterized animal models of Filovirus infection (Zaire Ebola; ZEBOV). Mouse studies showed that dosing with a range of $10^4$ to $10^6$ plaque forming units (PFU) of Ad-CAGoptZGP was fully protective, and $10^7$ PFU of Ad5-IFNα treated or pre-treated mice, resulting in complete survival and negligible weight loss.

Similar results were obtained from a guinea pig model of fatal ZEBOV infection in which intranasal delivery of $2\times10^8$ PFU mAd5-IFNα resulted in 100% survival and slight weight loss for those treated compared to 100% fatal for those untreated animals. $10^{10}$ PFU Ad-CAGoptZGP resulted in 33% survival while the combination of Ad5-IFNα and Ad-CAGoptZGP resulted in 100% survival with no weight loss.

These results are particularly impressive given the susceptibility of Guinea pigs to ZEBOV. In this study the efficacy of daily injections of recombinant IFNα protein was also assessed, and it was noted that some survival benefit was observed (FIG. 10B).

Formulation and Administration of the Pharmaceutical Compositions of the Invention The compositions utilized in the methods described herein can be formulated for administration by a route selected from, e.g., parenteral, dermal, transdermal, ocular, inhalation, buccal, sublingual, perilingual, nasal, rectal, topical administration, and oral administration. Administration may be by, e.g., intranasal release. Parenteral administration includes intravenous, intraperitoneal, subcutaneous, and intramuscular administration. Parenteral, intranasal or intraocular administration may be provided by using, e.g., aqueous suspensions, isotonic saline solutions, sterile and injectable solutions containing pharmacologically compatible dispersants and/or solubilizers, for example, propylene glycol or polyethylene glycol, lyophilized powder formulations, and gel formulations. The preferred method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the IFN delivery vehicle composition of the invention. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, e.g., an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

In some instances, it may be desirable to combine the compositions of the invention with compositions that induce protective responses against other viruses. For example, the compositions of the present invention can be administered simultaneously, separately, or sequentially with other immunization vaccines, such as those for, e.g., influenza, malaria, tuberculosis, or any other vaccines known in the art.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastro-intestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The compositions of the invention may be administered to provide pre-exposure prophylaxis or after a subject has been exposed to a pathogen, such as a virus. The composition may be administered, e.g., 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure, or may be administered to the subject 15-30 minutes or 1, 2, 3, 4, 5, 6, 7, 8, 9, 10, 12, 20, 24, 48, 72 hours, or longer post-exposure to the pathogen (e.g., a viral pathogen).

When treating autoimmune disease or cancer, the compositions of the invention may be administered to the subject either before the occurrence of symptoms or a definitive diagnosis or after diagnosis or symptoms become evident. For example, the composition may be administered, e.g., immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the IFN delivery vector (e.g., an Ad5 con-IFN-α delivery vector) and, if desired, one or more immunomodulatory agents, such as in a sealed package of tablets or capsules, or in a suitable dry powder inhaler (DPI) capable of administering one or more doses.

Nasal or Pulmonary Delivery

There are several benefits of intranasal or pulmonary administration over, e.g., oral, intravascular, or intramuscular administration. In particular, an intranasal or pulmonary administration route is less harsh for an adenoviral vector system. There are fewer proteolytic enzymes present in, e.g., the nasal epithelium and the environment has a more neutral pH (i.e., it is less acidic). Also, the uptake of particles of the viral delivery vector would be more consistent in the nasal or pulmonary mucosa than in the gut where there would be more variation in the content of the intestinal lumen, and thus greater variability in the ability of the vector to transduce/transfect cells in that environment. Moreover, the nasal mucosa is well irrigated, and is thus a permeable mucosal site.

Thus, in an embodiment, the IFN-α delivery vector of the invention, and pharmaceutical compositions containing it, are delivered via an intranasal or pulmonary route in, e.g., lyophilized powder form, in an aerosolized liquid form, or in a gel form. These routes of administration avoid recognition of, e.g., the Ad5 vector by the host immune system, thereby bypassing any pre-existing immunity the host may have. In addition, intranasal and pulmonary delivery allow for easy administration in the event of the need for mass distribution.

Pulmonary and/or intranasal administration of the compositions of the invention includes, e.g., providing a mist (aqueous or fine powder) to the lungs (upper and/or lower respiratory tract) or nasal epithelium, respectively. This form of administration has a number of benefits over conventional needle-based injections. First, it does not involve the use of a needle, which means better patient compliance because it is "pain-free." Second, pulmonary and intranasal administration allows for self-administration, which saves physicians' time, makes instrumentation unnecessary, and eliminates apprehension for the patient. Third, the use of sugar- or salt-based placebo powders or solutions facilitates training for administration without pain. Fourth, there is no risk of medical problems caused by, e.g., needle-borne contamination by bacteria/viruses or other problems from an unclean injection site. Fifth, the distribution of the aerosol or powder results in a thorough and more even application of the vaccine. Sixth, the particle size of the vaccine can be controlled so that effective deposition at, e.g., the upper and/or lower respiratory tract, takes place based on the characteristics of the administration device. Furthermore, needle-based administrations typically require a trained medical professional to insure that the injected medication is correctly delivered to the right compartment of the body (i.e., intravenous versus intramuscular). The preparation of aerosolized adenoviral vectors is described in, e.g., U.S. Pat. No. 7,097,827, which is incorporated by reference herein.

Formulations suitable for use with a nebulizer, either jet or ultrasonic, will typically comprise the vector (e.g., the Ad5-conIFN-α vector) in an aqueous medium at a concentration of, e.g., about 0.01 to 25 mg of vector per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer will have a composition and molarity suitable to adjust the solution to a pH in the range of 3 to 9. Generally, buffer molarities of from 1 mM to 50 mM are suitable for this purpose. Examples of excipients, usually in amounts ranging from 1% to 90% by weight (e.g., 1% to 50% by weight, more preferably 5% to 30% by weight) of the formulation include, e.g., monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; alditols, such as mannitol, xylitol, xylose, maltitol, lactitol, xylitol sorbitol (glucitol), sorbitose, pyranosyl sorbitol, myoinositol and the like; and glycine, $CaCl_2$, hydroxyectoine, ectoine, gelatin, di-myo-inositol phosphate (DIP), cyclic 2,3 diphosphoglycerate (cDPG), 1,1-di-glycerol phosphate (DGP), β-mannosylglycerate (firoin), β-mannosylglyceramide (firoin A), proline betaine and/or derivatives as well as combinations thereof.

The nebulizer formulation may also contain a surfactant to reduce or prevent surface induced aggregation of the composition components caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in, e.g., WO 94/20069, U.S. Pat. No. 5,915,378, U.S. Pat. No. 5,960,792, U.S. Pat. No. 5,957,124, U.S. Pat. No. 5,934,272, U.S. Pat. No. 5,915,378, U.S. Pat. No. 5,855,564, U.S. Pat. No. 5,826,570, and U.S. Pat. No. 5,522,385, each of which is hereby incorporated by reference.

The compositions of the invention (e.g., an adenoviral vector that includes a nucleic acid molecule encoding an interferon (e.g., Ad5-conIFN-$\alpha$)) are preferentially administered intranasally. The Ad5 virus is highly efficient in delivering genes to the epithelial cells of the nasal membranes. Mucosal dosing is efficient because it stimulates both the systemic and mucosal immunity at the portal of entry (see, e.g., Gutierro et al., Vaccine 20:2181-2190, 2002; and Patel et al., J. Infect. Dis. 196:S413-420, 2007). In addition, utilizing live Ad5 virus to deliver the IFN provides an additional route of immune stimulation, thereby acting as an adjuvant in ensuring maximum effect is achieved. Thus, delivering the compositions of the invention to a site where the infectious agent (e.g., a virus) enters will likely result in a lower required dose. Specific instrumentation has been developed to effectively deliver aerosol droplets (diameter>2 um) to this compartment (see, e.g., the Mucosal Atomization Device (MAD300), Wolfe Tory Medical). Droplet (or powdered particle) size is important as aerosols<1 um penetrate further down the respiratory tract and can cause adverse effects.

The compositions of the invention can also be delivered in powder form using, e.g., a metered dose inhaler device. This powder may be produced by lyophilization and may also contain a stabilizer such as human serum albumin (HSA). Typically, more than 0.5% (w/w) HSA is added. Additionally, one or more of the following may be added as an excipient to the preparation, if necessary, to enhance one or more features (e.g., to facilitate dispersal of the powder from a device, to increase the shelf-life of the vaccine composition, or to improve the stability of the vaccine composition during lyophilization): monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; alditols, such as mannitol, xylitol, xylose, maltitol, lactitol, xylitol sorbitol (glucitol), sorbitose, pyranosyl sorbitol, myoinositol and the like; and glycine, $CaCl_2$, hydroxyectoine, ectoine, gelatin, di-myo-inositol phosphate (DIP), cyclic 2,3 diphosphoglycerate (cDPG), 1,1-di-glycerol phosphate (DGP), $\beta$-mannosylglycerate (firoin), $\beta$-mannosylglyceramide (firoin A), proline betaine and/or derivatives as well as combinations thereof. The amount added to the formulation can range from about 0.01 to 200% (w/w), preferably from approximately 1 to 50% (w/w), and more preferably from about 5 to 30% (w/w) of the vector present. Such formulations are then lyophilized and milled to the desired particle size. The particles of the powder shall have aerodynamic properties in the nasal cavities and lung corresponding to particles with a density of about 1 g/$cm^2$ having a median diameter less than 50 um, preferably between 1.5 and 10 um, more preferably of between 1.8 and 7.0 um, and most preferably from about 2.0 to 4 um. The mean particle diameter can be measured using conventional equipment, such as a Cascade Impactor (Andersen, Ga.).

The dry powder formulations of the present invention may conveniently be formulated by first suspending the vector (e.g., an adenoviral vector that includes a nucleic acid molecule encoding an interferon (e.g., Ad5-conIFN-$\alpha$) or other nucleic acid construct of the invention) in an aqueous solution. The relative amounts of vector and any added excipient material will depend on the desired final ratio of vector to excipient. Conveniently, the ratio of vector to excipient will be in the range from about 2:1 to 1:100 (vector:excipient), preferably from 1:1 to 1:10, with a total solids concentration in the aqueous suspension being usually less than 5% by weight, more usually being less than 3% by weight.

The powder may be suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. This mixture is then loaded into the delivery device.

In the case of compositions of the invention that include viral vectors, it is usually desirable that the aqueous solution be buffered in order to enhance the activity of the viral vectors after drying. Buffers or pH-adjusting agents typically include a salt prepared from, e.g., an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

Additional polymeric excipients/additives that can be included in the formulations of the compositions of the invention include, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-$\beta$-cyclodextrin and sulfobutylether-$\beta$-cyclodextrin), polyethylene glycols, and pectin.

The powder compositions of the invention for use in these devices may be generated and/or delivered by methods disclosed in WO 96/32149, WO 97/41833, and WO 98/29096, and in U.S. Pat. Nos. 7,482,024; 7,481,212; 7,371,373; 6,303,582; 6,001,336; 5,997,848; 5,993,783; 5,985,248; 5,976,574; 5,922,354; 5,785,049; and U.S. Pat. No. 5,654,007, each of which is incorporated by reference herein. The powder form can also be administered using, e.g., a prefilled administration device, such as the devices described in, e.g., U.S. Pat. Nos. 5,437,267; 6,068,199; 6,715,485; 5,994,314; 7,235,391; and 6,398,774, each of which is incorporated by reference herein. The powders will generally have moisture contents below about 20% by weight, usually below about 10% by weight, and preferably below about 6% by weight. Such low moisture-containing solids tend to exhibit a greater stability upon packaging and storage.

Mechanical devices designed for pulmonary and/or nasal delivery of the compositions of the invention include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo., USA; the Mucosal Atomization Device (e.g., MAD300), Wolfe Tory Medical; the Acorn II nebulizer, manufactured by Marquest Medical Products, Englewood, Colo., USA; the Ventolin metered dose inhaler, manufactured by Glaxo Inc., Research Triangle Park, N.C., USA; the OptiNose device, manufactured by OptiNose, Oslo, Norway; the Spinhaler powder inhaler, manufactured by Fisons Corp., Bedford, Mass., USA the "standing cloud" device of Nektar Therapeutics, Inc., San Carlos, Calif., USA; the AIR inhaler manufactured by Alkermes, Cambridge, Mass., USA; and the AERx pulmonary drug delivery system manufactured by Aradigm Corporation, Hayward, Calif., USA. See also the delivery devices described in, e.g., U.S. Pat. Nos. 5,522,378; 5,775,320; 5,934,272; and 5,960,792; the OptiNose devices in U.S. Pat. Nos. 6,715,485; 7,347,201; and 7,481,218; and U.S. Patent Application Publication Nos. 2004/0112378; 2005/0072430; 2004/0112379; 2004/0149289; 2005/0028812; 2008/0163874; 2008/0161771; 2008/0223363; 2005/0235992; 2006/0096589; 2006/0169278; 2007/0039614; and 2007/0186927); and the device in U.S. Pat. No. 7,669,597.

The compositions of the invention can also be formulated as intranasal carriers in the form of nasal gels, creams, pastes or ointments that provide a more sustained contact with the nasal mucosal surfaces. These formulations can have a viscosity of, e.g., from about 10 to about 250,000 centipoise (cps), or from about 2500 to 100,000 cps, or from about 5,000 to 50,000 cps or greater. Such carrier viscous formulations may be based upon, simply by way of example, alkylcelluloses and/or other biocompatible carriers of high viscosity well known to the art (see e.g., Remington, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier. The carrier containing the IFN delivery vehicle of the invention can also be, e.g., soaked into a fabric material, such as gauze, that can be applied to the nasal mucosal surfaces to allow for penetration of the delivery vehicles therein.

Examples of gel formulations that can be used to prepare compositions of the invention are also described in, e.g., U.S. Pat. Nos. 7,538,122; 7,387,788; 7,166,575; 6,413,539; and 6,004,583; each of which is incorporated herein by reference. The gel formulations of the invention may also further include a permeation enhancer (penetration enhancer). Permeation enhancers include, but are not limited to, sulfoxides such as dimethylsulfoxide and decylmethylsulfoxide; surfactants such as sodium laurate, sodium lauryl sulfate, cetyltrimethylammonium bromide, benzalkonium chloride, poloxamer (231, 182, 184), tween (20, 40, 60, 80) and lecithin; the 1-substituted azacycloheptan-2-ones, particularly 1-n-dodecylcyclazacycloheptan-2-one; fatty alcohols such as lauryl alcohol, myristyl alcohol, oleyl alcohol and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate, amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine, terpenes; alkanones, and organic acids, particularly salicylic acid and salicylates, citric acid and succinic acid. The permeation enhancer may be present from about 0.1 to about 30% w/w. Preferred permeation enhancers are fatty alcohols and fatty acids. The gel compositions may also include a buffering agent, for example, carbonate buffers, citrate buffers, phosphate buffers, acetate buffers, hydrochloric acid, lactic acid, tartaric acid, inorganic and organic bases. The buffering agent may be present in a concentration of about 1 to about 10 weight percent, more preferred is a concentration of about 2 to about 5 weight percent, depending on the type of buffering agent(s) used, as known by the one skilled in the art. Concentrations of the buffering agent(s) may vary, however, and the buffering agent may replace up to 100% of the water amount within the composition.

Dosage

The pharmaceutical compositions of the invention can be administered in a therapeutically effective amount that provides an immunogenic and/or protective effect against infection by a pathogen, such as a virus. For example, when the compositions include a viral vector (e.g., an Ad5-based vector) that encodes an IFN (e.g., IFN-α, such as conIFN-α), at least about $1 \times 10^3$ viral particles (vp)/dose or between $1 \times 10^1$ and $1 \times 10^{14}$ vp/dose, preferably between $1 \times 10^3$ and $1 \times 10^{12}$ vp/dose, and more preferably between $1 \times 10^5$ and $1 \times 1011$ vp/dose (e.g., $1.5-3.0 \times 10^8$ vp/ml, of the viral vector provides a therapeutically effective amount of the IFN following expression in host cells. A single viral particle includes one or more nucleic acid molecules (either DNA or RNA) encoding viral and non-viral proteins (e.g., viral structural and non-structural proteins and including a non-endogenous IFN) and surrounded by a protective coat (e.g., a lipid-based envelope or a protein-based capsid) that includes protein subunits. Viral particle number can be measured based on, e.g., lysis of vector particles, followed by measurement of the absorbance at 260 nm (see, e.g., Steel, Curr. Opin. Biotech. 10:295-297, 1999).

When the composition is a non-viral vector that includes a nucleic acid molecule that encodes an IFN (e.g., IFN-α, such as conIFN-α), the subject should be administered at least about $1 \times 10^1$ molecules/dose, e.g., between $1 \times 10^1$ and $1 \times 10^{15}$ molecules/dose, preferably between $1 \times 10^3$ and $1 \times 10^{10}$ molecules/dose, and more preferably between $1 \times 10^4$ and $1 \times 10^8$ molecules/dose, of the non-viral delivery vector. A single nucleic acid molecule of a non-viral vector includes one or more nucleic acid molecules (e.g., DNA or RNA) in the form of, e.g., a plasmid, cosmid, yeast or bacterial artificial chromosome, and bacteriaphage that is administered in a naked form or that has been surrounded by or complexed with a protective substance (e.g., lipids or a lipid based envelope, peptides, and polymers).

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., epithelial cells, such as blood vessels epithelial cells, nasal epithelial cells, or pulmonary epithelial cells). The composition is preferably administered in an amount that provides a sufficient level of expression of IFN that elicits an immune response without undue adverse physiological effects in the host caused by the treatment.

In addition, single or multiple administrations of the compositions of the present invention may be given (pre- or post-exposure) to a subject (e.g., one administration or administration two or more times). For example, subjects who are particularly susceptible to, e.g., viral infection may require multiple treatments to establish and/or maintain protection against the virus. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against, e.g., a viral infection.

Alternatively, the efficacy of treatment can be determined by monitoring the level of IFN-α expressed in a subject (e.g., a human) following administration of the compositions of the invention (e.g., Ad5-IFN-α vectors). For example, the blood or lymph of a subject can be tested for IFN-α levels using, e.g., standard assays known in the art (see, e.g., Human Interferon-Alpha Multi-Species ELISA kit (Product No. 41105) and the Human Interferon-Alpha Serum Sample kit (Product No. 41110) from Pestka Biomedical Laboratories (PBL), Piscataway, N.J.). The efficacy of treatment can also be determined by monitoring the level of expression or activation of IFN-α upregulated factors, such as the double-stranded RNA (dsRNA)-dependent protein kinase R (PKR), the 2'-5'-oligoadenylate synthetase (2'-5'-OAS), IFN-inducible Mx proteins, a tryptophan-degrading enzyme (see, e.g., Pfefferkorn, Proc. Natl. Acad. Sci. USA 81:908-912, 1984), adenosine deaminase (ADAR1), IFN-stimulated gene 20 (ISG20), p56, ISG15, mGBP2, GBP-1, the APOBEC proteins, viperin, or other factors (see, e.g., Zhang et al., J. Virol., 81:11246-11255, 2007, and U.S. Pat. No. 7,442,527, which is incorporated by reference herein in its entirety).

A single intranasal dose of the compositions of the invention achieve protection, pre-exposure, from infectious agents (e.g., viral agents). This is a dramatic improvement from the several doses per week or even multiple daily doses that are required with current IFN-α treatments. In addition, a single dose administered directly post-exposure (e.g., within 24 hrs) to a viral or other infectious agent can function as a treatment according to the present invention. The effectiveness of a single dose of the compositions of the invention eliminates the need to track people to be treated and to retreat or revaccinate them, which is a difficult problem in a pandemic or bioterrorist attack where general panic typically ensues.

A single intranasal dose of the compositions of the invention can also be used to achieve therapy in subjects being treated for autoimmune disease or cancer. Multiple doses (e.g., 2, 3, 4, 5, or more doses) can also be administered, in necessary, to these subjects.

Shelf Stability

Pharmaceutical formulations of the compositions of the invention (e.g., a formulation that includes an Ad5-conIFN-α delivery vector) demonstrate a significant shelf life, which provides an advantage over other adenoviral, antiviral, or vaccine products. In particular, the Ad5-based IFN-α delivery vector of the invention, which can be manufactured and lyophilized (freeze-dried), exhibits a shelf-life of at least about 1, 2, 3, or 4 weeks, preferably at least about 1, 2, 3, 4, 5, 6, 12, or 18 months, more preferably at least 20 months, still more preferably at least about 22 months, and most preferably at least about 24 months when stored at room temperature. This is mission critical for the military and in developing countries where public health departments cannot guarantee refrigeration of medications. The shelf life of the compositions of the invention can be extended by storage at 4° C.

The shelf life of the adenoviral vector-containing compositions of the invention can be assessed by, e.g., determining adenoviral vector titers (see, e.g., Croyle et al., Gene Therapy 8:1281-1290, 2001) or by assessing the biological activity (e.g., the ability to transfect a cell and express biologically active IFN) of the IFN-containing delivery vehicle (e.g., viral or non-viral delivery vehicle). In an embodiment, the compositions of the invention exhibit a loss of less than 20% of the original titer (or biological activity), more preferably less than 10%, and most preferably less than 5%, after storage at room temperature for at least 12 months. In other embodiments, the compositions of the invention exhibit a loss of less than 40% of the original titer (or biological activity), more preferably less than 30%, and most preferably less than 20%, after storage at room temperature for at least 24 months.

Pharmaceutical formulations of the compositions of the invention also exhibit a shelf-life of at least about 1-15 days or 2-4 weeks or even at least about 2-6 months when stored at temperatures in the range of about 30° C. to about 55° C. (e.g., ~45° C.). In an embodiment, the composition is stored is a dry, unreconstituted powder form. Preferably, a composition of the invention that is stored at a temperature in the range of about 30° C. to about 55° C. exhibits a loss of less than 40% (more preferably less than 30%, 20%, or 10%, and most preferably less than 5%) of the original titer (or biological activity) when stored for a period of time in the range of 1 week to 2 months.

In another embodiment, pharmaceutical formulations of the compositions of the invention exhibit a shelf-life of at least about 1, 2, 3, or 4 weeks, preferably at least about 1, 2, 3, 4, 5, 6, 12, or 18 months, more preferably at least 20 months, still more preferably at least about 22 months, and most preferably at least about 24 months when stored frozen (e.g., at a temperature in the range of less than 4° C. (e.g., 0° C. to about −1900° C.)). In this embodiment, the composition can be stored as a non-stabilized, frozen liquid. Preferably, a composition of the invention that is stored at a temperature of less than 4° C. (e.g., 0° C. to about −20° C.) exhibits a loss of less than 40% (more preferably less than 30%, 20%, or 10%, and most preferably less than 5%) of the original titer (or biological activity) when stored for a period of time in the range of 2 months to 2 years.

Benefits of the long-term stability and shelf-life of the compositions of the invention include: a) ease of storage of the compositions as no cold chain is required, which increases the ability to disseminate and store the compositions in areas of the world that lack consistent access to electricity (e.g., third world economies and disaster or war zones) and improves military operational tempo as less "stuff" must be carried or used in areas without refrigeration; b) forward deployment is possible when the drug can be thrown in a soldier's backpack or in the back of a WHO disaster vehicle; c) less drug waste as losses due to thawing are mitigated; and d) more cost effective use of Strategic National Stockpile (SNS) storage space warehouse, which need not include refrigeration for storage of the compositions.

Figure 4:
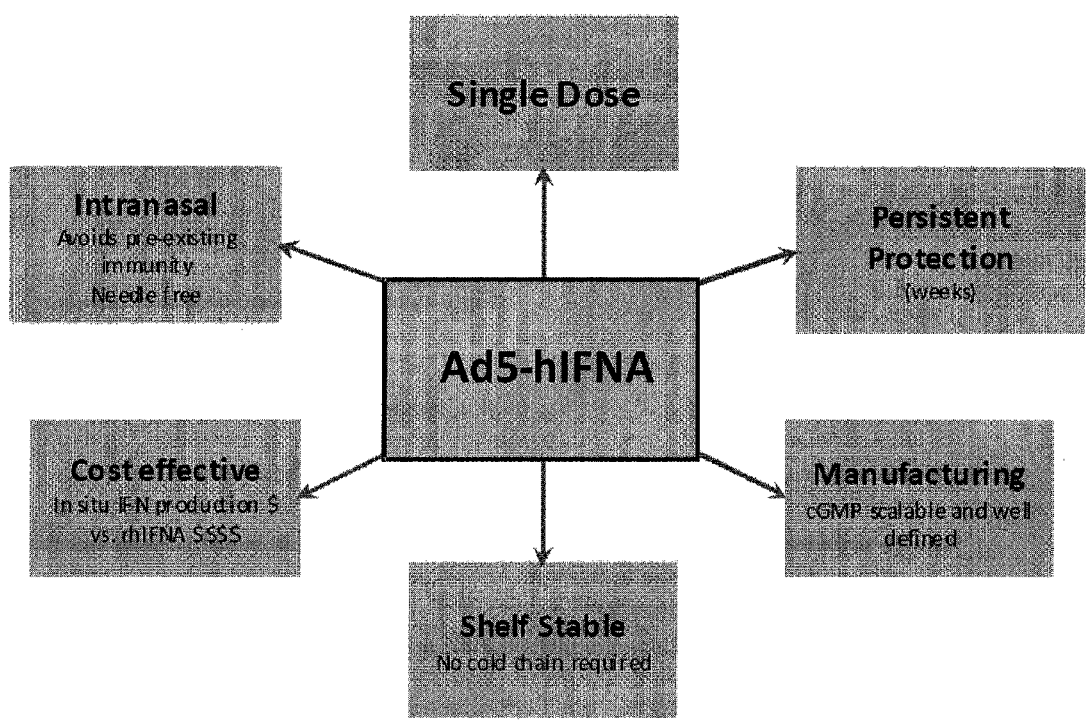
FIG. 4 is a diagram showing the benefits of an Ad5-con-IFN-α construct of the invention.

Other benefits of the Ad5-based IFN-α delivery vector of the invention are shown in FIG. 4.

Kits

The invention also provides kits including the IFN-α delivery vector of the invention, in lyophilized powder form, and a vial of hydration medium (e.g., sterile water or saline) that can be used to reconstitute the powder. In another embodiment, the kit includes a container of the IFN-α delivery vector of the invention, in lyophilized powder form, and a separate delivery device that can be combined with the container to allow release of the contents of the container during administration. The kit may also include a container of the IFN-α delivery vector of the invention, in lyophilized powder form, a vial of hydration medium (e.g., sterile water or saline) that can be used to reconstitute the powder, if desired, and a delivery device that can be used to release the IFN-α delivery vector as a powder or reconstituted liquid in an aerosolized form (e.g., via pulmonary or intranasal administration). Kits of the invention optionally include instructions for practicing any method described herein, including a therapeutic or prophylactic method, instructions for using any composition identified herein, and/or instructions for operating any apparatus, system, device, or component described herein, as well as packaging materials.

EXAMPLES

The following examples are to illustrate the invention. They are not meant to limit the invention in any way.

Example 1

Efficacy for Pre- and Post-Exposure Protection Against Western Equine Encephalitis Virus and Venezuelan Equine Encephalitis Virus The use of an Ad5-IFN-α delivery vector has been shown to provide both pre- and post-exposure protection against Western Equine Encephalitis virus (WEEV; Wu et al., Virology 369:206-213, 2007), an arthropod (mosquito) borne alphavirus classified as a Category B pathogen by the U.S. Centers for Disease Control (CDC). In this study, mice were inoculated with $10^7$ PFU of Ad5-mIFNA by intramuscular injection and challenged with various WEEV strains at a range of timepoints. The Ad5-mIFNA showed complete protection when administered 24 hr, 48 hr, and 1 week pre-exposure, and 38% protection when treated 13 weeks pre-exposure. A single inoculation at 6 hr after the challenge delayed the progress of WEEV infection and provided about 60% protection.

A study using Venezuelan Equine Encephalitis Virus (VEEV) yields similar results. VEEV is a more infections virus, and intramuscular administration of Ad5-IFN-α resulted in complete protection to 10LD50 when administered 24 hr pre-exposure (other time points were not tested), and 75% survival to 100LD50. In this case, Ad5-IFN did not protect when administered post-exposure (O'Brien et al., J. Gen. Virol. 90:874-882, 2009).

Example 2

Uses for the Compositions of the Invention

Pre-exposure (post-event) prophylaxis: The compositions of the invention can be used as a single administration broad-spectrum antiviral prophylactic medical countermeasure against, e.g., viral-based bioweapon threats or risk from exposure to endemic viral threats.

Military or Law Enforcement Operations

The compositions of the invention can be used as a prophylaxis for military, law enforcement agents, or local emergency coordinator (LEC) personnel who, during operations, are exposed to viral-based biological weapons threats. The decision to administer a composition of the invention (e.g., an Ad5 delivery vector that contains a nucleic acid molecule encoding conIFN-α, and that is formulated as a lyophilized powder for delivery to the nasal mucosa) to warfighters will be based on, e.g., a) the presence of identifiable biowarfare agents as measured by biosensors (as aerosols or surface contamination on equipment), b) intelligence that such viral-based weapons have been deployed or may be deployed by adversaries, or c) diseased sentinel animals, or d) contact by the warfighter with victims expected to present symptoms of viral disease.

Exposure During Research

A similar scenario is presented by researchers or manufacturers who, by the very nature of their jobs, come in regular contact with pathogenic viruses or other biological threats and for which an additional precaution against equipment or protocol failure. The compositions of the invention can be used as a prophylaxis (pre- or post-exposure) for these individuals, as well.

Example 3

Medical Chain

The compositions of the invention can be administered prophylactically to medical chain personnel, e.g., physicians, nurses, cleaning staff, and others who come into contact with patients suffering from viral or bacterial infectious diseases or who may have infectious diseases. The broad-spectrum nature of the compositions of the invention allows for administration to the subject before knowledge of the biological pathogen is available and in cases where there is no time to positively identify the viral pathogen. The compositions of the invention are also beneficial in cases where a virus mutates during a pandemic leaving the established vaccine ineffective or less protective.

Example 4

Public Health

Ring and Immediate Post Exposure Treatment

If a patient is known to have come in contact with a viral threat in the preceding 24 hrs, a composition of the invention (e.g., an Ad5 delivery vector that contains a nucleic acid molecule encoding IFN-α (e.g., conIFN-α), and that is formulated for nasal or pulmonary delivery, e.g., as an aerosolized powder or liquid mist) can be administered as a post-exposure treatment. If necessary, a composition of the invention can be administered, e.g., as a "ring" treatment to all susceptible individuals in a prescribed area around an outbreak of an infectious disease. Ring treatment controls an outbreak by treating and monitoring a ring of people around each infected individual.

Suspected Exposure Treatment

Even if exposure to a biological threat is not confirmed, a composition of the invention can be administered to those people thought to be exposed (the "worried well"), as the side effects of IFN are minimal. For example, a cranberry grower in Massachusetts is bitten by a mosquito and gets sick. For example, because there is an endemic risk of Eastern equine encephalitis (EEE), the person can be administered a composition of the invention, for example, by nasal or pulmonary delivery (e.g., as an aerosolized powder or liquid mist) and monitored for signs of improvement prior to agricultural work near cranberry bogs.

Post-Exposure Prophylaxis

On a population level, if dissemination of a viral threat is known or believed to have occurred, a composition of the invention can be administered, for example, by nasal or pulmonary delivery (e.g., as an aerosolized powder or liquid mist), stop the spread of the viral threat. In this case, the invervention is administered without knowing the infection status of the recipient, and thus the function of prophylaxis and treatment would likely be applied.

Example 5

Veterinary Indications of Ad5-Vectored IFN

The broad spectrum anti-viral capabilities of interferon polypeptide have been well recognized in veterinary medicine. Indeed, the oral administration of IFN is an effective treatment for shipping fever in thoroughbred race horses (Akai et al, J. Equine Sci. 19:91, 2008) and cattle experiencing bovine respiratory disease (BRDC; Cummins et al, J. Inf. & Cyto. Res. 19:907, 1999), and in the general treatment of respiratory illness in horses (Moore et al, Can. Vet. J. 45:594, 2004). Intranasal or pulmonary delivery of an Ad5-IFN could overcome the current limitations of repeated dosing and high cost. An intranasal delivery system for horses that could be used to administer compositions of the present invention is described in, e.g., U.S. Pat. No. 6,398,774, which is incorporated herein by reference. The use of an Ad5-IFN production system has been shown to be safe and effective in lab animals (see, e.g., Wu et al, Virology 369:206, 2007).

Other veterinary indications include the treatment or prevention of pandemics by pathogens, such as Rift Valley Fever, the treatment or prevention of endemic pathogens, and the treatment or prevention of pathogens that are released intentionally. The treatment or prevention in this context prevents or mitigates the potential catastrophic loss of animals within the food chain.

Example 6

Ad5-VEE/WEE/FEE Equine Vaccine

To date, vaccination is the only means of combating highly infectious, mosquito borne encephalitis alphaviruses. All horses in North America are at risk and vaccination is recommended. Currently marketed trivalent vaccines manufactured via traditional technology require multiple yearly injections and boosters to provide protection. A "live vaccine" approach using adenoviruses provides a safe means of producing a rapid and persistent protection using just a single intranasal administration.

Example 7

CoAdministration of Ad5-IFN with One or More Secondary Anti-Viral Drugs

The Ad5-IFN delivery vehicle (e.g., encoding conIFN-α or another IFN described herein) can be formulated with a pharmaceutically acceptable excipient for intranasal dosing in combination with an antihistamine and a neuraminidase inhibitor. This composition can be administered to a subject either prior to viral exposure or within 48 hours of exposure. The antihistamine helps to reduce any nasal congestion, e.g., stuffed or blocked nasal passages, caused by viral infection or rhinitis, thereby maximizing the distribution of the Ad5-IFN and neuraminidase inhibitor and their absorption by the epithelium of the upper and/or lower respiratory tract. An example of such an antihistamine would be H1 antagonists, such as fexofenadine or loratadine. A neuraminidase inhibitor, such as Zanamivir (Relenza®, GlaxoSmithKline), is a potent selective inhibitor of the viral neuraminidase glycoprotein that is important for viral replication of, e.g., influenza A and B and other viruses. The net effect of this three drug combination is improved viral prophylaxis where the IFN initiates a broad spectrum immune response, the neuraminidase inhibitor blocks viral release from infected cells, and the antihistamine ensures or improves delivery of the drugs to the nasal epithelium.

Alternatively, the Ad5-IFN delivery vector can be administered intranasally as a separate composition and the antihistamine and neuraminidase inhibitor (e.g., Oseltamivir phosphate (Tamiflu®, Roche Pharma)) can be administered orally in separate compositions or in a single composition (see, e.g., U.S. Pat. No. 6,605,302, which is incorporated herein by reference).

Example 8

Prophylaxis or Treatment of Punta Toro Virus

Family: Bunyaviridiae

Rift Valley fever virus (RVFV) is an arthropod-borne viral fever that causes direct infection in humans and livestock. The mode of transmission is via the bite of an infective *Aedes* or *Culex* mosquito. Mechanical infection via aerosols or infected blood has been reported in humans that work with, handle, or process livestock or contaminated carcasses. Humans of both sexes and all ages are susceptible and when infected with RVFV may develop retinitis, encephalitis, or hepatitis associated with hemorrhages that may be fatal (Heyman, Amercian Public Health Association, Washington D.C., 2008). Recent outbreaks in Kenya resulted in 118 deaths and a case fatality rate of 29% (CDC, Morb. Motal. Wkly. Rep. 56:73-76, 2007). There are no approved vaccines or effective therapies for RVFV. Reflecting the concern of public health officials, RVFV has been classified as a Category A pathogen by the National Institute for Allergic and Infectious Diseases and has received 'Dual Agent' status by the Department of Health and Human Services and the US Department of Agriculture.

Effective countermeasures that are highly stable, easily administered, and elicit long lasting protective immunity are much needed. Because direct work with RVFV is highly restricted and requires enhanced BSL-3+ facilities, we have recently established an intranasal (IN) respiratory route Punta Toro virus (PTV) infection model in Syrian Hamsters. PTV is a BSL-2 surrogate for RVFV, and produces disease in hamsters that models RVFV infection and disease progression in humans (Gowen et al., Antiviral Res. 77:215-224, 2008).

Figure 6:
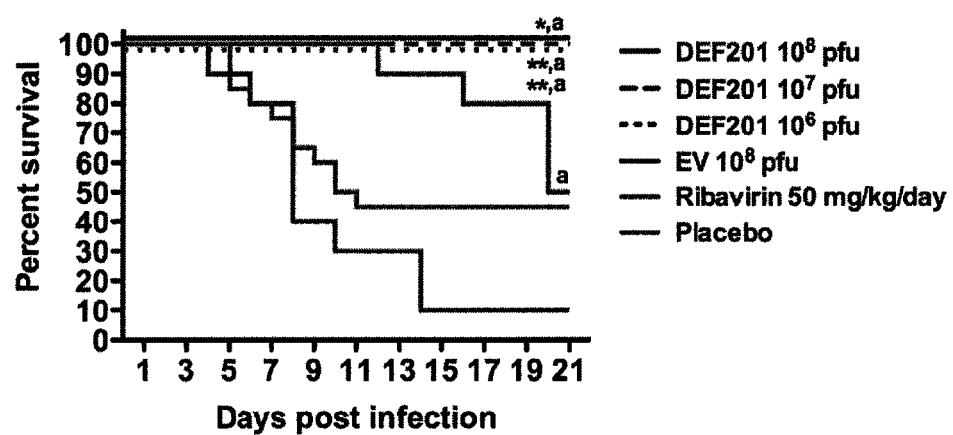
FIG. 6 is a graph showing the effect of intranasal (IN) Ad5-IFNα treatment on survival outcome in hamsters challenged with Punta Toro virus (PTV). Animals in each group were treated once 24 hours prior to IN instillation with PTV with the indicated amount of Ad5-IFNα or empty vector virus particles. Ribavirin treatment was i.p. once daily for 6 days starting 4 hours prior to PTV infection. *P<0.05, **P<0.01 compared to PBS vehicle placebo-treated animals. $^a$<0.001 as compared to EV-treated animals.

The purpose of this experiment was to evaluate Ad5-IFNα as a prophylactic agent to counter exposure to PTV. The route of Ad5-IFNα exposure was by intranasal (IN) to simulate respiratory mucosal surface delivery—a proposed route of administration in humans. Doses of $10^8$, $10^7$, and $10^6$ PFU of Ad5-IFNα (n=15) were administered 24 hrs prior to infectious challenge with PTV. The doses selected were based upon previous studies demonstrating high-level protection and were scaled to the hamster model based on typical dosing extrapolation equations using body surface area. As is shown in FIG. 6, administration of Ad5-IFNα at the indicated doses at least 24 hours prior to challenge with PTV resulted in 100% survival as compared to the ribavarin treated, empty-vector treated, and placebo controls.

In addition, we have demonstrated significant protection against both respiratory and subcutaneous PTV challenge infections in mice treated with Ad5-IFNα: a) prior to challenge as a prophylactic (up to 21 days before challenge) and b) as a treatment given up to +48 hr post-exposure.

Example 9

Prophylaxis or Treatment of Western Equine Encephalitis

Family: Togaviridae

Western Equine Encephalitis belongs to the *Alphavirus* genus of the Togavirus family which represents a group of mosquito borne, severely neuropathogenic, emerging pathogens in domestic animals and humans. WEEV is endemic to the Western portion of North America and is maintained in nature through a cycle involving wild birds as reservoir hosts and *Culex tarsalis* mosquitoes as vectors (Wu et al., Virology 369: 206-213, 2007) and have an overall case fatality rate of 3%-8% depending on age.

As a weapon, WEEV can be easily transmitted through the aerosol route with fatality rates as high as 40% in laboratory accidents (Hanson et al., Science 158: 1283-1286, 1967). A closely allied virus—Venezuelan Equine Encephalitis virus—was weaponized by the U.S. and the fowler Soviet Union for aerosol dissemination as an incapacitating agent on the battlefield. It was anticipated that a biological weapons attack in a region populated by Equines and mosquito vectors could initiate an epidemic (Eitzen et al., Medical Management of Biological Casualties 3$^{rd}$ Edition, published for the Department of Defense by The US. Army Medical Research Institute of Infectious Disease, Fort Detrick, Frederick Md., 1998). The ongoing concern of these viruses as an existing biological weapon and the lack of a safe and efficacious vaccine or antiviral has prompted public health concern, and these viruses are listed as a Category B Bioterrorist threat with the CDC (CDC, Centers for Disease Control and Prevention; Public Health Assessment of Potential Biological Terrorsm Agents Vol. 8, 2010).

One hundred forty (140) female Balb/c mice (10 per group) were used in this study and divided into two studies; each used a total of 70 mice. The first study tested the efficacy against WEEV California strain and the second study against WEEV CBA87 strain. The following treatment groups were used in both studies:

Groups 1-5: Single IN treatment with $10^7$ PFU Ad5-IFNα at Day (−21, −14, −7, −1 or +4 hrs respectively)
Group 6—IFNα B/D (recombinant mouse) $2 \times 10^7$ IU/kg once daily at Days 0 to 8, starting 4 hrs prior to challenge
Group 7—Control: untreated and challenged All mice were challenged intranasally on Day 0 with lethal dose of $2.5 \times 10^3$ pfu of WEEV California strain in study 1 and 500 pfu of WEEV CBA87 strain in study 2 and followed for 14 days for clinical signs of disease and euthanized at moribundity/morbidity. Administration of Ad5-IFNα (murine) resulted in complete protection of all animals in the prophylactic window, and 100% (California) & 70% (CBA87) survival in the +4 hrs treatment groups (FIGS. 7A and 7B).

Example 10

Prophylaxis or Treatment of Severe Acute Respiratory Syndrome

Family: Coronaviridae

SARS has recently emerged in the human population as a fatal respiratory disease. Severely affected patients develop acute respiratory distress syndrome, which corresponds with diffuse alveolar damage at autopsy. A newly discovered Coronavirus, SCV, has been identified as the primary cause of SARS. SARS patients have been treated empirically with a combination of Ribavirin, Oseltamivir, antibiotics and corticosteroids, with mixed results. Treatment with recombinant human interferon (Alfacon®) has shown clinical promise.

Groups of 10 mice were administered 50 μl of Ad5-IFNα (murine, $10^6$ PFU) IN once at 14, 7, 5, or 3 days pre-virus exposure (PVE). In addition, groups of 10 mice were administered 50 μl of Ad5-IFNα (murine) ($10^6$ PFU or $10^5$ PFU) IN one time at 6, 12, 24 hours post virus exposure. In both experiments Poly-ICLC was given at 1 mg/kg by the IN route at 24 h before virus exposure and 8 h after exposure to virus and served as a positive control for controlling the virus infection, and 15 mice were treated with buffered saline at each timepoint representing placebo controls. Animal deaths were recorded for up to 21 days post virus exposure.

As shown in FIGS. 8A and 8B, treatment with Ad5-IFNα (murine) resulted in complete protection of all animals in the treatment groups.

Example 11

Prophylaxis or Treatment of Yellow Fever Virus

Family: Flaviviridae

Yellow Fever (YF) is an acute infectious viral disease with a case fatality rate of 20-50% characterized by jaundice and hemorrhagic symptoms. YF is transmitted by mosquitoes, typically *Aede* spps in urban areas and *Haemogogus* spp or *Sabethes* spp in forests with humans or primates serving as reservoirs. YF has an endemic zone between 15° N and 10° S latitude which encompasses 33 African and nine South African and Caribbean Island with a combined population of >500 million people (Heymann, Control of Communicable Disease Manual, Amercian Public Health Association, Washington, D.C., 2008). While an effective vaccine is available, immunization coverage is variable, ranging from 30-95% in Africa. No approved treatment exists.

Hamsters were injected (15-20/group) intraperitoneally (IP) with 0.1 ml of the diluted virus (10 CCID$_{50}$/animal). Ad5-IFNα was administered by IN instillation at doses of $1 \times 10^8$, $5 \times 10^7$, $5 \times 10^6$, or $5 \times 10^5$ $1.25 \times 10^6$ PFU/animal one time at −4 h. Mortality was observed daily for 21 days, and weight was recorded on 0, 3, and 6 dpi. Liver tissue was taken at necropsy from 5 animals from each group for virus titration on 4 dpi. In a second study, animals were administered $5 \times 10^7$ PFU IN Ad5-IFNα at −4 hr, or +1, +2 or +3 days post infection (dpi) using the same controls as in the previous experiment.

Figure 9:
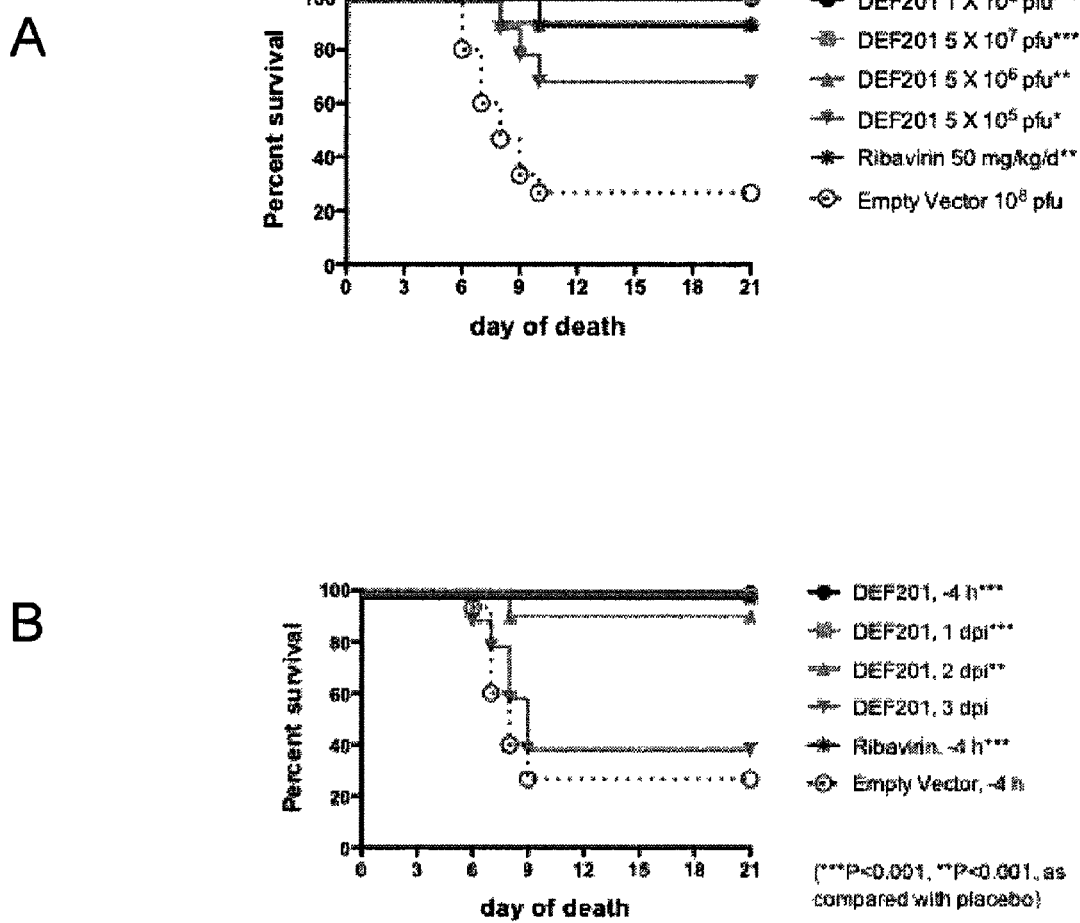
FIGS. 9A and 9B are graphs showing the effect of IN Ad5-IFNα treatment on survival outcome in mice challenged with YF virus.

Complete protection of hamsters was observed at the top two doses of $1 \times 10^8$ pfu and $5 \times 10^7$ pfu of Ad5-IFNα (FIG. 9A). A dose response was seen with increasing mortality occurring at lower doses, although survival was significantly improved in these groups over controls as well as a delay in the mortality curve. Overall, all of the Ad5-IFNα doses offered significant protection as compared with the empty adenovirus vector control with efficacy similar to or greater than that of the positive control. Using a dose of $5 \times 10^7$ PFU of Ad5-IFNα complete survival was seen with treatment at +1 d and 90% survival at +2 dpi (FIG. 9B).

Example 12

Treatment of Ebola Virus

Family: Filoviridae

Ebola hemorrhagic fever was first recognized in 1976 in two simultaneous outbreaks in Sudan and Zaire which affected >600 people with case fatality rates of 55% and 90% respectively. Person-to-person contact does occur through direct contact with blood, secretions, organs, or semen from infected humans. Nosocomial infections are frequent, and virtually all persons infected from contaminated needles died. Despite extensive study, the natural animal reservoir for Ebola remains unknown. There are no approved vaccines or effective treatments for Filovirus infections (Heymann, Control of Communicable Disease Manual, Amercian Public Health Association, Washington, D.C., 2008).

Ebola virus is considered a Category A bioterrorism agent by the CDC (CDC, 2010, supra) and top priority public health biological threat (PHEMCE, Public Health Emergency Medical Countermeasures Enterprise, Health & Human Services, Washington D.C., 2007). Such agents pose a risk to national security because they can be easily disseminated or transmitted from person to person; result in high mortality rates and have the potential for major public health impact and require special action for public health preparedness.

Here, Ad5-IFNα was tested in mouse and Guinea pig models of the Ebola virus, Zaire strain (ZEBOV). Groups of 10 mice were challenged by intraperitoneal (IP) injection with $1000 \times LD_{50}$ of the mouse-adapted Ebola virus. Thirty minutes later they were dosed by either the IM (50 µl per each hind limb) or IN (50 µl) route with a single dose of $1 \times 10^7$ IFU (infectious units) mAd5-IFNα per mouse. Control mice were injected IM with phosphate buffered saline (PBS) (50 µl per each hind limb). Complete survival benefit was seen with administration of mouse mAd5-IFNα by either route, and there was no significant weight loss in treated groups versus control (FIG. 10A).

Following the success of the mouse study, Ad5-IFNα was tested in a Guinea Pig (GP) model of Ebola virus, Zaire strain (ZEBOV). The GP model more closely mimics the pathophysiology of the disease in humans, and the animals are more susceptible to challenge, thus making it a more difficult model to achieve positive results. Eight Hartley guinea pigs were challenged by IP injection with $100 \times LD_{50}$ of guinea pig-adapted ZEBOV. 30 minutes later two animals were dosed IN with $2 \times 10^8$ PFU Ad5-IFNα per guinea pig. In addition, recombinant IFN protein was administered to three GPs daily for six days to assess the therapeutic potential of the protein alone, while three animals were untreated and served as a negative control group. All of the animals treated with Ad5-IFNα survived, compared to 66% in the interferon protein group, whereas all the control animals perished (FIG. 10B).

Example 13

Prophylaxis for Pichinde Virus

Family: Arenaviridae

Arenaviruses produce an acute viral illness which progresses in 20% of patients to severe multisystem disease with hospitalized case fatality rate up to 15%. The disease is severe in pregnancy with fetal loss rates approaching 80% and associated frequent maternal death. Arenaviruses are serologically divided into Old World (e.g. Lassa fever) and New World (e.g. Machupo or Junin). Lassa fever has had the greatest impact on public health by hemorrhagic fever, with more than 100,000 endemic infections in West Africa and 5,000 deaths annually (Fischer-Hoch et al., J. Virol. 74:6777-6783, 2000). The mode of transmission is through aerosol or direct contact with contaminated rodent excreta or via person-to-person by pharyngeal secretions, semen or urine.

Arenaviruses are considered a Category A bioterrorism agent by the CDC (CDC, 2010, supra) and a priority public health biological weapons threat (PHEMCE, 2007, supra). Such agents pose a risk to national security because they can be easily disseminated or transmitted from person to person; result in high mortality rates and have the potential for major public health impact and require special action for public health preparedness. Pichinde virus (PCV) is a New World Arenavirus that is highly pathogenic in hamsters but is non-pathogenic in humans (Buchmeier et al., Infect. Immun. 9:821-823, 1974). PCV infection in hamsters is a well characterized animal model that produces a fulminating disease that ends in terminal shock via vascular leakage syndrome with high systemic viral titers. The distribution of viral antigens within the infected host (Connolly et al., A. J. Trop. Med. Hyg. 4; 10-24, 1993) mimics the disease manifestations reported in human Arenavirus cases (Walker et al., Am. J. Path. 107:349-356, 1982) but can be utilized safely under BSL-2 conditions (Gowen and Holbrook, Antiviral Res. 78:79-90, 2007).

Figure 11:
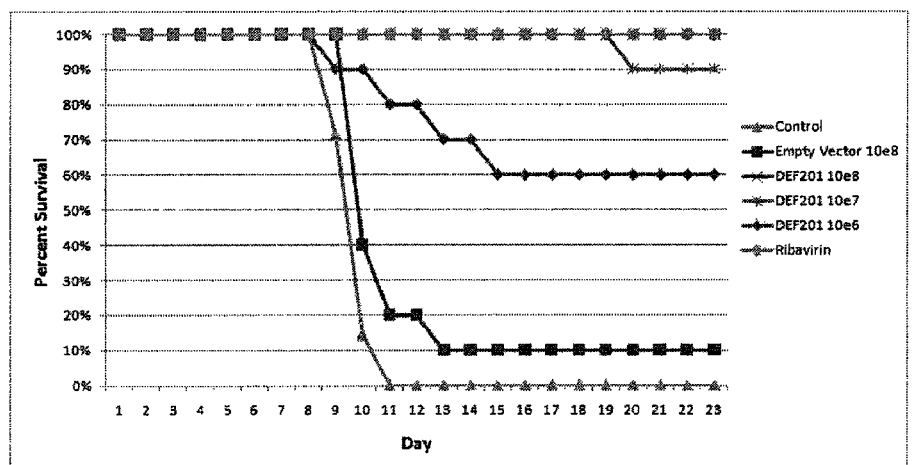
FIG. 11 is a graph showing the effect of IN Ad5-IFNα treatment on survival outcome in mice challenged with Pichinde virus. Animals were treated with Ad5-IFNα, as per the groups outlined in Example 13 below, and challenged with PCV via IN instillation. Complete protection was observed at the highest dose, with a dose response curve at lower doses.

Ad5-IFNα was tested in a hamster model of Pichinde virus infection. One day prior to challenge, groups of 10 animals were dosed via the IN route (200 µl) with a single dose of either: $10^8$, $10^7$, or $10^6$ PFU Ad5-IFNα per hamster. Animals were challenged by intraperitoneal (IP) injection with $LD_{95}$ of the hamster-adapted PCV. Control mice were dosed IN with phosphate buffered saline (PBS) (100 µl per nostril). Complete survival benefit was seen with administration of Ad5-IFNα at the highest dose, with a dose dependent decline in survival seen at lower levels (FIG. 11).

Example 14

Treatment with a Combination "Instant Acting Vaccine" for Ebola

Family: Filovirus

Ad5-IFNα Administered in Conjunction with a Vaccine

Vaccines have been a cornerstone for effective infectious disease prevention since Jenner in 1796. Vaccines are cost-effective, easily administered, generally safe and longlasting. However, when facing bioweapons threats, broad nationwide vaccine campaigns have met with considerable opposition. The bias against vaccination arises from the public's balancing of the risk from a low-probability bioweapons threats vs the certainty of adverse vaccine effects in a few patients. Indeed, even the smallpox vaccination campaign which boasted the first and only infectious disease ever irradicated, was discontinued some 30 years ago despite Presidential support for police and healthcare worker vaccination. A second public health issue is the time delay. Vaccines work slowly—often requiring 7 to 21 days—for a vaccination and boosters to achieve protection. This time delay has lethal consequences for most pathogenic viral bioweapon infections. As such, current public health vaccination strategies and stockpiles are directed toward disease mitigation and prevention of secondary infection and disease spread. Infected individuals at ground zero receive only supportive care. We propose the use of Ad5-IFNα AND a vaccine to radically change this disease management paradigm to include treatment AND prophylaxis. Further, existing vaccine stockpiles can now be repurposed and utilized as part of an "instant acting vaccine".

It is clear that Ad5-IFNα can act as a both a prophylactic and a treatment. In this example, we combine Ad5-IFNα—acting as a type of adjuvant—with a standard vaccine to form an "Instant Acting Vaccine". The benefits of this approach are significant. Ad5-IFNα functions as an immune system stimulant, with the following benefits; a) administration of Ad5-IFNα with a vaccine can protect the host against the viral insult until the vaccine is functional and b) Ad5-IFNα can stimulate the immune system to respond to the vaccine faster or more vigorously and thus establish protective antibody levels faster.

Figure 12:
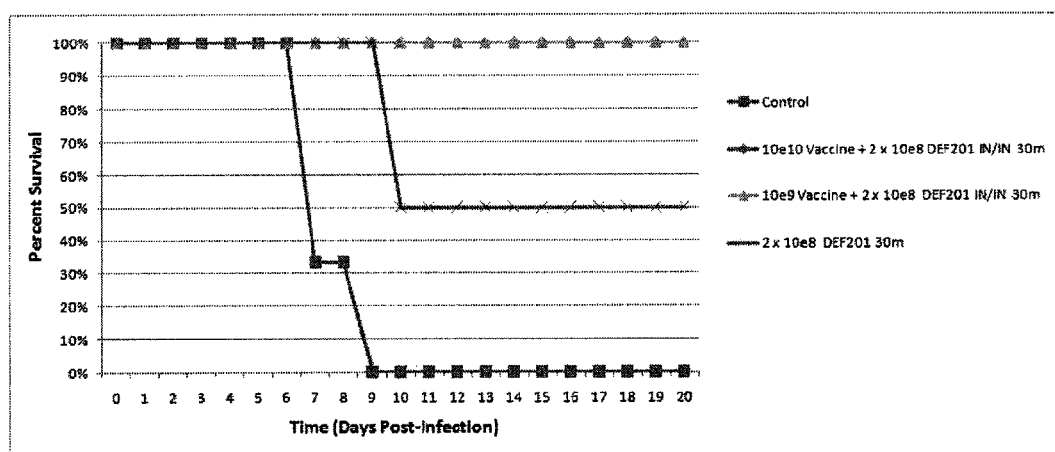
FIG. 12 is a graph showing the effect of IN Ad5-IFNα treatment in conjunction with Ad-EBOV vaccine on survival outcome in mice challenged with EBOV. Animals were treated with Ad5-IFNα, as per the groups outlined in Example 14 below, and challenged with PCV via IN instillation. Complete protection was observed at the highest dose, with a dose response curve at lower doses.

In the case of Ebola, we administered an Ad5-IFNα in conjunction with an Ad5 vectored Ebola glycoprotein vaccine (Ad-CAGoptZGP; vaccine described Richardson et al, 2009, supra; Croyle et al, PLoS 3:1-9, 2008) to demonstrate the method and benefit of the instant acting vaccine. Six Guinea pigs were administered the vaccine ($10^9$ or $10^{10}$ infectious units) with Ad5-IFNα ($2\times10^8$ PFU) via IN administration 30 minutes after a 1000LD50 challenge with ZEBOV. These combined treatments resulted in 100% survival of the animals (FIG. 12). Ad5-IFNα alone was able to save 50% of the challenged animals and the vaccine alone was only able to save 30% in a model with $1/10^{th}$ the challenge. Thus, the two components work synergistically to save animals that each component could not save separately from challenge with Ebola.

Given this data, Ad5-IFNα has tremendous potential to serve as a vaccine adjuvant for a wide range of vaccines, thereby speeding the time to protection in either a prophylactic or treatment model.

Example 15

Vaccine Stability

We have developed a rugged, shelf stable formulation of the combination therapy, Ad5-IFNα+Ad-CAGoptZGP. Our preliminary data illustrates Ad5 vector stability with no appreciable loss in activity at 37° C. for 84 days, and at 100° C. for at least an hour (ASM 2010).

Example 16

Safety Data

There is a wealth of clinical data showing that the Ad5 vector system and recombinant human IFN, separately, are safe (including when administered using multiple repeat dosing). In addition, Ad-CAGoptZGP alone has been used successfully to treat a suspected Ebola infection of a lab worker in Germany. The patient experienced a fever and headache commonly associated with antiviral vaccines, but made a full recovery.

The doses of Ad5-IFNα+Ad-CAGoptZGP as evaluated in the mouse and guinea pig ZEBOV models discussed above demonstrate safety at even the highest expected doses. Our experience to date indicates superior efficacy even at lower doses of Ad5-IFNα (as low 1/1000th) used in animal models of other diseases (e.g. Punta Toro, WEE, and SARS). This result, coupled with the synergistic relationship of the 2 components (Ad5-IFNα+Ad-CAGoptZGP) indicates that a lower dose should be substantially effective against infection by a pathogen, such as, e.g., an Ebola infection.

To date, more than 60 clinical trials have been conducted with Ad5 as the gene delivery vector, thus providing a solid toxicology framework for Ad5-IFNα-containing compositions of the invention (including, e.g., the combination of Ad5-IFNα and Ad-CAGoptZGP). For example, in humans a dosage in the range of $1.0\times10^6$ to $1.0\times10^{12}$ (e.g., $1.6\times10^9$ PFU) for a 70 kg person for the combination of Ad5-IFNα and Ad-CAGoptZGP is expected to provide therapeutic and prophylactic benefit against challenge or exposure to a pathogen (e.g., a viral agent). In our animal model studies, we have tested the combination of Ad5-IFNα and Ad-CAGoptZGP at a viral particle (vp) to PFU ratio of 10:1 with success. For example, with regard to a viral particle (vp) to PFU ratio of 50:1, which is expected to be at the higher end of the administration spectrum, the dose will be $8\times10^{10}$ vp.

Safety of Replication Defective Ad5 Vectors

The safety of replication defective Ad5 vectors has been confirmed during a dose escalation study involving 12 patients where the Ad5 was delivered intranasally ($2\times10^7$-$2\times10^{10}$ PFU/patient; see Knowles et al., N.E. J. Med. 333:823-831, 1995). At the highest dose, adverse effects were deemed moderate (ear ache and mucosal sensitivity) and were resolved within three weeks. More recently, a pilot Phase I safety study noted dose limiting toxicology at $2\times10^{12}$ vp, with repeated doses of the Ad5 vector being well tolerated (see Keedy et al., J. Clin. Oncol. 26:4166-4171, 2008). The NIH Recombinant DNA Advisory Committee (NIH Report, Hum. Gene Ther. 13:3-13, 2002) reports the upper safe limit before toxicology of replication defective Ad5 vectors as $7\times10^{13}$ vp. Using these studies as precedents, we expect the effective dose of a combination therapy, such as Ad5-IFNα and Ad-CAGoptZGP, would be at least 1-2 orders of magnitude lower than the low safe dose threshold for Ad5 administration.

Safety of Interferons

Interferons are safely used clinically to treat Hepatitis C and SARS, where the high dose side effects can be flu like symptoms such as increased body temperature, headache, muscle pain, convulsion, and dizziness. In some cases hair thinning and depression has also been observed. In cases of high risk melanoma the maximum tolerated dose was used ($4.5\times10^5$ U/kg) daily for one month (see Jonasch et al., Cancer J. 6:1390145, 2000), followed by a half dose three times a week for 48 weeks. The resultant level of IFN in the bloodstream for 12 hours post injection can be extrapolated as approximately 230 U/mL (see Cantell et al., J. Gen. Virol. 22:453-455, 1974). The level of serum IFN measured in our mouse model was 250 U/mL (see Wu et al., Virology 369: 206-213, 2007). Again, this comparison illustrates that our maximum expected dose produces a serum IFN level that is consistent with those found in patients undergoing antiviral therapy.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated as being incorporated by reference in their entirety. Also incorporated by reference is PCT/CA2010/000844, entitled "ADMINISTRATION OF INTERFERON FOR PROPHYLAXIS AGAINST OR TREATMENT OF PATHOGENIC INFECTION," which was filed on Jun. 9, 2010, naming Jeffrey D. Turner and Jane E. Ennis as inventors.

APPENDIX

Interferon Alpha 1b - IFNA1
Nucleotide: NCBI Reference Sequence: NM_024013.1 *Homo sapiens*

(SEQ ID NO: 1)

```
  1 agaacctaga gcccaaggtt cagagtcacc catctcagca agcccagaag tatctgcaat
 61 atctacgatg gcctcgccct ttgctttact gatggtcctg gtggtgctca gctgcaagtc
121 aagctgctct ctgggctgtg atctccctga acccacagc ctggataaca ggaggacctt
181 gatgctcctg cacaaatga gcagaatctc tccttcctcc tgtctgatgg acagacatga
241 ctttggattt ccccaggagg agtttgatgg caaccagttc cagaaggctc cagccatctc
301 tgtcctccat gagctgatcc agcagatctt caacctcttt accacaaaag attcatctgc
361 tgcttgggat gaggacctcc tagacaaatt ctgcaccgaa ctctaccagc agctgaatga
421 cttggaagcc tgtgtgatgc aggaggagag ggtgggagaa actcccctga tgaatgcgga
481 ctccatcttg gctgtgaaga aatacttccg aagaatcact ctctatctga cagagaagaa
541 atacagccct tgtgcctggg aggttgtcag agcagaaatc atgagatccc tctctttatc
601 aacaaacttg caagaaagat taggaggaa ggaataacat ctggtccaac atgaaaacaa
661 ttcttattga ctcatacacc aggtcacgct tcatgaatt ctgtcatttc aaagactctc
721 acccctgcta aactatgac catgctgata aactgattta tctatttaaa tatttattta
781 actattcata agatttaaat tattttgtt catataacgt catgtgcacc tttacactgt
841 ggttagtgta ataaaacatg ttccttatat ttactc
```

Amino Acid: NCBI Reference Sequence: NP_076918.1 *Homo sapiens*

(SEQ ID NO: 2)

```
  1 maspfallmv lvvlsckssc slgcdlpeth sldnrrtlml laqmsrisps sclmdrhdfg
 61 fpqeefdgnq fqkapaisvl heliqqifnl fttkdssaaw dedlldkfct elyqqlndle
121 acvmqeervg etplmnadsi lavkkyfrri tlyltekkys pcawevvrae imrslslstn
181 lqerlrrke
```

Interferon Alpha 2b - IFNA2
Nucleotide: NCBI Reference Sequence: NM_000605.3 *Homo sapiens*

(SEQ ID NO: 3)

```
   1 gagaacctgg agcctaaggt ttaggctcac ccatttcaac cagtctagca gcatctgcaa
  61 catctacaat ggccttgacc tttgctttac tggtggccct cctggtgctc agctgcaagt
 121 caagctgctc tgtgggctgt gatctgcctc aaacccacag cctgggtagc aggaggacct
 181 tgatgctcct ggcacagatg aggagaatct ctcttttctc ctgcttgaag gacagacatg
 241 actttggatt tccccaggag gagtttggca accagttcca aaaggctgaa accatccctg
 301 tcctccatga tgatccag cagatcttca tctcttcag cacaaaggac tcatctgctg
 361 cttgggatga gaccctccta gacaaattc acactgaact ctaccagcag ctgaatgacc
 421 tggaagcctg tgtgatacag ggggtggggg tgacagagac tcccctgatg aaggaggact
 481 ccattctggc tgtgaggaaa tacttccaaa gaatcactct ctatctgaaa gagaagaaat
 541 acagcccttg tgcctgggag gttgtcagag cagaaatcat gagatctttt tctttgtcaa
 601 caaacttgca agaaagttta agaagtaagg aatgaaaact ggttcaacat ggaaatgatt
 661 ttcattgatt cgtatgccag ctcaccttt tatgatctgc catttcaaag actcatgttt
 721 ctgctatgac catgacacga tttaaatctt tcaaatgtt tttaggagta ttaatcaaca
 781 ttgtattcag ctcttaaggc actagtccct tacagaggac catgctgact gatccattat
 841 ctatttaaat atttttaaaa tattatttat ttaactattt ataaaacaac ttatttttgt
 901 tcatatattg tcatgtgcac cttttgcacag tggttaatgt aataaaatat gttctttgta
 961 tttggtaaat ttatttgtg ttgttcattg aactttgct atgaaacttt tgtacttgt
1021 ttattcttta aaatgaaatt ccaagcctaa ttgtgcaacc tgattacaga ataactggta
1081 cacttcatttt atccatcaat attatattca agatataagt aaaaataaac tttctgtaaa
1141 cca
```

Amino Acid: NCBI Accession No. AAP20099 *Homo sapiens*

(SEQ ID NO: 4)

```
  1 mcdlpqthsl gsrrtlmlla qmrrislfsc lkdrhdfgfp
 41 qeefgnqfqk aetipvlhem iqqifnlfst kdssaawdet
 81 lldkfytely qqlndleacv iqgvgvtetp lmkedsilav
121 rkyfqritly lkekkyspca wevvraeimr sfslstnlqe
161 slrske
```

Interferon Beta 1a - IFNB1
Nucleotide: NCBI Reference Sequence: NM_002176.2 *Homo sapiens*

(SEQ ID NO: 5)

```
  1 acattctaac tgcaaccttt cgaagccttt gctctggcac aacaggtagt aggcgacact
 61 gttcgtgttg tcaacatgac caacaagtgt ctcctccaaa ttgctctcct gttgtgcttc
121 tccactacag ctctttccat gagctacaac ttgcttggat tcctacaaag aagcagcaat
181 tttcagtgtc agaagctcct gtggcaattg aatgggaggc ttgaatactg cctcaaggac
241 aggatgaact ttgacatccc tgaggagatt aagcagctgc agcagttcca gaaggaggac
301 gccgcattga ccatctatga gatgctccag aacatctttg ctattttcag acaagattca
361 tctagcactg gctggaatga ctattgttg agaacctcc tggctaatgt ctatcatcag
421 ataaaccatc tgaagacagt cctggaagaa aaactggaga agaagatttt caccagggga
481 aaactcatga gcagtctgca cctgaaaaga tattatggga ggattctgca ttacctgaag
541 gccaaggagt acagtcactg tgcctggacc atagtcagag tggaaatcct aaggaacttt
601 tacttcatta acagacttac aggttacctc cgaaactgaa gatctcctag cctgtgcctc
661 tgggactgga caattgcttc aagcattctt caaccagcag atgctgttta agtgactgat
721 ggctaatgta ctgcatatga aggacactg aagattttg aaattttat taaattatga
781 gttattttta tttatttaaa ttttatttg gaaaataaat tattttggt gcaaaagtca
```

APPENDIX-continued

Amino Acid: NCBI Reference Sequence: NP_002167.1 *Homo sapiens*

(SEQ ID NO: 6)
```
  1 mtnkcllqia lllcfsttal smsynllgfl qrssnfqcqk llwqlngrle yclkdrmnfd
 61 ipeeikqlqq fqkedaalti yemlqnifai frqdssstgw netivenlla nvyhqinhlk
121 tvleekleke dftrgklmss lhlkryygri lhylkakeys hcawtivrve ilrnfyfinr
181 ltgylrn
```

Interferon Gamma - IFNG
Nucleotide: NCBI Reference Sequence: NM_000619.2 *Homo sapiens*

(SEQ ID NO: 7)
```
   1 cacattgttc tgatcatctg aagatcagct attagaagag aaagatcagt taagtccttt
  61 ggacctgatc agcttgatac aagaactact gatttcaact tctttggctt aattctctcg
 121 gaaacgatga aatatacaag ttatatcttg gcttttcagc tctgcatcgt tttgggttct
 181 cttggctgtt actgccagga cccatatgta aaagaagcag aaaaccttaa gaaatatttt
 241 aatgcaggtc attcagatgt agcggataat ggaactcttt tcttaggcat tttgaagaat
 301 tggaaagagg agagtgacag aaaaataatg cagagccaaa ttgtctcctt ttacttcaaa
 361 cttttttaaaa actttaaaga tgaccagagc atccaaaaga gtgtggagac catcaaggaa
 421 gacatgaatg tcaagttttt caatagcaac aaaaagaaac gagatgactt cgaaaagctg
 481 actaattatt cggtaactga cttgaatgtc aacgcaaag caatacatga actcatccaa
 541 gtgatggctg aactgtcgcc agcagctaaa acagggaagc gaaaaggag tcagatgctg
 601 tttcgaggtc gaagagcatc ccagtaatgg ttgtcctgcc tgcaatattt gaattttaaa
 661 tctaaatcta tttattaata tttaacatta tttatatggg gaatatattt ttagactcat
 721 caatcaaata agtatttata atagcaactt ttgtgtaatg aaaatgaata tctattaata
 781 tatgtattat ttataattcc tatatcctgt gactgtctca cttaatcctt tgttttctga
 841 ctaattaggc aaggctatgt gattacaagg ctttatctca ggggccaact aggcagccaa
 901 cctaagcaag atcccatggg ttgtgtgttt atttcacttg atgatacaat gaacacttat
 961 aagtgaagtg atactatcca gttactgccg gtttgaaaat atgcctgcaa tctgagccag
1021 tgctttaatg gcatgtcaga cagaacttga atgtgtcagg tgaccctgat gaaaacatag
1081 catctcagga gatttcatgc ctggtgcttc caaatattgt tgacaactgt gactgtaccc
1141 aaatggaaag taactcattt gttaaaatta tcaatatcta atatatatga ataaagtgta
1201 agttcacaac aaaaaaaaaa aaaaaaaaaa aaaaaaaaaa
```

Amino Acid: NCBI Reference Sequence: NP_000610.2 *Homo sapiens*

(SEQ ID NO: 8)
```
  1 mkytsyilaf qlcivlgslg cycqdpyvke aenlkkyfna ghsdvadngt lflgilknwk
 61 eesdrkimqs qivsfyfklf knfkddqsiq ksvetikedm nvkffnsnkk krddfekltn
121 ysvtdlnvqr kaiheliqvm aelspaaktg krkrsqmlfr grrasq
```

Interferon Tau - IFNT
Nucleotide: NCBI Reference Sequence: NM_001015511.2 *Bos taurus*

(SEQ ID NO: 9)
```
   1 gatccccgga aactagaatt cacctgaagg ttcacccaga ccccatctca gccagcccag
  61 cagcagccac atcttcccca tggccttcgt gctctctcta ctgatggccc tggtgctggt
 121 cagctacggg cagggacgat ctctgggttg ttacctgtct gaggaccaca tgctaggtgc
 181 cagggagaac ctcaggctcc tggcccgaat gaacagactc tctcctcatc cctgtctgca
 241 ggacagaaaa gactttggtc ttcctcagga gatggtggag ggcaaccagc tccagaagga
 301 tcaggctatc tctgtgctcc acgagatgct ccagcagtgc ctcaacctct ctacacaga
 361 gcactcgtct gctgcctgga acaccaccct cctggagcag ctctgcactg gctccaaca
 421 gcagctggag gacctggacg cctgcctggg cccagtgatg ggagagaaag actctgacat
 481 gggaaggatg ggccccattc tgactgtgaa gaagtacttc cagggtatcc atgtctacct
 541 gaaagaaaaa gaatacagtg actgcgcctg ggaaatcatc agagtggaga tgatgagagc
 601 cctctcttca tcaaccacct tgcaaaaaag gttaagaaag atgggtggag atctgaactc
 661 actttgagat gactctcgct gactaagatg ccacatcacc ttcgtacact cacctgtgtt
 721 catttcagaa gactctgatt tctgcttcag ccaccgaaat cattgaatta ctttaactga
 781 tactttgtca gcagtaataa gcaagtagat ataaaagtac tcagctgtag gggcatgagt
 841 ccttaagtga tgcctgccct gatgttatct gttgttgatt tatgtattcc ttcttgcatc
 901 taacatactt aaaatattag gaaatttgta aagttacatt tcatttgtac atcatattaaa
 961 atttctaaaa catgtttacc attttgtgtt attaaatttg tcctttgttc tatttattaa
1021 atcaaagaaa atc
```

Amino Acid: GenBank: AAK53058.1 *Bos taurus*

(SEQ ID NO: 10)
```
  1 mkytsyilaf qlcivlgslg cycqdpyvke aenlkkyfna ghsdvadngt lflgilknwk
 61 eesdrkimqs qivsfyfklf knfkddqsiq ksvetikedm nvkffnsnkk krddfekltn
121 ysvtdlnvqr kaiheliqvm aelspaaktg krkrsgmlfr grrasq
```

Consensus Interferon (conIFN-α)
Amino Acid:

(SEQ ID NO: 11)
```
  1 cdlpqthslg nrralillaq mrrispfscl kdrhdfgfpq eefdgnqfqk aqaisvlhem
 61 iqqrfnlfst kdssaawdes llekfytely qqlndleacv iqevgveetp lmnvdsilav
121 kkyfqritly ltekkyspca wevvraeimr sfslstnlqe rlrrke
```

What is claimed is:

1. A method for treating or reducing the effects of an infection in a human subject in need thereof comprising administering an amount of a composition comprising an adenoviral vector comprising a nucleic acid molecule encoding interferon-alpha (IFN-α) to the pulmonary or nasal mucosa of the subject one or more times, wherein said infection is not caused by an alphavirus and wherein said administration achieves systemic circulation of said IFN-α in the blood of said human 2. The method of claim 1, wherein administration of said composition results in expression of said IFN-α in pulmonary or nasal epithelial cells of said mucosa.

3. The method of claim 1, wherein said IFN-α is consensus IFN-α (conIFN-α).

4. The method of claim 1, wherein said subject receives said composition prior to or after exposure to a pathogen that causes said infection.

5. The method of claim 4, wherein said subject receives said composition at least 15 minutes to at least 1 week prior to exposure to said pathogen.

6. The method of claim 4, wherein said subject receives said composition immediately after exposure to said pathogen or at least 15 minutes to at least 2 weeks after exposure to said pathogen.

7. The method of claim 1, wherein said infection is caused by a pathogen selected from the group consisting of a bacterium, virus, fungus, and parasite.

8. The method of claim 7, wherein:
i) said bacterium is selected from *Pseudomonas aeruginosa, Salmonella typhimurium, Escherichia coli, Klebsiella pneumoniae, Bruscella, Burkholderia mallei, Yersinia pestis*, and *Bacillus anthraci;*
ii) said virus is selected from a member of the Flaviviridae, Arenaviridae, Bunyaviridae, Filoviridae, Togaviridae, Poxyiridae, Herpesviridae, Orthomyxoviridae, Coronaviridae, Rhabdoviridae, Paramyxoviridae, Picornaviridae, Hepadnaviridae, Papillamoviridae, Parvoviridae, Astroviridae, Polyomaviridae, Calciviridae, Reoviridae, and the Retroviridae family;
iii) said fungus is selected from *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, and *Rhizopus arrhizus;* or
iv) said parasite is selected from *Toxoplasma gondii, Plasmodium falciparum, P. vivax, P. ovale, P. malariae, Trypanosoma* spp., and *Legionella* spp.

9. The method of claim 8, wherein said virus is selected from hepatitis C virus, Yellow fever virus, Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus, Negishi virus, Meaban virus, Saumarez Reef virus, Tyuleniy virus, Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, Cell fusing agent virus, Ippy virus, Lassa virus, lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, Lujo virus, Hantaan virus, Sin Nombre virus, Dugbe virus, Bunyamwera virus, Rift Valley fever virus, La Crosse virus, Punta Toro virus (PTV), California encephalitis virus, Crimean-Congo hemorrhagic fever (CCHF) virus, Ebola virus, Marburg virus, rubella virus, smallpox virus, monkeypox virus, vaccinia virus, herpes simplex virus (HSV), human herpes virus, cytomegalovirus (CMV), Epstein-Barr virus (EBV), Varicella-Zoster virus, Kaposi's sarcoma associated-herpesvirus (KSHV), influenza virus, severe acute respiratory syndrome (SARS) virus, rabies virus, vesicular stomatitis virus (VSV), human respiratory syncytial virus (RSV), Newcastle disease virus, hendravirus, nipahvirus, measles virus, rinderpest virus, canine distemper virus, Sendai virus, human parainfluenza virus, rhinovirus, mumps virus, coxsackievirus, hepatitis B virus, human papilloma virus, adeno-associated virus, astrovirus, JC virus, BK virus, SV 40 virus, Norwalk virus, rotavirus, human immunodeficiency virus (HIV), and human T lymphotropic virus (HTLV).

10. The method of claim 1, wherein said composition is administered as a dry, lyophilized powder.

11. The method of claim 1, wherein said composition is admixed with a pharmaceutically acceptable liquid and inhaled as an aerosolized mist.

12. The method of claim 11, wherein said pharmaceutically acceptable liquid is water or saline.

13. The method of claim 1, wherein said subject is administered at least 2 doses of said composition.

14. The method of claim 1, wherein said composition is administered as a gel.

15. The method of claim 1, wherein said method further comprises administering an additional therapeutic agent selected from an anti-viral agent, an antibacterial agent, an anti-fungal agent, an anti-parasitic agent, an immunostimulatory agent, a vaccine, and a chemotherapeutic agent.

16. The method of claim 15, wherein said vaccine is an Ebola virus vaccine.

17. The method of claim 15, wherein said therapeutic agent is administered separately or concurrently with said composition.

18. The method of claim 15, wherein said therapeutic agent is admixed with said composition.

19. The method of claim 1, wherein said composition is administered as a liquid.

20. The method of claim 1, wherein said adenoviral vector is an adenoviral 5 (Ad5) vector.

21. The method of claim 20, wherein said method comprises administering said Ad5 vector in an amount in the range of at least about $1 \times 10^3$ to about $1 \times 10^{14}$ viral particles per dose.

22. The method of claim 20, wherein said Ad5 vector is a replication deficient vector that comprises deletions of the E1 and E3 genes.

23. The method of claim 1, wherein said adenoviral vector comprises a promoter selected from an SV 40 promoter, CMV promoter, adenovirus early and late promoter, metallothioneine gene (MT-1) promoter, Rous sarcoma virus (RSV) promoter, and human Ubiquitin C (UbC) promoter.

24. The method of claim 1, wherein said adenoviral vector further comprises one or more of a signal sequence, a polyadenylation sequence, and enhancer, an upstream activation sequence, and a transcription termination factor that facilitates expression of said nucleic acid molecule encoding said IFN-α.

25. The method of claim 3, wherein said conIFN-α has a polypeptide sequence comprising the sequence set forth in SEQ ID NO: 11.

26. The method of claim 1, wherein said composition further comprises a pharmaceutically acceptable excipient selected from one or more of fructose, maltose, galactose, glucose, D-mannose, sorbose, lactose, sucrose, trehalose, cellobiose, raffinose, melezitose, maltodextrins, dextrans, starches, mannitol, xylitol, xylose, maltitol, lactitol, xylitol sorbitol, sorbitose, pyranosyl sorbitol, myoinositol, glycine, CaCh, hydroxyectoine, ectoine, gelatin, di-myo-inositol phosphate (DIP), cyclic 2,3 diphosphoglycerate (cDPG), 1,1-di-glycerol phosphate (DGP), p-mannosylglycerate (firoin), p-mannosylglyceramide (firoin A), and proline betaine.

27. The method of claim 1, wherein said composition is formulated for aerosolized delivery.

28. The method of claim 1, wherein said composition is admixed with a pharmaceutically acceptable liquid to form a liquid or gel.

29. The method of claim 15, wherein said additional therapeutic agent is a vaccine.

30. The method of claim 16, wherein said vaccine comprises Ad-CAGoptZGP.

31. The method of claim 1, wherein the composition is administered using a device, wherein said device comprises:

a) a container comprising the composition;

b) a nozzle for directing the composition to the pulmonary or nasal mucosa of a subject;

c) a mechanical delivery pump for delivering the composition to the nozzle, wherein activation of the pump results in a fluid connection between the nozzle and the container; and d) an actuation mechanism for activating said mechanical delivery pump.

32. The method of claim 31, wherein the actuation mechanism comprises a trigger for actuating the delivery pump at a predeterminable pressure or flow rate.

33. The method of claim 31, wherein the delivery pump comprises a liquid delivery pump for delivering a metered volume of the composition in liquid or powder form.

34. The method of claim 31, wherein the nozzle is configured to deliver an aerosol or a jet.

35. The method of claim 20, wherein said IFN-$\alpha$ is con-IFN-$\alpha$.

36. The method of claim 6, wherein said subject receives said composition at least 48 hours after exposure to said pathogen.

37. The method of claim 15, wherein said additional therapeutic agent is a vaccine against influenza, malaria, tuberculosis, smallpox, monkeypox, measles, rubella, mumps, anthrax, chickenpox, diphtheria, hepatitis A or B, *Haemophilis influenza* type b, human papillomavirus (HPV), Japanese encephalitis (JE), meningitis, pertussis, *Streptococcus pneumoniea*, polio, rabies, rotavirus, shingles, tetanus, typhoid, or Yellow Fever virus.

* * * * *

UNITED STATES PATENT AND TRADEMARK OFFICE
CERTIFICATE OF CORRECTION

PATENT NO. : 8,309,531 B2
APPLICATION NO. : 12/797575
DATED : November 13, 2012
INVENTOR(S) : Jeffrey D. Turner et al.

It is certified that error appears in the above-identified patent and that said Letters Patent is hereby corrected as shown below:

In the Specification

Column 3, Line 20, replace "hydroxiectoin" with --hydroxyectoine--.

Column 6, Line 43, replace "Papillamoviridae" with --Papillomaviridae--;

Line 48, replace "Calciviridae" with --Caliciviridae--.

Column 9, Line 32, replace "Papillamoviridae" with --Papillomaviridae--;

Line 37, replace "Calciviridae" with --Caliciviridae--.

Column 17, Line 42, replace "hydroxiectoin" with --hydroxyectoine--.

Column 23, Line 43, replace "Papillamoviridae" with --Papillomaviridae--;

Line 48, replace "Calciviridae" with --Caliciviridae--.

Column 28, Line 22, replace "Papillamoviridae" with --Papillomaviridae--;

Line 28, replace "Calciviridae" with --Caliciviridae--.

Column 31, Line 7, replace "immunovir" with --imunovir--.

Column 32, Line 5, replace "diethycicarbamazine citrate" with --diethylcarbamazine citrate--.

Signed and Sealed this
First Day of July, 2014

Michelle K. Lee
*Deputy Director of the United States Patent and Trademark Office*

CERTIFICATE OF CORRECTION (continued)
U.S. Pat. No. 8,309,531 B2

Column 33, Line 9, replace "Parana" with --Paraná--;

Line 51, replace "Papillamoviridae" with --Papillomaviridae--;

Line 56, replace "Calciviridae" with --Caliciviridae--.

Column 35, Line 62, replace "intranasaldelivery" with --intranasal delivery--.

Column 46, Line 53, replace "invervention" with --invention--.

Column 49, Line 8-9, replace "fowler Soviet Union" with --former Soviet Union--;

Line 22, replace "Terrorsm Agents" with --Terrorism Agents--.

Column 50, Line 66, replace "Amercian" with --American--.

In the Claims

Column 85, Claim 8, Line 28, replace "Papillamoviridae" with --Papillomaviridae--;

Line 29, replace "Calciviridae" with --Caliciviridae--.

Column 88, Claim 37, Line 22, replace "*pneumoniea*" with --*pneumoniae*--.

SEQUENCE LISTING

<160> NUMBER OF SEQ ID NOS: 24

<210> SEQ ID NO 1
<211> LENGTH: 876
<212> TYPE: DNA
<213> ORGANISM: Homo sapiens

<400> SEQUENCE: 1

| | | | | | |
|---|---|---|---|---|---|
| agaacctaga | gcccaaggtt | cagagtcacc | catctcagca | agcccagaag | tatctgcaat | 60 |
| atctacgatg | gcctcgccct | ttgctttact | gatggtcctg | gtggtgctca | gctgcaagtc | 120 |
| aagctgctct | ctgggctgtg | atctccctga | gacccacagc | ctggataaca | ggaggacctt | 180 |
| gatgctcctg | gcacaaatga | gcagaatctc | tccttcctcc | tgtctgatgg | acagacatga | 240 |
| ctttggattt | ccccaggagg | agtttgatgg | caaccagttc | cagaaggctc | cagccatctc | 300 |
| tgtcctccat | gagctgatcc | agcagatctt | caacctcttt | accacaaaag | attcatctgc | 360 |
| tgcttgggat | gaggacctcc | tagacaaatt | ctgcaccgaa | ctctaccagc | agctgaatga | 420 |
| cttggaagcc | tgtgtgatgc | aggaggagag | ggtgggagaa | actcccctga | tgaatgcgga | 480 |
| ctccatcttg | gctgtgaaga | aatacttccg | aagaatcact | ctctatctga | cagagaagaa | 540 |
| atacagccct | tgtgcctggg | aggttgtcag | agcagaaatc | atgagatccc | tctctttatc | 600 |
| aacaaacttg | caagaaagat | taaggaggaa | ggaataacat | ctggtccaac | atgaaaacaa | 660 |
| ttcttattga | ctcatacacc | aggtcacgct | tcatgaattt | ctgtcatttc | aaagactctc | 720 |
| accctgcta | taactatgac | catgctgata | aactgattta | tctatttaaa | tatttattta | 780 |
| actattcata | agatttaaat | tattttttgtt | catataacgt | catgtgcacc | tttacactgt | 840 |
| ggttagtgta | ataaaacatg | ttccttatat | ttactc | | | 876 |

<210> SEQ ID NO 2
<211> LENGTH: 189
<212> TYPE: PRT
<213> ORGANISM: Homo sapiens

<400> SEQUENCE: 2

Met Ala Ser Pro Phe Ala Leu Leu Met Val Leu Val Val Leu Ser Cys
1               5                   10                  15

Lys Ser Ser Cys Ser Leu Gly Cys Asp Leu Pro Glu Thr His Ser Leu
            20                  25                  30

Asp Asn Arg Arg Thr Leu Met Leu Leu Ala Gln Met Ser Arg Ile Ser
        35                  40                  45

Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

His Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
        115                 120                 125

Val Gly Glu Thr Pro Leu Met Asn Ala Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

```
Pro Cys Ala Trp Glu Val Val Arg Ala Glu Ile Met Arg Ser Leu Ser
            165                 170                 175

Leu Ser Thr Asn Leu Gln Glu Arg Leu Arg Arg Lys Glu
        180                 185
```

<210> SEQ ID NO 3
<211> LENGTH: 1143
<212> TYPE: DNA
<213> ORGANISM: Homo sapiens

<400> SEQUENCE: 3

```
gagaacctgg agcctaaggt ttaggctcac ccatttcaac cagtctagca gcatctgcaa     60
catctacaat ggccttgacc tttgcttat tggtggccct cctggtgctc agctgcaagt    120
caagctgctc tgtgggctgt gatctgcctc aaacccacag cctgggtagc aggaggacct    180
tgatgctcct ggcacagatg aggagaatct ctcttttctc ctgcttgaag gacagacatg    240
actttggatt tccccaggag gagtttggca accagttcca aaaggctgaa accatccctg    300
tcctccatga tgatccag cagatcttca atctcttcag cacaaaggac tcatctgctg    360
cttgggatga gaccctccta gacaaattct acactgaact ctaccagcag ctgaatgacc    420
tggaagcctg tgtgatacag ggggtggggg tgacagagac tcccctgatg aaggaggact    480
ccattctggc tgtgaggaaa tacttccaaa gaatcactct ctatctgaaa gagaagaaat    540
acagccctg tgcctgggag gttgtcagag cagaaatcat gagatctttt tctttgtcaa    600
caaacttgca agaaagttta agaagtaagg aatgaaaact ggttcaacat ggaaatgatt    660
ttcattgatt cgtatgccag ctcaccttt tatgatctgc catttcaaag actcatgttt    720
ctgctatgac catgacacga tttaaatctt tcaaatgtt tttaggagta ttaatcaaca    780
ttgtattcag ctcttaaggc actagtccct tacagaggac catgctgact gatccattat    840
ctatttaaat attttaaaa tattatttat ttaactattt ataaaacaac ttatttttgt    900
tcatattatg tcatgtgcac cttgcacag tggttaatgt aataaaatat gttctttgta    960
tttggtaaat ttatttgtg ttgttcattg aacttttgct atggaaactt ttgtacttgt   1020
ttattcttta aaatgaaatt ccaagcctaa ttgtgcaacc tgattacaga ataactggta   1080
cacttcattt atccatcaat attatattca agatataagt aaaaataaac tttctgtaaa   1140
cca                                                                1143
```

<210> SEQ ID NO 4
<211> LENGTH: 166
<212> TYPE: PRT
<213> ORGANISM: Homo sapiens

<400> SEQUENCE: 4

```
Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95
```

Glu Ala Cys Val Ile Gln Gly Val Gly Val Thr Glu Thr Pro Leu Met
                100                 105                 110

Lys Glu Asp Ser Ile Leu Ala Val Arg Lys Tyr Phe Gln Arg Ile Thr
            115                 120                 125

Leu Tyr Leu Lys Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 5
<211> LENGTH: 840
<212> TYPE: DNA
<213> ORGANISM: Homo sapiens

<400> SEQUENCE: 5
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctctttccat gagctacaac ttgcttggat tcctacaaag aagcagcaat   180
tttcagtgtc agaagctcct gtggcaattg aatgggaggc ttgaatactg cctcaaggac   240
aggatgaact tgacatccc tgaggagatt aagcagctgc agcagttcca gaaggaggac   300
gccgcattga ccatctatga gatgctccag aacatctttg ctatttcag acaagattca   360
tctagcactg gctggaatga gactattgtt gagaacctcc tggctaatgt ctatcatcag   420
ataaaccatc tgaagacagt cctggaagaa aaactggaga agaagatttt caccagggga   480
aaactcatga cagtctgca cctgaaaaga tattatggga ggattctgca ttacctgaag   540
gccaaggagt acagtcactg tgcctggacc atagtcagag tggaaatcct aaggaacttt   600
tacttcatta acagacttac aggttacctc cgaaactgaa gatctcctag cctgtgcctc   660
tgggactgga caattgcttc aagcattctt caaccagcag atgctgttta agtgactgat   720
ggctaatgta ctgcatatga aaggacacta gaagatttg aaatttttat taaattatga   780
gttatttta tttatttaaa ttttattttg gaaataaat tattttggt gcaaaagtca   840

<210> SEQ ID NO 6
<211> LENGTH: 187
<212> TYPE: PRT
<213> ORGANISM: Homo sapiens

<400> SEQUENCE: 6

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

```
Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
                180                 185

<210> SEQ ID NO 7
<211> LENGTH: 1240
<212> TYPE: DNA
<213> ORGANISM: Homo sapiens

<400> SEQUENCE: 7
cacattgttc tgatcatctg aagatcagct attagaagag aaagatcagt taagtccttt       60
ggacctgatc agcttgatac aagaactact gatttcaact tctttggctt aattctctcg      120
gaaacgatga atatacaag ttatatcttg gcttttcagc tctgcatcgt tttgggttct       180
cttggctgtt actgccagga cccatatgta aagaagcag aaaaccttaa gaaatatttt       240
aatgcaggtc attcagatgt agcggataat ggaactcttt tcttaggcat ttgaagaat       300 tggaaagagg agagtgacag aaaaataatg cagagccaaa ttgtctcctt ttacttcaaa      360
ctttttaaaa actttaaaga tgaccagagc atccaaaaga gtgtggagac catcaaggaa      420
gacatgaatg tcaagttttt caatagcaac aaaaagaaac gagatgactt cgaaaagctg      480
actaattatt cggtaactga cttgaatgtc aacgcaaag caatacatga actcatccaa       540
gtgatggctg aactgtcgcc agcagctaaa acagggaagc gaaaaggag tcagatgctg       600 tttcgaggtc gaagagcatc ccagtaatgg ttgtcctgcc tgcaatattt gaattttaaa      660
tctaaatcta tttattaata tttaacatta tttatatggg aatatatttt ttagactcat      720
caatcaaata gtattttata atagcaactt ttgtgtaatg aaaatgaata tctattaata      780
tatgtattat ttataattcc tatatcctgt gactgtctca cttaatcctt tgttttctga      840
ctaattaggc aaggctatgt gattacaagg ctttatctca ggggccaact aggcagccaa      900
cctaagcaag atcccatggg ttgtgtgttt atttcacttg atgatacaat gaacacttat      960
aagtgaagtg atactatcca gttactgccg gtttgaaaat atgcctgcaa tctgagccag     1020
tgctttaatg gcatgtcaga cagaacttga atgtgtcagg tgaccctgat gaaaacatag     1080
catctcagga gatttcatgc ctggtgcttc caaatattgt tgacaactgt gactgtaccc     1140
aaatggaaag taactcattt gttaaaatta tcaatatcta atatatatga ataaagtgta     1200
agttcacaac aaaaaaaaaa aaaaaaaaa aaaaaaaaa                             1240

<210> SEQ ID NO 8
<211> LENGTH: 166
<212> TYPE: PRT
<213> ORGANISM: Homo sapiens

<400> SEQUENCE: 8

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
                20                  25                  30

Asn Leu Lys Lys Tyr Phe Asn Ala Gly His Ser Asp Val Ala Asp Asn
```

```
                    35                  40                  45
Gly Thr Leu Phe Leu Gly Ile Leu Lys Asn Trp Lys Glu Ser Asp
 50                  55                  60

Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Arg
             100                 105                 110

Asp Asp Phe Glu Lys Leu Thr Asn Tyr Ser Val Thr Asp Leu Asn Val
         115                 120                 125

Gln Arg Lys Ala Ile His Glu Leu Ile Gln Val Met Ala Glu Leu Ser
     130                 135                 140

Pro Ala Ala Lys Thr Gly Lys Arg Lys Arg Ser Gln Met Leu Phe Arg
145                 150                 155                 160

Gly Arg Arg Ala Ser Gln
             165

<210> SEQ ID NO 9
<211> LENGTH: 1033
<212> TYPE: DNA
<213> ORGANISM: Bos taurus

<400> SEQUENCE: 9
gatccccgga aactagaatt cacctgaagg ttcacccaga ccccatctca gccagcccag      60
cagcagccac atcttcccca tggccttcgt gctctctcta ctgatggccc tggtgctggt     120
cagctacggc cagggacgat ctctgggttg ttacctgtct gaggaccaca tgctaggtgc     180
cagggagaac ctcaggctcc tggcccgaat gaacagactc tctcctcatc cctgtctgca     240
ggacagaaaa gactttggtc ttcctcagga gatggtggag ggcaaccagc tccagaagga     300
tcaggctatc tctgtgctcc acgagatgct ccagcagtgc tcaacctct tctacacaga      360
gcactcgtct gctgcctgga acaccaccct cctggagcag ctctgcactg ggctccaaca     420
gcagctggag gacctggacg cctgcctggg cccagtgatg ggagagaaag actctgacat     480
gggaaggatg ggccccattc tgactgtgaa gaagtacttc cagggtatcc atgtctacct     540
gaaagaaaaa gaatacagtg actgcgcctg ggaaatcatc agagtggaga tgatgagagc     600
cctctcttca tcaaccacct tgcaaaaaag gttaagaaag atgggtggag atctgaactc     660
actttgagat gactctcgct gactaagatg ccacatcacc ttcgtacact cacctgtgtt     720
catttcagaa gactctgatt tctgcttcag ccaccgaaat cattgaatta ctttaactga     780
tactttgtca gcagtaataa gcaagtagat ataaagtac tcagctgtag ggcatgagt      840
ccttaagtga tgcctgccct gatgttatct gttgttgatt tatgtattcc ttcttgcatc     900
taacatactt aaaatattag gaaatttgta aagttacatt tcatttgtac atctattaaa     960
atttctaaaa catgtttacc attttgtgtt attaaatttg tcctttgttc tatttattaa    1020
atcaaagaaa atc                                                       1033

<210> SEQ ID NO 10
<211> LENGTH: 166
<212> TYPE: PRT
<213> ORGANISM: Bos taurus

<400> SEQUENCE: 10

Met Lys Tyr Thr Ser Tyr Ile Leu Ala Phe Gln Leu Cys Ile Val Leu
  1               5                  10                  15
```

```
Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 11
<211> LENGTH: 166
<212> TYPE: PRT
<213> ORGANISM: Artificial Sequence
<220> FEATURE:
<223> OTHER INFORMATION: Synthetic Construct

<400> SEQUENCE: 11

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Ser
65                  70                  75                  80

Leu Leu Glu Lys Phe Tyr Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Arg Leu Arg Arg Lys Glu
                165

<210> SEQ ID NO 12
<211> LENGTH: 165
<212> TYPE: PRT
<213> ORGANISM: Artificial Sequence
<220> FEATURE:
```

<223> OTHER INFORMATION: Synthetic Construct

<400> SEQUENCE: 12

```
Cys Asp Leu Pro Gln Thr His Ser Leu Gly Ser Arg Arg Thr Leu Met
1               5                   10                  15
Leu Leu Ala Gln Met Arg Lys Ile Ser Leu Phe Ser Cys Leu Lys Asp
            20                  25                  30
Arg His Asp Phe Gly Phe Pro Gln Glu Glu Phe Gly Asn Gln Phe Gln
        35                  40                  45
Lys Ala Glu Thr Ile Pro Val Leu His Glu Met Ile Gln Gln Ile Phe
    50                  55                  60
Asn Leu Phe Ser Thr Lys Asp Ser Ser Ala Ala Trp Asp Glu Thr Leu
65                  70                  75                  80
Leu Asp Lys Phe Tyr Thr Glu Leu Tyr Gln Gln Leu Asn Asp Leu Glu
                85                  90                  95
Ala Cys Val Ile Gln Gly Val Gly Val Thr Glu Thr Pro Leu Met Lys
            100                 105                 110
Glu Asp Ser Ile Leu Ala Val Arg Lys Tyr Phe Gln Arg Ile Thr Leu
        115                 120                 125
Tyr Leu Lys Glu Lys Lys Tyr Ser Pro Cys Ala Trp Glu Val Val Arg
    130                 135                 140
Ala Glu Ile Met Arg Ser Phe Ser Leu Ser Thr Asn Leu Gln Glu Ser
145                 150                 155                 160
Leu Arg Ser Lys Glu
                165
```

<210> SEQ ID NO 13
<211> LENGTH: 166
<212> TYPE: PRT
<213> ORGANISM: Artificial Sequence
<220> FEATURE:
<223> OTHER INFORMATION: Synthetic Construct

<400> SEQUENCE: 13

```
Cys Asp Leu Pro Glu Thr His Ser Leu Asp Asn Arg Arg Thr Leu Met
1               5                   10                  15
Leu Leu Ala Gln Met Ser Arg Ile Ser Pro Ser Ser Cys Leu Met Asp
            20                  25                  30
Arg His Asp Phe Gly Phe Pro Gln Glu Glu Phe Asp Gly Asn Gln Phe
        35                  40                  45
Gln Lys Ala Pro Ala Ile Ser Val Leu His Glu Leu Ile Gln Gln Ile
    50                  55                  60
Phe Asn Leu Phe Thr Thr Lys Asp Ser Ser Ala Ala Trp Asp Glu Asp
65                  70                  75                  80
Leu Leu Asp Lys Phe Cys Thr Glu Leu Tyr Gln Gln Leu Asn Asp Glu
                85                  90                  95
Glu Ala Cys Val Met Gln Glu Glu Arg Val Gly Glu Thr Pro Leu Met
            100                 105                 110
Asn Val Asp Ser Ile Leu Ala Val Lys Lys Tyr Phe Arg Arg Ile Thr
        115                 120                 125
Leu Tyr Leu Thr Glu Lys Lys Tyr Ser Pro Cys Ala Trp Glu Val Val
    130                 135                 140
Arg Ala Glu Ile Met Arg Ser Leu Ser Leu Ser Thr Asn Leu Gln Glu
145                 150                 155                 160
Arg Leu Arg Arg Lys Glu
                165
```

```
<210> SEQ ID NO 14
<211> LENGTH: 166
<212> TYPE: PRT
<213> ORGANISM: Artificial Sequence
<220> FEATURE:
<223> OTHER INFORMATION: Synthetic Construct

<400> SEQUENCE: 14

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Lys Gln Ala Ile Ser Val Leu His Glu Met Ile Gln Gln Thr
    50                  55                  60

Phe Asn Leu Phe Ser Thr Lys Asp Ser Ser Ala Thr Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Ala Asn Leu Gln Glu
145                 150                 155                 160

Arg Leu Arg Arg Lys Glu
                165

<210> SEQ ID NO 15
<211> LENGTH: 166
<212> TYPE: PRT
<213> ORGANISM: Artificial Sequence
<220> FEATURE:
<223> OTHER INFORMATION: Synthetic Construct

<400> SEQUENCE: 15

Cys Asp Leu Pro Gln Thr His Ser Leu Glu His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Glu Ala Ile Ser Val Leu His Glu Val Ile Gln Gln Thr
    50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Met Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140
```

Arg Ala Glu Ile Met Arg Ser Phe Ser Ser Arg Asn Leu Gln Glu
145                 150                 155                 160

Arg Leu Arg Arg Lys Glu
                165

<210> SEQ ID NO 16
<211> LENGTH: 166
<212> TYPE: PRT
<213> ORGANISM: Artificial Sequence
<220> FEATURE:
<223> OTHER INFORMATION: Synthetic Construct

<400> SEQUENCE: 16

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
                20                  25                  30

Arg His Asp Phe Arg Ile Pro Gln Glu Glu Phe Asp Gly Asn Gln Phe
            35                  40                  45

Gln Lys Ala Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 17
<211> LENGTH: 166
<212> TYPE: PRT
<213> ORGANISM: Artificial Sequence
<220> FEATURE:
<223> OTHER INFORMATION: Synthetic Construct

<400> SEQUENCE: 17

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
                20                  25                  30

Arg Pro Asp Phe Gly Leu Pro Gln Glu Glu Phe Asp Gly Asn Gln Phe
            35                  40                  45

Gln Lys Thr Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Met Glu Gln Thr Pro Leu Met
            100                 105                 110

```
Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 18
<211> LENGTH: 166
<212> TYPE: PRT
<213> ORGANISM: Artificial Sequence
<220> FEATURE:
<223> OTHER INFORMATION: Synthetic Construct

<400> SEQUENCE: 18

Cys Asp Leu Pro Gln Thr His Ser Leu Gly Asn Arg Arg Ala Leu Ile
1               5                   10                  15

Leu Leu Ala Gln Met Gly Arg Ile Ser Asn Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 19
<211> LENGTH: 166
<212> TYPE: PRT
<213> ORGANISM: Artificial Sequence
<220> FEATURE:
<223> OTHER INFORMATION: Synthetic Construct

<400> SEQUENCE: 19

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg Pro Asp Phe Gly Leu Pro Gln Glu Glu Phe Asp Gly Asn Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80
```

Leu Leu Glu Lys Phe Ser Thr Glu Leu Tyr Gln Gln Leu Asn Asn Leu
            85                  90                  95

Glu Ala Cys Val Ile Gln Glu Val Gly Asn Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 20
<211> LENGTH: 166
<212> TYPE: PRT
<213> ORGANISM: Artificial Sequence
<220> FEATURE:
<223> OTHER INFORMATION: Synthetic Construct

<400> SEQUENCE: 20

Cys Asp Leu Pro Gln Thr His Thr Leu Arg Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Leu Phe Ser Thr Glu Leu Tyr Gln Gln Leu Asn Asp Leu
            85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Ile Glu Arg Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 21
<211> LENGTH: 166
<212> TYPE: PRT
<213> ORGANISM: Artificial Sequence
<220> FEATURE:
<223> OTHER INFORMATION: Synthetic Construct

<400> SEQUENCE: 21

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
        35                  40                  45

Gln Lys Thr Gln Ala Ile Ser Val Leu His Glu Met Ile Gln Gln Thr
         50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Lys Glu Thr Pro Leu Met
                100                 105                 110

Asn Glu Asp Phe Ile Leu Ala Val Arg Lys Tyr Phe Gln Arg Ile Thr
            115                 120                 125

Leu Tyr Leu Met Glu Lys Lys Tyr Ser Pro Cys Ala Trp Glu Val Val
        130                 135                 140

Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 22
<211> LENGTH: 166
<212> TYPE: PRT
<213> ORGANISM: Artificial Sequence
<220> FEATURE:
<223> OTHER INFORMATION: Synthetic Construct

<400> SEQUENCE: 22

Cys Asn Leu Ser Gln Thr His Ser Leu Asn Asn Arg Arg Thr Leu Met
 1               5                  10                  15

Leu Met Ala Gln Met Arg Arg Ile Ser Pro Phe Ser Cys Leu Lys Asp
                 20                  25                  30

Arg His Asp Phe Glu Phe Pro Gln Glu Glu Phe Asp Gly Asn Gln Phe
             35                  40                  45

Gln Lys Ala Gln Ala Ile Ser Val Leu His Glu Met Met Gln Gln Thr
         50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Ile Gln Glu Val Gly Val Glu Glu Thr Pro Leu Met
                100                 105                 110

Asn Glu Asp Ser Ile Leu Ala Val Arg Lys Tyr Phe Gln Arg Ile Thr
            115                 120                 125

Leu Tyr Leu Met Glu Lys Lys Tyr Ser Pro Cys Ala Met Glu Val Val
        130                 135                 140

Arg Ala Glu Ile Met Arg Ser Phe Ser Phe Ser Thr Asn Leu Gln Lys
145                 150                 155                 160

Arg Leu Arg Arg Lys Asp
                165

<210> SEQ ID NO 23
<211> LENGTH: 166
<212> TYPE: PRT
<213> ORGANISM: Artificial Sequence
<220> FEATURE:
<223> OTHER INFORMATION: Synthetic Construct

<400> SEQUENCE: 23

Cys Asp Leu Pro Gln Thr His Ser Leu Gly Asn Arg Arg Ala Leu Ile
 1               5                  10                  15

```
Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
            35                  40                  45

Gln Lys Ala Gln Ala Ile Ser Val Leu His Glu Met Ile Gln Gln Thr
            50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Met
                85                  90                  95

Glu Ala Cys Val Ile Gln Glu Val Gly Val Glu Thr Pro Leu Met
                100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 24
<211> LENGTH: 166
<212> TYPE: PRT
<213> ORGANISM: Artificial Sequence
<220> FEATURE:
<223> OTHER INFORMATION: Synthetic Construct

<400> SEQUENCE: 24

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
            35                  40                  45

Gln Lys Ala Gln Ala Ile Ser Val Leu His Glu Met Ile Gln Gln Thr
            50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Val Leu Cys Asp Gln Val Gly Val Ile Glu Ser Pro Leu Met
                100                 105                 110

Tyr Glu Asp Ser Ile Leu Ala Val Arg Lys Tyr Phe Gln Arg Ile Thr
            115                 120                 125

Leu Tyr Leu Thr Glu Lys Lys Tyr Ser Ser Cys Ala Trp Glu Val Val
        130                 135                 140

Arg Ala Glu Ile Met Arg Ser Phe Ser Leu Ser Ile Asn Leu Gln Lys
145                 150                 155                 160

Arg Leu Lys Ser Lys Glu
                165
```